US008653102B2

(12) United States Patent
Kühnert et al.

(10) Patent No.: US 8,653,102 B2
(45) Date of Patent: Feb. 18, 2014

(54) SUBSTITUTED 2-OXO- AND 2-THIOXO-DIHYDROQUINOLINE-3-CARBOXAMIDES AS KCNQ2/3 MODULATORS

(75) Inventors: Sven Kühnert, Düren (DE); Gregor Bahrenberg, Monschau-Konzen (DE); Achim Kless, Aachen (DE); Wolfgang Schröder, Aachen (DE)

(73) Assignee: Gruenenthal GmbH, Aachen (DE)

( * ) Notice: Subject to any disclaimer, the term of this patent is extended or adjusted under 35 U.S.C. 154(b) by 0 days.

(21) Appl. No.: 13/218,579

(22) Filed: Aug. 26, 2011

(65) Prior Publication Data

US 2012/0053206 A1    Mar. 1, 2012

Related U.S. Application Data

(60) Provisional application No. 61/377,537, filed on Aug. 27, 2010.

(30) Foreign Application Priority Data

Aug. 27, 2010   (EP) .................................... 10008920

(51) Int. Cl.
*A61K 31/04* (2006.01)
*C07D 215/38* (2006.01)

(52) U.S. Cl.
USPC .......................................... 514/312; 546/159

(58) Field of Classification Search
USPC ........................................... 546/159; 514/312
See application file for complete search history.

(56) References Cited

U.S. PATENT DOCUMENTS

| 4,181,658 | A | 1/1980 | Hitzel et al. |
| 4,450,167 | A | 5/1984 | Le Martret et al. |
| 4,500,348 | A | 2/1985 | Hausmann et al. |
| 4,518,775 | A | 5/1985 | Allais et al. |
| 4,542,127 | A | 9/1985 | Hitzel et al. |
| 5,641,778 | A | 6/1997 | Maibaum et al. |
| 5,646,150 | A | 7/1997 | Behforouz et al. |
| 5,646,685 | A | 7/1997 | Enokida |
| 5,719,157 | A | 2/1998 | Sohda et al. |
| 6,030,983 | A | 2/2000 | Behforouz et al. |
| 6,194,493 | B1 | 2/2001 | Stahrfeldt et al. |
| 6,395,750 | B1 | 5/2002 | Hedlund et al. |
| 6,555,685 | B1 | 4/2003 | Freer et al. |
| 7,625,900 | B2 | 12/2009 | Merla et al. |
| 7,696,238 | B2 | 4/2010 | Merla et al. |
| 7,812,170 | B2 | 10/2010 | Hughes et al. |
| 7,879,858 | B2 | 2/2011 | Merla et al. |
| 8,017,772 | B2 | 9/2011 | Merla et al. |
| 8,399,673 | B2 | 3/2013 | Kühnert et al. |
| 8,445,512 | B2 | 5/2013 | Kühnert et al. |
| 8,470,853 | B2 | 6/2013 | Anderson et al. |
| 2002/0128277 | A1 | 9/2002 | Dworetzky et al. |
| 2007/0249605 | A1 | 10/2007 | Allen et al. |
| 2007/0254862 | A1 | 11/2007 | Antel et al. |
| 2008/0167315 | A1 | 7/2008 | Merla et al. |
| 2008/0221161 | A1 | 9/2008 | Pinkerton et al. |
| 2009/0163545 | A1* | 6/2009 | Goldfarb ........................ 514/312 |
| 2009/0170840 | A1* | 7/2009 | Roth et al. .................. 514/230.5 |
| 2009/0258880 | A1 | 10/2009 | Merla et al. |
| 2009/0325948 | A1 | 12/2009 | Hurley et al. |
| 2010/0004252 | A1 | 1/2010 | Merla et al. |
| 2010/0105722 | A1 | 4/2010 | Kuehnert et al. |
| 2010/0152234 | A1 | 6/2010 | Kuhnert et al. |
| 2010/0234372 | A1 | 9/2010 | Kühnert et al. |
| 2010/0234419 | A1 | 9/2010 | Kuhnert et al. |
| 2010/0234421 | A1 | 9/2010 | Kuhnert et al. |
| 2010/0234428 | A1 | 9/2010 | Kuhnert et al. |
| 2010/0234429 | A1 | 9/2010 | Kuhnert et al. |
| 2011/0301208 | A1 | 12/2011 | Padmanabhan et al. |
| 2012/0252841 | A1 | 10/2012 | Kühnert et al. |

FOREIGN PATENT DOCUMENTS

| DE | 25 13 949 A1 | 10/1976 |
| DE | 2706977 A1 | 8/1978 |
| DE | 3111934 A1 | 10/1982 |
| DE | 3210063 A1 | 9/1983 |
| DE | 3211934 A1 | 10/1983 |
| EP | 0089597 A2 | 3/1983 |
| EP | 0480258 A1 | 9/1991 |
| EP | 0634169 A1 | 1/1995 |
| EP | 0716077 A1 | 6/1996 |
| EP | 0900824 A1 | 3/1999 |
| EP | 1 142 877 | 10/2001 |
| EP | 1449841 A1 | 8/2004 |
| EP | 1604983 A1 | 12/2005 |
| FR | 2532939 A1 | 3/1984 |
| GB | 1 495 124 | 12/1997 |
| WO | 9626925 A1 | 9/1996 |
| WO | 0042026 A1 | 7/2000 |
| WO | 0110380 A2 | 2/2001 |
| WO | 0110381 A2 | 2/2001 |

(Continued)

OTHER PUBLICATIONS

Ukrainets, Chem of Het Cmpounds, vol. 45(6), pp. 698-704, 2009.*
McKinnell, J Med Chem, vol. 52(17), pp. 5330-5343, 2009.*
Passmore et al., "KCNQ/M currents in sensory neurons: significance for pain therapy"; J. Neurosci. 2003; 23(18): 7227-36.
Blackburn-Munro and Jensen, "The anticonvulsant retigabine attenuates nociceptive behaviours in rat models of persistent and neuropathic pain"; Eur J Pharmacol. 2003; 460(2-3); 109-116.
Dost et al., "The anit-hyperalgesic activity of retigabine is mediated by KCNQ potassium channel activation" Naunyn Schmiedebergs Arch Pharmacol 2004; 369(4): 382-390.
Nielsen et al., "Pharmacological characterisation of acid-induced muscle allodynia in rats" Eur J Pharmacol. 2004; 487(1-3): 93-103.
Gribkoff, "The therapeutic potential of neuronal KCNQ channel modulators" Expert Opin Ther Targets 2003; 7(6): 737-748.

(Continued)

*Primary Examiner* — D M Seaman
(74) *Attorney, Agent, or Firm* — Norris McLaughlin & Marcus, P.A.

(57) ABSTRACT

The invention relates to substituted 2-oxo- and 2-thioxo-dihydroquinoline-3-carboxamides to pharmaceutical compositions containing these compounds and also to these compounds for use in the treatment and/or prophylaxis of pain and further diseases and/or disorders.

14 Claims, No Drawings

(56) References Cited

FOREIGN PATENT DOCUMENTS

| WO | 02066036 A1 | 8/2002 |
|---|---|---|
| WO | 02074388 A1 | 9/2002 |
| WO | 02081728 A2 | 10/2002 |
| WO | 2004026816 A1 | 4/2004 |
| WO | 2004026819 A2 | 4/2004 |
| WO | 2004058704 A2 | 7/2004 |
| WO | 2005035514 A2 | 4/2005 |
| WO | 2005/049608 | 6/2005 |
| WO | 2005105733 A1 | 11/2005 |
| WO | 2006051311 A1 | 5/2006 |
| WO | 2006092143 A1 | 9/2006 |
| WO | 2006122799 A1 | 11/2006 |
| WO | 2006122800 A1 | 11/2006 |
| WO | 2007015767 A1 | 2/2007 |
| WO | 2007030582 A2 | 3/2007 |
| WO | 2007057447 A1 | 5/2007 |
| WO | 2007/070359 A2 | 6/2007 |
| WO | 2007/070359 A3 | 6/2007 |
| WO | 2007070359 A3 | 6/2007 |
| WO | 2008007211 A1 | 1/2008 |
| WO | 2008011080 A2 | 1/2008 |
| WO | 2008011110 A2 | 1/2008 |
| WO | 2008012532 A2 | 1/2008 |
| WO | 2008/046582 | 4/2008 |
| WO | 2008050199 A2 | 5/2008 |
| WO | 2008097976 A1 | 8/2008 |
| WO | 2008/113006 | 9/2008 |
| WO | 2007133637 A1 | 9/2008 |
| WO | 2008/127274 * | 10/2008 |
| WO | 2008121850 A2 | 10/2008 |
| WO | 2008127274 A2 | 10/2008 |
| WO | 2009 018466 A1 | 2/2009 |
| WO | 2009018466 A1 | 2/2009 |
| WO | 2009019149 A1 | 2/2009 |
| WO | 2009052078 A1 | 4/2009 |
| WO | 2010/046108 | 4/2010 |
| WO | 2010039534 A2 | 4/2010 |
| WO | 2010039534 A3 | 4/2010 |
| WO | 2010075973 A1 | 7/2010 |
| WO | 2010094644 A1 | 8/2010 |
| WO | 2010094645 A1 | 8/2010 |

OTHER PUBLICATIONS

Korsgaard et al., "Anxiolytic effects of maxipost (BMS-204352) and retigabine via activation of neuronal Kv7 channels"; J Pharmacol Exp Ther. 2005, 14(1): 282-92.
Wickenden et al., "KCNQ potassium channels: drug targets for the treatment of epilepsy and pain"; Expert Opin Ther Pat 2004; 14(4): 457-469.
Gribkoff, "The therapeutic potential of neuronal Kv7 (KCNQ) channel modulators: an update", Expert Opin Ther Targets 2008, 12(5): 565-81.
Miceli et al., "Molecular pharmacology and therapeutic potential of neuronal Kv7-modulating drugs"; Curr Opin Pharmacol 2008, 8(1): 65-74.
Streng et al., "Urodynamic effects of the K+ channel (KCNQ) opener retigabine in freely moving, conscious rats"; J Urol 2004; 172: 2054-2058.
Hansen et al., "The neuronal KCNQ channel opener retigabine inhibits locomotor activity and reduces forebrain excitatory responses to the psychostimulants cocaine, methylphenidate and phencyclidine"; Eur J Pharmacol 2007, 570(1-3): 77-88.
Dencker et al., "Effect of the new antiepileptic drug retigabine in a rodent model of mania"; Epilepsy Behav 2008, 12 (1): 49-53.
Richter et al., "Antidystonic effects of Kv7 (KCNQ) channel openers in the dtsz mutant, an animal model of primary paroxysmal dystonia"; Br J Pharmacol 2006, 149(6): 747-53.
Remington's Pharmaceutical Sciences, A.R. Gennaro (Editor), 17th edition, Mack Publishing Company, Easton, Pa, 1985, Part 8, Chapters 76 to 93.
Bennett, G.J. and Xie, Y.K., A peripheral mononeuropathy in rat that produces disorders of pain sensation like those seen in man, Pain 1988, 33(1), 87-107.

Kim, S.H. and Chung, J.M., An experimental model for peripheral neuropathy produced by segmental spinal nerve ligation in the rat, Pain 1992, 50(3), 355-363.
D'Amour and Smith, "A method for determining loss of pain sensation"; J. Pharm. Exp. Ther. 72, 74 79 (1941).
D. Dubuisson et al., "The formalin test: a quantitative study of the analgesic effects of morphine, meperidine, and brain stem stimulation in rats and cats"; Pain 1977, 4, 161-174.
De Sarro et al., Naunyn-Schmiedeberg's Arch. Pharmacol. 2001, 363, 330-336.
Ukrainets et al., "4-hydroxy-2-quinolones. 93*. Synthesis and biological properties of 2-hydroxy-4-imino-1,4- dihydroquinoline-3-carboxylic acid N-R-amides"; Chemistry of Heterocyclic Compounds, vol. 42, No. 4, 2006, pp. 475-487.
Ukrainets et al., "4-hydroxy-2-quinolones. 174*. Hydrochlorides of [(Alkylamino)alkyl]amides of 1-allyl-4-hydroxy-6,7dimethoxy-2-oxo-1,2-dihydro-quinoline-3-carboxylic acid—a new class of opioid receptor antagonists"; Chemistry of Heterocyclic Compounds, vol. 46, No. 4, 2010, pp. 445-451.
Ukrainets et al., "4-hydroxy-2-quinolones,111*. Simple synthesis of 1-substituted 4-methyl-2-oxo-1,2-dihydrquinoline-3-carboxylic acids"; Chemistry of Heterocyclic Compounds, vol. 43, No. 1, 2007, pp. 58-62.
T.J. Coderre et al., Contribution of Central Neuroplasticity to Pathological Pain: Review of Clinical and Experimental Evidence, Elsevier Science Publishers, 1993, 52, 259-285.
Litchfield, J.T., Wilcoxon, J.J., A Simplified Method of Evaluating Dose-Effect Experiments, Stanford Research Laboratories, 1949, J. Pharmacol. Exp. Ther. 96, 99-113.
Disanto, Anthony. Bioavailability and Bioequivalency Testing. Chapter 77. In Remington's Pharmaceutical Sciences, 17th Ed, 1985.
Knevel, Adelbert. Separation. Chapter 78. In Remington's Pharmaceutical Sciences, 17th Ed, 1985.
Phillips, G. Briggs. Sterilization. Chapter 79. In Remington's Pharmaceutical Sciences, 17th Ed, 1985.
Siegel, Frederick. Tonicity, Osmoticity, Osmolality, and Osmolarity. Chapter 80. In Remington's Pharmaceutical Sciences, 17th Ed, 1985.
Giles et al. Plastic Packaging Materials. Chapter 81. In Remington's Pharmaceutical Sciences, 17th Ed, 1985.
Lintner, Carl. Stability of Pharmaceutical Products. Chapter 82. In Remington's Pharmaceutical Sciences, 17th Ed, 1985.
Erskine, Jr., Clyde. Quality Assurance and Control. Chapter 83. In Remington's Pharmaceutical Sciences, 17th Ed, 1985.
Nairn, J.G., Solutions, Emulsion, Suspensions and Extractives. Chapter 84. In Remington's Pharmaceutical Sciences, 17th Ed, 1985.
Avis, Kenneth. Parenteral Preparations. Chapter 85. In Remington's Pharmaceutical Sciences, 17th Ed, 1985.
Turco et al. Intravenous Admixtures. Chapter 86. In Remington's Pharmaceutical Sciences, 17th Ed, 1985.
Mullins, John. Ophthalmic Preparations. Chapter 87. In Remington's Pharmaceutical Sciences, 17th Ed, 1985.
Block, Lawrence. Medicated Applications. Chapter 88. In Remington's Pharmaceutical Sciences, 17th Ed, 1985.
Rippie, Edward. Powders. Chapter 89. In Remington's Pharmaceutical Sciences, 17th Ed, 1985.
King et al. Oral Solid Dosage Forms. Chapter 90. In Remington's Pharmaceutical Sciences, 17th Ed, 1985.
Porter, Stuart. Coating of Pharmaceutical Dosage Forms. Chapter 91. In Remington's Pharmaceutical Sciences, 17th Ed, 1985.
Longer et al. Sustained-Release Drug Delivery Systems. Chapter 92. In Remington's Pharmaceutical Sciences, 17th Ed, 1985.
Sciarra et al. Aerosols. Chapter 93. In Remington's Pharmaceutical Sciences, 17th Ed, 1985.
PCT Search Report for International application No. PCT/EP2011/004277, mailed on Oct. 10, 2011.
PCT Search Report for International application No. PCT/EP2011/004278, mailed on Oct. 11, 2011.
PCT Search Report for International application No. PCT/EP2011/004279, mailed on Oct. 11, 2011.
PCT Search Report for International application No. PCT/EP2011/004280, mailed on Oct. 11, 2011.
PCT Search Report for International application No. PCT/EP2011/004369, mailed on Jan. 30, 2012.

(56) References Cited

OTHER PUBLICATIONS

F. Zaragoza Dorwald; "Side reactions in organic synthesis; a guide to successful synthesis design", Wiley-VCH, Winheim, preface, pp. ix (2005).

Caplus 1972:59403.

F. A. Carey, R.J. Sundberg, Advanced Organic Chemistry, Parts A and B, Springer, 5th edition, 2007.

Hewawasam et al., The synthesis and structure activity relationship of 3-amino-4-benzylquinolin-2-ones: discovery of novel KCNQ2 channel openers; 14 Bioorg & Med. Chem. Letters, pp. 1615-1618 (2004).

J. March, Advanced Organic Chemistry, Wiley & Sons, 6th edition, 2007.

Martin, Yvonne et al., "Do structurally similar molecules have similar biological activity?"; 45 J. Med. Chem. pp. 4350-4358, 4536 (2002).

Patani, G. et al., Bioisosterism: a rational approach in drug design, Chem Rev. 1996, pp. 3146-3176.

Silverman, R. The organic chemistry of drug design and drug action, 2004, Elsevier, 2nd edition, pp. 9.

Wermuth, Camille G. "Molecular Variations Based on Isoteric Replacements", The Practice of Medicinal Chemistry, (1996) pp. 203-237.

Yoo et al., "Beckmann rearrangement using indium (III)chloride: synthesis of substituted oxazoloquinolines from the corresponding ketoximes of 3-acyl-1H-quinolin-4-ones"; Synthesis (2006), No. 10, pp. 1599-1612.

Ravin, Louis. Preformulation. Chapter 76. In Remington's Pharmaceutical Sciences, 17th Ed, 1985.

Vittorio, F. et al; "Ricerche su derivati alchilici della isochinolina" Farmaco, Edizione Scientificia (1984) 39(3), pp. 229-245 (English Abstract provided).

* cited by examiner

SUBSTITUTED 2-OXO- AND 2-THIOXO-DIHYDROQUINOLINE-3-CARBOXAMIDES AS KCNQ2/3 MODULATORS

This application claims priority of European Patent Application No. 10 008 920.0, filed on Aug. 27, 2010, and U.S. Provisional Application No. 61/377,537, filed on Aug. 27, 2010, the entire contents of which are incorporated herein by reference.

The invention relates to substituted 2-oxo- and 2-thioxo-dihydroquinoline-3-carboxamides to pharmaceutical compositions containing these compounds and also to these compounds for use in the treatment and/or prophylaxis of pain and further diseases and/or disorders.

The treatment of pain, in particular of neuropathic pain, is of great importance in medicine. There is a worldwide need for effective pain therapies. The urgent need for action for a target-orientated treatment of chronic and non-chronic states of pain appropriate for the patient, by which is to be understood the successful and satisfactory treatment of pain for the patient, is also documented in the large number of scientific works which have recently been published in the field of applied analgesics and of fundamental research into nociception.

A pathophysiological feature of chronic pain is the overexcitability of neurons. Neuronal excitability is influenced decisively by the activity of $K^+$ channels, since these determine decisively the resting membrane potential of the cell and therefore the excitability threshold. Heteromeric $K^+$ channels of the molecular subtype KCNQ2/3 (Kv7.2/7.3) are expressed in neurons of various regions of the central (hippocampus, amygdala) and peripheral (dorsal root ganglia) nervous system and regulate the excitability thereof. Activation of KCNQ2/3 $K^+$ channels leads to a hyperpolarization of the cell membrane and, accompanying this, to a decrease in the electrical excitability of these neurons. KCNQ2/3-expressing neurons of the dorsal root ganglia are involved in the transmission of nociceptive stimuli from the periphery into the spinal marrow (Passmore et al., J. Neurosci. 2003; 23(18): 7227-36).

It has accordingly been possible to detect an analgesic activity in preclinical neuropathy and inflammatory pain models for the KCNQ2/3 agonist retigabine (Blackburn-Munro and Jensen, Eur J. Pharmacol. 2003; 460(2-3); 109-16; Dost et al., Naunyn Schmiedebergs Arch Pharmacol 2004; 369(4): 382-390).

The KCNQ2/3 $K^+$ channel thus represents a suitable starting point for the treatment of pain; in particular of pain selected from the group consisting of chronic pain, acute pain, neuropathic pain, inflammatory pain, visceral pain and muscular pain (Nielsen et al., Eur J Pharmacol. 2004; 487(1-3): 93-103), in particular of neuropathic and inflammatory pain.

Moreover, the KCNQ2/3 $K^+$ channel is a suitable target for therapy of a large number of further diseases, such as, for example, migraine (US2002/0128277), cognitive diseases (Gribkoff, Expert Opin Ther Targets 2003; 7(6): 737-748), anxiety (Korsgaard et al., J Pharmacol Exp Ther. 2005, 14(1): 282-92), epilepsy (Wickenden et al., Expert Opin Ther Pat 2004; 14(4): 457-469; Gribkoff, Expert Opin Ther Targets 2008, 12(5): 565-81; Miceli et al., Curr Opin Pharmacol 2008, 8(1): 65-74), urinary incontinence (Streng et al., J Urol 2004; 172: 2054-2058), dependency (Hansen et al., Eur J Pharmacol 2007, 570(1-3): 77-88), mania/bipolar disorders (Dencker et al., Epilepsy Behav 2008, 12(1): 49-53) and dystonia-associated dyskinesias (Richter et al., Br J Pharmacol 2006, 149(6): 747-53).

Substituted quinolines and other compounds are known e.g. from EP 1 142 877; I. V. Ukrainets et al., Chemistry of Heterocyclic Compounds, Kluwer, Vol. 42, No. 4, 2006, pages 475-487; I. V. Ukrainets et al., Chemistry of Heterocyclic Compounds, Kluwer, Vol. 46, No. 4, 2010, pages 445-451; I. V. Ukrainets et al., Chemistry of Heterocyclic Compounds, Kluwer, Vol. 43, No. 1, 2007, pages 58-62; US 2007/254862, US 2007/249605, and WO 2005/049608.

Substituted compounds that have an affinity for the KCNQ2/3 $K^+$ channel are e.g. known from the prior art (WO 2008/046582, WO 2010/046108). Substituted quinolones are e.g. known from WO2007/070359. Substituted quinolinone compounds are further known from WO 2008/113006.

There is a demand for further compounds having comparable or better properties, not only with regard to affinity to KCNQ2/3 $K^+$ channels per se (potency, efficacy).

Thus, it may be advantageous to improve the metabolic stability, the solubility in aqueous media or the permeability of the compounds. These factors can have a beneficial effect on oral bioavailability or can alter the PK/PD (pharmacokinetic/pharmacodynamic) profile; this can lead to a more beneficial period of effectiveness, for example. A weak or non-existent interaction with transporter molecules, which are involved in the ingestion and the excretion of pharmaceutical compositions, is also to be regarded as an indication of improved bioavailability and at most low interactions of pharmaceutical compositions. Furthermore, the interactions with the enzymes involved in the decomposition and the excretion of pharmaceutical compositions should also be as low as possible, as such test results also suggest that at most low interactions, or no interactions at all, of pharmaceutical compositions are to be expected.

In addition, it may be advantageous if the compounds show a high selectivity towards other receptors of the KCNQ family (specificity), e.g. towards KCNQ1, KCNQ3/5 or KCNQ4. A high selectivity may have a positive effect on the side effects profile: for example it is known that compounds which (also) have an affinity to KCNQ1 are likely to have a potential for cardial side effects. Therefore, a high selectivity towards KCNQ1 may be desirable. However, it may also be advantageous for the compounds to show a high selectivity towards other receptors. For instance, it may be advantageous for the compounds to show a low affinity for the hERG ion channel or the L-type calcium ion channel (phenylalkylamine-, benzothiazepin-, dihydropyridine-binding site) since these receptors are known to possibly have a potential for cardial side effects. Further, an improved selectivity towards binding to other endogenic proteins (i.e. receptors or enzymes) may result in a better side effects profile and, consequently to an improved tolerance.

It was therefore an object of the invention to provide new compounds having advantages over the compounds of the prior art. These compounds should be suitable in particular as pharmacological active ingredients in pharmaceutical compositions, preferably in pharmaceutical compositions for the treatment and/or prophylaxis of disorders and/or diseases which are mediated, at least in part, by KCNQ2/3 $K^+$ channels.

That object is achieved by the subject-matter of the patent claims.

It has been found, surprisingly, that substituted compounds of the general formula (I) given below are suitable for the treatment of pain. It has also been found, surprisingly, that substituted compounds of the general formula (I) given below also have an excellent affinity for the KCNQ2/3 K+ channel and are therefore suitable for the prophylaxis and/or treatment of disorders and/or diseases that are mediated at least in part by KCNQ2/3 K+ channels. The substituted compounds thereby act as modulators, i.e. agonists or antagonists, of the KCNQ2/3 K+ channel.

The present invention therefore relates to a substituted compound of general formula (I),

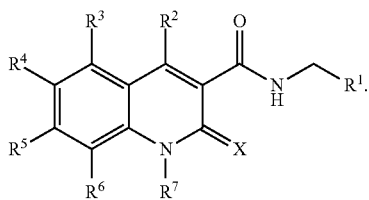

wherein

X denotes O or S, preferably O, $R^1$ represents a $C_{1-10}$-aliphatic residue, unsubstituted or mono- or polysubstituted; a $C_{3-10}$-cycloaliphatic residue or a 3 to 10 membered heterocycloaliphatic residue, in each case unsubstituted or mono- or polysubstituted and in each case optionally bridged via a $C_{1-8}$ aliphatic group, which in turn may be unsubstituted or mono- or polysubstituted; aryl or heteroaryl, in each case unsubstituted or mono- or polysubstituted and in each case optionally bridged via a $C_{1-8}$ aliphatic group, which in turn may be unsubstituted or mono- or polysubstituted;

$R^2$ represents F; Cl; Br; I; CN; $CF_3$; C(=O)H; $NO_2$; $OCF_3$; $SCF_3$; a $C_{1-4}$-aliphatic residue, a C(=O)—$C_{1-4}$ aliphatic residue, a C(=O)—O—$C_{1-4}$ aliphatic residue, a C(=O)—NH—$C_{1-4}$ aliphatic residue, a C(=O)—N($C_{1-4}$ aliphatic residue)$_2$, wherein the $C_{1-4}$ aliphatic residue may be in each case be unsubstituted or mono- or polysubstituted; a O—$C_{1-4}$-aliphatic residue, a O—C(=O)—$C_{1-4}$-aliphatic residue, a S—$C_{1-4}$-aliphatic residue, a S(=O)$_2$—$C_{1-4}$-aliphatic residue, a S(=O)$_2$—O—$C_{1-4}$-aliphatic residue, wherein the $C_{1-4}$ aliphatic residue may be in each case be unsubstituted or mono- or polysubstituted; a $C_{3-6}$-cycloaliphatic residue or a 3 to 6 membered heterocycloaliphatic residue, in each case unsubstituted or mono- or polysubstituted and in each case optionally bridged via a $C_{1-4}$ aliphatic group, which in turn may be unsubstituted or mono- or polysubstituted;

$R^3$, $R^4$, $R^5$ and $R^6$ each independently of one another represent H; F; Cl; Br; I; CN; $CF_3$; C(=O)H; C(=O)—OH; C(=O)—$NH_2$; $SCF_3$; S(=O)$_2$—OH; $NO_2$; $OCF_3$; a $C_{1-4}$-aliphatic residue, a C(=O)—$C_{1-4}$ aliphatic residue, a C(=O)—O—$C_{1-4}$ aliphatic residue, a C(=O)—NH—$C_{1-4}$ aliphatic residue, a C(=O)—N($C_{1-4}$ aliphatic residue)$_2$, wherein the $C_{1-4}$ aliphatic residue may be in each case be unsubstituted or mono- or polysubstituted; a O—$C_{1-4}$-aliphatic residue, a O—C(=O)—$C_{1-4}$-aliphatic residue, a S—$C_{1-4}$-aliphatic residue, a S(=O)$_2$—$C_{1-4}$-aliphatic residue, a S(=O)$_2$—O—$C_{1-4}$-aliphatic residue, wherein the $C_{1-4}$ aliphatic residue may be in each case be unsubstituted or mono- or polysubstituted; a NH($C_{1-4}$ aliphatic residue), a N($C_{1-4}$ aliphatic residue)$_2$, a NH—C(=O)—$C_{1-4}$ aliphatic residue, a NH—S(=O)$_2$—$C_{1-4}$-aliphatic residue, a N($C_{1-4}$ aliphatic residue)-C(=O)—$C_{1-4}$ aliphatic residue, or a N($C_{1-4}$ aliphatic residue)-S(=O)$_2$—$C_{1-4}$-aliphatic residue, wherein the $C_{1-4}$ aliphatic residue may in each case be unsubstituted or mono- or polysubstituted; a $C_{3-6}$-cycloaliphatic residue or a 3 to 6 membered heterocycloaliphatic residue, in each case unsubstituted or mono- or polysubstituted and in each case optionally bridged via a $C_{1-4}$ aliphatic group, which in turn may be unsubstituted or mono- or polysubstituted;

preferably on the condition that at least one of $R^3$, $R^4$, $R^5$ and $R^6$ is ≠H, $R^7$ represents a $C_{1-10}$-aliphatic residue, unsubstituted or mono- or polysubstituted; a $C_{3-10}$-cycloaliphatic residue or a 3 to 10 membered heterocycloaliphatic residue, in each case unsubstituted or mono- or polysubstituted and in each case optionally bridged via a $C_{1-8}$ aliphatic group, which in turn may be unsubstituted or mono- or polysubstituted;

on the condition that if $R^7$ denotes a 3 to 10 membered heterocycloaliphatic residue, the 3 to 10 membered heterocycloaliphatic residue is linked via a carbon atom, in which an "aliphatic group" and "aliphatic residue" can in each case be branched or unbranched, saturated or unsaturated, in which a "cycloaliphatic residue" and a "heterocycloaliphatic residue" can in each case be saturated or unsaturated, in which "mono- or polysubstituted" with respect to an "aliphatic group" and an "aliphatic residue" relates, with respect to the corresponding residues or groups, to the substitution of one or more hydrogen atoms each independently of one another by at least one substituent selected from the group consisting of F, Cl, Br, I, $NO_2$, $NH_2$, an NH($C_{1-4}$ aliphatic residue), a NH—C(=O)—$C_{1-4}$ aliphatic residue, a NH—S(=O)$_2$—$C_{1-4}$ aliphatic residue, OH, $OCF_3$, a O—$C_{1-4}$-aliphatic residue, a O—C(=O)—$C_{1-4}$-aliphatic residue, SH, $SCF_3$, a S—$C_{1-4}$-aliphatic residue, S(=O)$_2$OH, a S(=O)$_2$—$C_{1-4}$-aliphatic residue, a S(=O)$_2$—O—$C_{1-4}$-aliphatic residue, a S(=O)$_2$—NH—$C_{1-4}$-aliphatic residue, CN, $CF_3$, CHO, COOH, a $C_{1-4}$-aliphatic residue, a C(=O)—$C_{1-4}$-aliphatic residue, a C(=O)—O—$C_{1-4}$-aliphatic residue, a $C_{3-6}$-cycloaliphatic residue, a 3 to 6 membered heterocycloaliphatic residue, C(=O)—$NH_2$, a C(=O)—NH($C_{1-4}$ aliphatic residue), and a C(=O)—N($C_{1-4}$ aliphatic residue)$_2$;

in which "mono- or polysubstituted" with respect to a "cycloaliphatic residue" and a "heterocycloaliphatic residue" relates, with respect to the corresponding residues, to the substitution of one or more hydrogen atoms each independently of one another by at least one substituent selected from the group consisting of F, Cl, Br, I, $NO_2$, $NH_2$, an NH($C_{1-4}$ aliphatic residue), an N($C_{1-4}$ aliphatic residue)$_2$, a NH—C(=O)—$C_{1-4}$ aliphatic residue, a NH—S(=O)$_2$—$C_{1-4}$ aliphatic residue, =O, OH, $OCF_3$, a O—$C_{1-4}$-aliphatic residue, a O—C(=O)—$C_{1-4}$-aliphatic residue, SH, $SCF_3$, a S—$C_{1-4}$-aliphatic residue, S(=O)$_2$OH, a S(=O)$_2$—$C_{1-4}$-aliphatic residue, a S(=O)$_2$—O—$C_{1-4}$-aliphatic residue, a S(=O)$_2$—NH—$C_{1-4}$-aliphatic residue, CN, $CF_3$, CHO, COOH, a $C_{1-4}$-aliphatic residue, a C(=O)—$C_{1-4}$-aliphatic residue, a C(=O)—O—$C_{1-4}$-aliphatic residue, a $C_{3-6}$-cycloaliphatic residue, a 3 to 6 membered heterocycloaliphatic residue, C(=O)—$NH_2$, a C(=O)—NH($C_{1-4}$ aliphatic residue), and a C(=O)—N($C_{1-4}$ aliphatic residue)$_2$;

in which "mono- or polysubstituted" with respect to "aryl" and a "heteroaryl" relates, with respect to the corresponding residues, to the substitution of one or more hydrogen atoms each independently of one another by at least one substituent selected from the group consisting of F, Cl, Br, I, $NO_2$, $NH_2$,

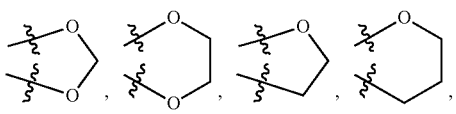

an NH($C_{1-4}$ aliphatic residue), an N($C_{1-4}$ aliphatic residue)$_2$, an NH—C(═O)—$C_{1-4}$ aliphatic residue, an NH—S(═O)$_2$—$C_{1-4}$ aliphatic residue, OH, OCF$_3$, a O—$C_{1-4}$-aliphatic residue, a O—C(═O)—$C_{1-4}$-aliphatic residue, SH, SCF$_3$, a S—$C_{1-4}$-aliphatic residue, S(═O)$_2$OH, a S(═O)$_2$—$C_{1-4}$-aliphatic residue, a S(═O)$_2$—O—$C_{1-4}$-aliphatic residue, a S(═O)$_2$—NH—$C_{1-4}$-aliphatic residue, CN, CF$_3$, C(═O)H, C(═O)OH, a $C_{1-4}$-aliphatic residue, a C(═O)—$C_{1-4}$-aliphatic residue, a C(═O)—O—$C_{1-4}$-aliphatic residue, a $C_{3-6}$-cycloaliphatic residue, a 3 to 6 membered heterocycloaliphatic residue, benzyl, aryl, heteroaryl, C(═O)—NH$_2$, a C(═O)—NH($C_{1-4}$ aliphatic residue), and a C(═O)—N($C_{1-4}$ aliphatic residue)$_2$;
with the exception of the following compound:
  1-ethyl-N-(4-methoxybenzyl)-4-methyl-2-oxo-1,2-dihydroquinoline-3-carboxamide,
in the form of the free compounds, the racemate, the enantiomers, diastereomers, mixtures of the enantiomers or diastereomers in any mixing ratio, or of an individual enantiomer or diastereomer, or in the form of the salts of physiologically acceptable acids or bases, or in the form of the solvates, in particular hydrates.

The terms "$C_{1-10}$-aliphatic residue", "$C_{1-8}$-aliphatic residue", "$C_{1-6}$-aliphatic residue" and "$C_{1-4}$-aliphatic residue" and "$C_{1-2}$-aliphatic residue" comprise in the sense of this invention acyclic saturated or unsaturated aliphatic hydrocarbon residues, which can be branched or unbranched and also unsubstituted or mono- or polysubstituted, containing 1 to 10, or 1 to 8, or 1 to 6, or 1 to 4 or 1 to 2 carbon atoms, respectively, i.e. $C_{1-10}$ alkanyls, $C_{2-10}$ alkenyls and $C_{2-10}$ alkynyls as well as $C_{1-8}$ alkanyls, $C_{2-8}$ alkenyls and $C_{2-8}$ alkynyls as well as $C_{1-6}$ alkanyls, $C_{2-6}$ alkenyls and $C_{2-6}$ alkynyls as well as $C_{1-4}$ alkanyls, $C_{2-4}$ alkenyls and $C_{2-4}$ alkynyls, as well as $C_{1-2}$ alkanyls, $C_2$-alkenyls and $C_2$ alkynyls, respectively. In this case, alkenyls comprise at least one C—C double bond (a C═C-bond) and alkynyls comprise at least one C—C triple bond (a C≡C-bond). Preferably, aliphatic residues are selected from the group consisting of alkanyl (alkyl) and alkenyl residues, more preferably are alkanyl residues. Preferred $C_{1-10}$ alkanyl residues are selected from the group consisting of methyl, ethyl, n-propyl, 2-propyl, n-butyl, isobutyl, sec.-butyl, tert.-butyl, n-pentyl, isopentyl, neopentyl, n-hexyl, n-heptyl, n-octyl, n-nonyl and n-decyl. Preferred $C_{1-8}$ alkanyl residues are selected from the group consisting of methyl, ethyl, n-propyl, 2-propyl, n-butyl, isobutyl, sec.-butyl, tert.-butyl, n-pentyl, isopentyl, neopentyl, n-hexyl, n-heptyl and n-octyl. Preferred $C_{1-6}$ alkanyl residues are selected from the group consisting of methyl, ethyl, n-propyl, 2-propyl, n-butyl, isobutyl, sec.-butyl, tert.-butyl, n-pentyl, isopentyl, neopentyl and n-hexyl. Preferred $C_{1-4}$ alkanyl residues are selected from the group consisting of methyl, ethyl, n-propyl, 2-propyl, n-butyl, isobutyl, sec.-butyl and tert.-butyl. Preferred $C_{2-10}$ alkenyl residues are selected from the group consisting of ethenyl (vinyl), propenyl (—CH$_2$CH═CH$_2$, —CH═CH—CH$_3$, —C(═CH$_2$)—CH$_3$), butenyl, pentenyl, hexenyl heptenyl, octenyl, nonenyl and decenyl. Preferred $C_{2-8}$ alkenyl residues are selected from the group consisting of ethenyl (vinyl), propenyl (—CH$_2$CH═CH$_2$, —CH═CH—CH$_3$, —C(═CH$_2$)—CH$_3$), butenyl, pentenyl, hexenyl heptenyl and octenyl. Preferred $C_{2-6}$ alkenyl residues are selected from the group consisting of ethenyl (vinyl), propenyl (—CH$_2$CH═CH$_2$, —CH═CH—CH$_3$, —C(═CH$_2$)—CH$_3$), butenyl, pentenyl and hexenyl. Preferred $C_{2-4}$ alkenyl residues are selected from the group consisting of ethenyl (vinyl), propenyl (—CH$_2$CH═CH$_2$, —CH═CH—CH$_3$, —C(═CH$_2$)—CH$_3$) and butenyl. Preferred $C_{2-10}$ alkynyl residues are selected from the group consisting of ethynyl, propynyl (—CH$_2$—C≡CH, —C≡C—CH$_3$), butynyl, pentynyl, hexynyl, heptynyl, octynyl, nonynyl and decynyl. Preferred $C_{2-8}$ alkynyl residues are selected from the group consisting of ethynyl, propynyl (—CH$_2$—C≡CH, —C≡C—CH$_3$), butynyl, pentynyl, hexynyl, heptynyl and octynyl. Preferred $C_{2-6}$ alkynyl residues are selected from the group consisting of ethynyl, propynyl (—CH$_2$—C≡CH, —C≡C—CH$_3$), butynyl, pentynyl and hexynyl Preferred $C_{2-4}$ alkynyl residues are selected from the group consisting of ethynyl, propynyl (—CH$_2$—C≡CH, —C≡C—CH$_3$) and butynyl.

The terms "$C_{3-6}$-cycloaliphatic residue" and "$C_{3-10}$-cycloaliphatic residue" mean for the purposes of this invention cyclic aliphatic hydrocarbons containing 3, 4, 5 or 6 carbon atoms and 3, 4, 5, 6, 7, 8, 9 or 10 carbon atoms, respectively, wherein the hydrocarbons in each case can be saturated or unsaturated (but not aromatic), unsubstituted or mono- or polysubstituted. The cycloaliphatic residues can be bound to the respective superordinate general structure via any desired and possible ring member of the cycloaliphatic residue. The cycloaliphatic residues can also be condensed with further saturated, (partially) unsaturated, (hetero)cyclic, aromatic or heteroaromatic ring systems, i.e. with cycloaliphatic, heterocycloaliphatic, aryl or heteroaryl residues which can in turn be unsubstituted or mono- or polysubstituted. $C_{3-10}$ cycloaliphatic residue can furthermore be singly or multiply bridged such as, for example, in the case of adamantyl, bicyclo[2.2.1]heptyl or bicyclo[2.2.2]octyl. Preferred $C_{3-10}$ cycloaliphatic residues are selected from the group consisting of cyclopropyl, cyclobutyl, cyclopentyl, cyclohexyl, cycloheptyl, cyclooctyl, cyclononyl, cyclodecyl, adamantyl,

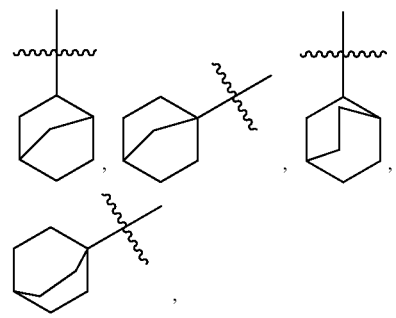

cyclopentenyl, cyclohexenyl, cycloheptenyl and cyclooctenyl. Preferred $C_{3-6}$ cycloaliphatic residues are selected from the group consisting of cyclopropyl, cyclobutyl, cyclopentyl, cyclohexyl, cyclopentenyl and cyclohexenyl.

The terms "3-6-membered heterocycloaliphatic residue" and "3-10-membered heterocycloaliphatic residue" mean for the purposes of this invention heterocycloaliphatic saturated or unsaturated (but not aromatic) residues having 3-6, i.e. 3, 4, 5 or 6 ring members, and 3-10, i.e. 3, 4, 5, 6, 7, 8, 9 or 10 ring members, respectively, in which in each case at least one, if appropriate also two or three carbon atoms are replaced by a heteroatom or a heteroatom group each selected independently of one another from the group consisting of O, S, S(=O)$_2$, N, NH and N(C$_{1-8}$ alkyl), preferably N(CH$_3$), wherein the ring members can be unsubstituted or mono- or polysubstituted. The heterocycloaliphatic residue can be bound to the superordinate general structure via any desired and possible ring member of the heterocycloaliphatic residue. The heterocycloaliphatic residues can also be condensed with further saturated, (partially) unsaturated (hetero)cycloaliphatic or aromatic or heteroaromatic ring systems, i.e. with cycloaliphatic, heterocycloaliphatic, aryl or heteroaryl residues, which can in turn be unsubstituted or mono- or polysubstituted. Preferred heterocycloaliphatic residues are selected from the group consisting of azetidinyl, aziridinyl, azepanyl, azocanyl, diazepanyl, dithiolanyl, dihydroquinolinyl, dihydropyrrolyl, dioxanyl, dioxolanyl, dioxepanyl, dihydroindenyl, dihydropyridinyl, dihydrofuranyl, dihydroisoquinolinyl, dihydroindolinyl, dihydroisoindolyl, imidazolidinyl, isoxazolidinyl, morpholinyl, oxiranyl, oxetanyl, pyrrolidinyl, piperazinyl, 4-methylpiperazinyl, piperidinyl, pyrazolidinyl, pyranyl, tetrahydropyrrolyl, tetrahydropyranyl, tetrahydroquinolinyl, tetrahydroisoquinolinyl, tetrahydroindolinyl, tetrahydrofuranyl, tetrahydropyridinyl, tetrahydrothiophenyl, tetrahydropyridoindolyl, tetrahydronaphthyl, tetrahydrocarbolinyl, tetrahydroisoxazolo-pyridinyl, thiazolidinyl and thiomorpholinyl.

The term "aryl" means for the purpose of this invention aromatic hydrocarbons having 6 to 14 ring members, including phenyls and naphthyls. Each aryl residue can be unsubstituted or mono- or polysubstituted, wherein the aryl substituents can be the same or different and in any desired and possible position of the aryl. The aryl can be bound to the superordinate general structure via any desired and possible ring member of the aryl residue. The aryl residues can also be condensed with further saturated, (partially) unsaturated, (hetero)cycloaliphatic, aromatic or heteroaromatic ring systems, i.e. with a cycloaliphatic, heterocycloaliphatic, aryl or heteroaryl residue, which can in turn be unsubstituted or mono- or polysubstituted. Examples of condensed aryl residues are benzodioxolanyl and benzodioxanyl. Preferably, aryl is selected from the group consisting of phenyl, 1-naphthyl, 2-naphthyl, fluorenyl and anthracenyl, each of which can be respectively unsubstituted or mono- or polysubstituted. A particularly preferred aryl is phenyl, unsubstituted or mono- or polysubstituted.

The term "heteroaryl" for the purpose of this invention represents a 5 or 6-membered cyclic aromatic residue containing at least 1, if appropriate also 2, 3, 4 or 5 heteroatoms, wherein the heteroatoms are each selected independently of one another from the group S, N and O and the heteroaryl residue can be unsubstituted or mono- or polysubstituted; in the case of substitution on the heteroaryl, the substituents can be the same or different and be in any desired and possible position of the heteroaryl. The binding to the superordinate general structure can be carried out via any desired and possible ring member of the heteroaryl residue. The heteroaryl can also be part of a bi- or polycyclic system having up to 14 ring members, wherein the ring system can be formed with further saturated, (partially) unsaturated, (hetero)cycloaliphatic or aromatic or heteroaromatic rings, i.e. with a cycloaliphatic, heterocycloaliphatic, aryl or heteroaryl residue, which can in turn be unsubstituted or mono- or polysubstituted. It is preferable for the heteroaryl residue to be selected from the group consisting of benzofuranyl, benzoimidazolyl, benzothienyl, benzothiadiazolyl, benzothiazolyl, benzotriazolyl, benzooxazolyl, benzooxadiazolyl, quinazolinyl, quinoxalinyl, carbazolyl, quinolinyl, dibenzofuranyl, dibenzothienyl, furyl (furanyl), imidazolyl, imidazothiazolyl, indazolyl, indolizinyl, indolyl, isoquinolinyl, isoxazoyl, isothiazolyl, indolyl, naphthyridinyl, oxazolyl, oxadiazolyl, phenazinyl, phenothiazinyl, phthalazinyl, pyrazolyl, pyridyl (2-pyridyl, 3-pyridyl, 4-pyridyl), pyrrolyl, pyridazinyl, pyrimidinyl, pyrazinyl, purinyl, phenazinyl, thienyl (thiophenyl), triazolyl, tetrazolyl, thiazolyl, thiadiazolyl and triazinyl. Furyl, pyridyl, oxazolyl, thiazolyl and thienyl are particularly preferred.

The terms "aryl, heteroaryl, a heterocycloaliphatic residue, or a cycloaliphatic residue bridged via a C$_{1-4}$-aliphatic group or via a C$_{1-8}$-aliphatic group" mean for the purpose of the invention that the expressions "aryl, heteroaryl, heterocycloaliphatic residue and cycloaliphatic residue" have the above-defined meanings and are bound to the respective superordinate general structure via a C$_{1-4}$-aliphatic group or via a C$_{1-8}$-aliphatic group, respectively. The C$_{1-4}$ aliphatic group and the C$_{1-8}$-aliphatic group can in all cases be branched or unbranched, unsubstituted or mono- or polysubstituted. The C$_{1-4}$ aliphatic group can in all cases be furthermore saturated or unsaturated, i.e. can be a C$_{1-4}$ alkylene group, a C$_{2-4}$ alkenylene group or a C$_{2-4}$ alkynylene group. The same applies to a C$_{1-8}$-aliphatic group, i.e. a C$_{1-8}$-aliphatic group can in all cases be furthermore saturated or unsaturated, i.e. can be a C$_{1-8}$ alkylene group, a C$_{2-8}$ alkenylene group or a C$_{2-8}$ alkynylene group. Preferably, the C$_{1-4}$-aliphatic group is a C$_{1-4}$ alkylene group or a C$_{2-4}$ alkenylene group, more preferably a C$_{1-4}$ alkylene group. Preferably, the C$_{1-8}$-aliphatic group is a C$_{1-8}$ alkylene group or a C$_{2-8}$ alkenylene group, more preferably a C$_{1-8}$ alkylene group. Preferred C$_{1-4}$ alkylene groups are selected from the group consisting of —CH$_2$—, —CH$_2$—CH$_2$—, —CH(CH$_3$)—, —CH$_2$—CH$_2$—CH$_2$—, —CH(CH$_3$)—CH$_2$—, —CH(CH$_2$CH$_3$)—, —CH$_2$—(CH$_2$)$_2$—CH$_2$—, —CH(CH$_3$)—CH$_2$—CH$_2$—, —CH$_2$—CH(CH$_3$)—CH$_2$—, —CH(CH$_3$)—CH(CH$_3$)—, —CH(CH$_2$CH$_3$)—CH$_2$—, —C(CH$_3$)$_2$—CH$_2$—, —CH(CH$_2$CH$_2$CH$_3$)— and —C(CH$_3$)(CH$_2$CH$_3$)—. Preferred C$_{2-4}$ alkenylene groups are selected from the group consisting of —CH=CH—, —CH=CH—CH$_2$—, —C(CH$_3$)=CH$_2$—, —CH=CH—CH$_2$—CH$_2$—, —CH$_2$—CH=CH—CH$_2$—, —CH=CH—CH=CH—, —C(CH$_3$)= CH—CH$_2$—, —CH=C(CH$_3$)—CH$_2$—, —C(CH$_3$)=C(CH$_3$)— and —C(CH$_2$CH$_3$)=CH—. Preferred C$_{2-4}$ alkynylene groups are selected from the group consisting of —C≡C—, —C≡C—CH$_2$—, —C≡C—CH$_2$—CH$_2$—, —C≡C—CH(CH$_3$)—, —CH$_2$—C≡C—CH$_2$— and —C≡C—C≡C—. Preferred C$_{1-8}$ alkylene groups are selected from the group consisting of —CH$_2$—, —CH$_2$—CH$_2$—, —CH(CH$_3$)—, —CH$_2$—CH$_2$—CH$_2$—, —CH(CH$_3$)—CH$_2$—, —CH(CH$_2$CH$_3$)—, —CH$_2$—(CH$_2$)$_2$—CH$_2$—, —CH(CH$_3$)—CH$_2$—CH$_2$—, —CH$_2$—CH(CH$_3$)—CH$_2$—, —CH(CH$_3$)—CH(CH$_3$)—, —CH(CH$_2$CH$_3$)—CH$_2$—, —C(CH$_3$)$_2$—CH$_2$—, —CH(CH$_2$CH$_2$CH$_3$)—, —C(CH$_3$)(CH$_2$CH$_3$)—, —CH$_2$—(CH$_2$)$_3$—CH$_2$—, —CH(CH$_3$)—CH$_2$—CH$_2$—CH$_2$—, —CH$_2$—CH(CH$_3$)—CH$_2$—CH$_2$—, —CH(CH$_3$)—CH$_2$—CH(CH$_3$)—, —CH(CH$_3$)—CH(CH$_3$)—CH$_2$—, —C(CH$_3$)$_2$—CH$_2$—CH$_2$—, —CH$_2$—C(CH$_3$)$_2$—CH$_2$—, —CH(CH$_2$CH$_3$)—CH$_2$—CH$_2$—, —CH$_2$—CH(CH$_2$CH$_3$)—CH$_2$—, —C(CH$_3$)$_2$—CH(CH$_3$)—, —CH(CH$_2$CH$_3$)—CH(CH$_3$)—, —C(CH$_3$)(CH$_2$CH$_3$)—CH$_2$—, —CH(CH$_2$CH$_2$CH$_3$)—CH$_2$—, —C(CH$_2$CH$_2$CH$_3$)—CH$_2$—, —CH(CH$_2$CH$_2$CH$_2$CH$_3$)—, —C(CH$_3$)(CH$_2$CH$_2$CH$_3$)—, —C(CH$_2$CH$_3$)$_2$— and —CH$_2$—(CH$_2$)$_4$—CH$_2$—. Preferred C$_{2-8}$ alkenylene groups are selected from the group consisting of —CH=CH—, —CH=CH—CH$_2$—, —C(CH$_3$)=CH$_2$—, —CH=CH—CH$_2$—CH$_2$—, —CH$_2$—CH=CH—CH$_2$—, —CH=CH—CH=CH—, —C(CH$_3$)=CH—CH$_2$—, —CH=C(CH$_3$)—CH$_2$—, —C(CH$_3$)=C(CH$_3$)—, —C(CH$_2$CH$_3$)=CH—, —CH=CH—CH$_2$—CH$_2$—CH$_2$—, —CH$_2$—CH=CH$_2$—CH$_2$—CH$_2$—, —CH=CH—CH=CH—CH$_2$—CH$_2$— and —CH=CH$_2$—CH=CH—CH$_2$—. Preferred C$_{2-8}$ alkynylene groups are selected from the group consisting of —C≡C—, —C≡C—CH$_2$—, —C≡C—CH$_2$—CH$_2$—, —C≡C—CH(CH$_3$)—, —CH$_2$—C≡C—CH$_2$—, —C≡C—C≡C—, —C≡C—C(CH$_3$)$_2$—, —C≡C—CH$_2$—CH$_2$—CH$_2$—, —CH$_2$—C≡C—CH$_2$—CH$_2$—, —C≡C—C≡C—CH$_2$— and —C≡C—CH$_2$—C≡C.

In relation to "aliphatic residue" and "aliphatic group" the term "mono- or polysubstituted" refers in the sense of this invention, with respect to the corresponding residues or groups, to the single substitution or multiple substitution, e.g. disubstitution, trisubstitution and tetrasubstitution, of one or more hydrogen atoms each independently of one another by at least one substituent selected from the group consisting of F, Cl, Br, I, NO$_2$, NH$_2$, an NH(C$_{1-4}$ aliphatic residue), a NH—C(=O)—C$_{1-4}$ aliphatic residue, a NH—S(=O)$_2$—C$_{1-4}$ aliphatic residue, OH, OCF$_3$, a O—C$_{1-4}$-aliphatic residue, a O—C(=O)—C$_{1-4}$-aliphatic residue, SH, SCF$_3$, a S—C$_{1-4}$-aliphatic residue, S(=O)$_2$OH, a S(=O)$_2$—C$_{1-4}$-aliphatic residue, a S(=O)$_2$—O—C$_{1-4}$-aliphatic residue, a S(=O)$_2$—NH—C$_{1-4}$-aliphatic residue, CN, CF$_3$, CHO, COOH, a C$_{1-4}$-aliphatic residue, a C(=O)—C$_{1-4}$-aliphatic residue, a C(=O)—O—C$_{1-4}$-aliphatic residue, a C$_{3-6}$-cycloaliphatic residue, a 3 to 6 membered heterocycloaliphatic residue, C(=O)—NH$_2$, a C(=O)—NH(C$_{1-4}$ aliphatic residue), and a C(=O)—N(C$_{1-4}$ aliphatic residue)$_2$. The term "polysubstituted" with respect to polysubstituted residues and groups includes the polysubstitution of these residues and groups either on different or on the same atoms, for example trisubstituted on the same carbon atom, as in the case of CF$_3$ or CH$_2$CF$_3$, or at various points, as in the case of CH(OH)—CH=CH—CHCl$_2$. A substituent can if appropriate for its part in turn be mono- or polysubstituted. The multiple substitution can be carried out using the same or using different substituents.

In relation to "cycloaliphatic residue" and "heterocycloaliphatic residue" the term "mono- or polysubstituted" refers in the sense of this invention, with respect to the corresponding residues, to the single substitution or multiple substitution, e.g. disubstitution, trisubstitution and tetrasubstitution, of one or more hydrogen atoms each independently of one another by at least one substituent selected from the group consisting of F, Cl, Br, I, NO$_2$, NH$_2$, an NH(C$_{1-4}$ aliphatic residue), an N(C$_{1-4}$ aliphatic residue)$_2$, a NH—C(=O)—C$_{1-4}$ aliphatic residue, a NH—S(=O)$_2$—C$_{1-4}$ aliphatic residue, =O, OH, OCF$_3$, a O—C$_{1-4}$-aliphatic residue, a O—C(=O)—C$_{1-4}$-aliphatic residue, SH, SCF$_3$, a S—C$_{1-4}$-aliphatic residue, S(=O)$_2$OH, a S(=O)$_2$—C$_{1-4}$-aliphatic residue, a S(=O)$_2$—O—C$_{1-4}$-aliphatic residue, a S(=O)$_2$—NH—C$_{1-4}$-aliphatic residue, CN, CF$_3$, CHO, COOH, a C$_{1-4}$-aliphatic residue, a C(=O)—C$_{1-4}$-aliphatic residue, a C(=O)—O—C$_{1-4}$-aliphatic residue, a C$_{3-6}$-cycloaliphatic residue, a 3 to 6 membered heterocycloaliphatic residue, C(=O)—NH$_2$, a C(=O)—NH(C$_{1-4}$ aliphatic residue), and a C(=O)—N(C$_{1-4}$ aliphatic residue)$_2$. The term "polysubstituted" with respect to polysubstituted residues and groups includes the polysubstitution of these residues and groups either on different or on the same atoms, for example disubstituted on the same carbon atom, as in the case of 1,1-difluorocyclohexyl, or at various points, as in the case of 1-chloro-3-fluorocyclohexyl. A substituent can if appropriate for its part in turn be mono- or polysubstituted. The multiple substitution can be carried out using the same or using different substituents.

Preferred substituents of "aliphatic residue" and "aliphatic group" are selected from the group consisting of F, Cl, Br, I, NO$_2$, NH$_2$, an NH(C$_{1-4}$ aliphatic residue), OH, OCF$_3$, a O—C$_{1-4}$-aliphatic residue, a O—(C$_{1-4}$-aliphatic group)-O—C$_{1-4}$-aliphatic residue, a O—(C$_{1-4}$-aliphatic group)-OH, SH, SCF$_3$, a S—C$_{1-4}$-aliphatic residue, a S(=O)$_2$—C$_{1-4}$-aliphatic residue, a S(=O)$_2$—NH—C$_{1-4}$-aliphatic residue, CN, CF$_3$, a C$_{1-4}$-aliphatic residue, a C(=O)—C$_{1-4}$-aliphatic residue, a C(=O)—O—C$_{1-4}$-aliphatic residue, COOH, CONH$_2$, a C(=O)—NH(C$_{1-4}$ aliphatic residue), and a C(=O)—N(C$_{1-4}$ aliphatic residue)$_2$.

Preferred substituents of "cycloaliphatic residue" and "heterocycloaliphatic residue" are selected from the group consisting of F, Cl, Br, I, NO$_2$, NH$_2$, an NH(C$_{1-4}$ aliphatic residue), an N(C$_{1-4}$ aliphatic residue)$_2$, =O, OH, OCF$_3$, a O—C$_{1-4}$-aliphatic residue, SH, SCF$_3$, a S—C$_{1-4}$-aliphatic residue, a S(=O)$_2$—C$_{1-4}$-aliphatic residue, a S(=O)$_2$—NH—C$_{1-4}$-aliphatic residue, CN, CF$_3$, a C$_{1-4}$-aliphatic residue, a C(=O)—C$_{1-4}$-aliphatic residue, a C(=O)—O—C$_{1-4}$-aliphatic residue, CONH$_2$, a C(=O)—NH(C$_{1-4}$ aliphatic residue), and a C(=O)—N(C$_{1-4}$ aliphatic residue)$_2$.

In relation to "aryl" and "heteroaryl" the term "mono- or polysubstituted" refers in the sense of this invention to the single substitution or multiple substitution, e.g. disubstitution, trisubstitution and tetrasubstitution, of one or more hydrogen atoms each independently of one another by at least one substituent selected from the group consisting of F, Cl, Br, I, NO$_2$, NH$_2$,

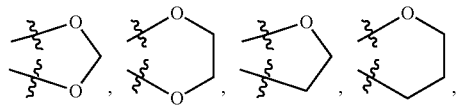

an NH(C$_{1-4}$ aliphatic residue), an N(C$_{1-4}$ aliphatic residue)$_2$, an NH—C(=O)—C$_{1-4}$ aliphatic residue, an NH—S(=O)$_2$—C$_{1-4}$ aliphatic residue, OH, OCF$_3$, a O—C$_{1-4}$-aliphatic residue, a O—C(=O)—C$_{1-4}$-aliphatic residue, SH, SCF$_3$, a S—C$_{1-4}$-aliphatic residue, S(=O)$_2$OH, a S(=O)$_2$—C$_{1-4}$-aliphatic residue, a S(=O)$_2$—O—C$_{1-4}$-aliphatic residue, a S(=O)$_2$—NH—C$_{1-4}$-aliphatic residue, CN, CF$_3$, C(=O)H, C(=O)OH, a C$_{1-4}$-aliphatic residue, a C(=O)—C$_{1-4}$-aliphatic residue, a C(=O)—O—C$_{1-4}$-aliphatic residue, a C$_{3-6}$-cycloaliphatic residue, a 3 to 6 membered heterocycloaliphatic residue, benzyl, aryl, heteroaryl, C(=O)—NH$_2$, a C(=O)—NH(C$_{1-4}$ aliphatic residue), and a C(=O)—N(C$_{1-4}$ aliphatic residue)$_2$ on one or if appropriate different atoms, wherein a substituent can if appropriate for its part in turn be mono- or polysubstituted. The multiple substitution is carried out employing the same or using different substituents.

Preferred substituents of "aryl" and "heteroaryl" are selected from the group consisting of F, Cl, Br, I, NO$_2$, NH$_2$,

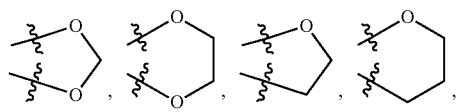

an NH(C$_{1-4}$ aliphatic residue), an N(C$_{1-4}$ aliphatic residue)$_2$, an NH—C(=O)—C$_{1-4}$ aliphatic residue, an NH—S(=O)$_2$—C$_{1-4}$ aliphatic residue, OH, OCF$_3$, a O—C$_{1-4}$-aliphatic residue, SH, SCF$_3$, a S—C$_{1-4}$-aliphatic residue, S(=O)$_2$OH, a S(=O)$_2$—C$_{1-4}$-aliphatic residue, a S(=O)$_2$—

NH—C$_{1-4}$-aliphatic residue, CN, CF$_3$, a C$_{1-4}$-aliphatic residue, a C(=O)—C$_{1-4}$-aliphatic residue, a C(=O)—O—C$_{1-4}$-aliphatic residue, a C$_{3-6}$-cycloaliphatic residue, a 3 to 6 membered heterocycloaliphatic residue, CONH$_2$, a C(=O)—NH(C$_{1-4}$ aliphatic residue), a C(=O)—N(C$_{1-4}$ aliphatic residue)$_2$, aryl, preferably phenyl, or benzyl, in each case unsubstituted or mono- or polysubstituted with at least one substituent selected from the group consisting of F, Cl, Br, I, CN, CF$_3$, CH$_3$, C$_2$H$_5$, iso-propyl, tert.-butyl, C(=O)—OH, C(=O)—CH$_3$, C(=O)—C$_2$H$_5$, C(=O)—O—CH$_3$ and C(=O)—O—C$_2$H$_5$, O—CH$_3$, OCF$_3$, O—CH$_2$—OH, O—CH$_2$—O—CH$_3$, SH, S—CH$_3$, SCF$_3$, NO$_2$, NH$_2$, N(CH$_3$)$_2$, N(CH$_3$)(C$_2$H$_5$) and N(C$_2$H$_5$)$_2$, heteroaryl, preferably pyridyl, thienyl, furyl, thiazolyl or oxazolyl, in each case unsubstituted or mono- or polysubstituted with at least one substituent selected from the group consisting of F, Cl, Br, I, CN, CF$_3$, CH$_3$, C$_2$H$_5$, iso-propyl, tert.-butyl, C(=O)—OH, C(=O)—CH$_3$, C(=O)—C$_2$H$_5$, C(=O)—O—CH$_3$ and C(=O)—O—C$_2$H$_5$, O—CH$_3$, OCF$_3$, O—CH$_2$—OH, O—CH$_2$—O—CH$_3$, SH, S—CH$_3$, SCF$_3$, NO$_2$, NH$_2$, N(CH$_3$)$_2$, N(CH$_3$)(C$_2$H$_5$) and N(C$_2$H$_5$)$_2$.

The compounds according to the invention are defined by substituents, for example by R$^1$, R$^2$ and R$^3$ (1$^{st}$ generation substituents) which are for their part if appropriate substituted (2$^{nd}$ generation substituents). Depending on the definition, these substituents of the substituents can for their part be resubstituted (3$^{rd}$ generation substituents). If, for example, R$^1$=a C$_{1-10}$ aliphatic residue (1$^{st}$ generation substituent), then the C$_{1-10}$ aliphatic residue can for its part be substituted, for example with a NH—C$_{1-4}$ aliphatic residue (2$^{nd}$ generation substituent). This produces the functional group R$^1$=(C$_{1-10}$ aliphatic residue-NH—C$_{1-4}$ aliphatic residue). The NH—C$_{1-4}$ aliphatic residue can then for its part be resubstituted, for example with Cl (3$^{rd}$ generation substituent). Overall, this produces the functional group R$^1$=C$_{1-10}$ aliphatic residue-NH—C$_{1-4}$ aliphatic residue, wherein the C$_{1-4}$ aliphatic residue of the NH—C$_{1-4}$ aliphatic residue is substituted by Cl.

However, in a preferred embodiment, the 3$^{rd}$ generation substituents may not be resubstituted, i.e. there are then no 4$^{th}$ generation substituents.

In another preferred embodiment, the 2$^{nd}$ generation substituents may not be resubstituted, i.e. there are then not even any 3$^{rd}$ generation substituents. In other words, in this embodiment, in the case of general formula (I), for example, the functional groups for R$^1$ to R$^7$ can each if appropriate be substituted; however, the respective substituents may then for their part not be resubstituted.

In some cases, the compounds according to the invention are defined by substituents which are or carry an aryl or heteroaryl residue, respectively unsubstituted or mono- or polysubstituted, or which form together with the carbon atom(s) or heteroatom(s) connecting them, as the ring member or as the ring members, a ring, for example an aryl or heteroaryl, in each case unsubstituted or mono- or polysubstituted. Both these aryl or heteroaryl residues and the (hetero)aromatic ring systems formed in this way can if appropriate be condensed with a cycloaliphatic, preferably a C$_{3-6}$ cycloaliphatic residue, or heterocycloaliphatic residue, preferably a 3 to 6 membered heterocycloaliphatic residue, or with aryl or heteroaryl, e.g. with a C$_{3-6}$ cycloaliphatic residue such as cyclopentyl, or a 3 to 6 membered heterocycloaliphatic residue such as morpholinyl, or an aryl such as phenyl, or a heteroaryl such as pyridyl, wherein the cycloaliphatic or heterocycloaliphatic residues, aryl or heteroaryl residues condensed in this way can for their part be respectively unsubstituted or mono- or polysubstituted.

In some cases, the compounds according to the invention are defined by substituents which are or carry a cycloaliphatic residue or a heterocycloaliphatic residue, respectively, in each case unsubstituted or mono- or polysubstituted, or which form together with the carbon atom(s) or heteroatom(s) connecting them, as the ring member or as the ring members, a ring, for example a cycloaliphatic or a heterocycloaliphatic ring system. Both these cycloaliphatic or heterocycloaliphatic ring systems and the (hetero)cycloaliphatic ring systems formed in this manner can if appropriate be condensed with aryl or heteroaryl or with a cycloaliphatic residue, preferably a C$_{3-6}$ cycloaliphatic residue, or a heterocycloaliphatic residue, preferably a 3 to 6 membered heterocycloaliphatic residue, e.g. with an aryl such as phenyl, or a heteroaryl such as pyridyl, or a cycloaliphatic residue such as cyclohexyl, or a heterocycloaliphatic residue such as morpholinyl, wherein the aryl or heteroaryl residues or cycloaliphatic or heterocycloaliphatic residues condensed in this way can for their part be respectively unsubstituted or mono- or polysubstituted.

Within the scope of the present invention, the symbol

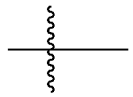

used in the formulae denotes a link of a corresponding residue to the respective superordinate general structure.

If a residue occurs multiply within a molecule, then this residue can have respectively different meanings for various substituents: if, for example, both R$^2$ and R$^3$ denote a 3 to 6 membered heterocycloaliphatic residue, then the 3 to 6 membered heterocycloaliphatic residue can e.g. represent morpholinyl for R$^2$ and can represent piperazinyl for R$^3$.

The term "salts of physiologically acceptable acids" refers in the sense of this invention to salts of the respective active ingredient with inorganic or organic acids which are physiologically acceptable—in particular when used in human beings and/or other mammals. Hydrochloride is particularly preferred. Examples of physiologically acceptable acids are: hydrochloric acid, hydrobromic acid, sulphuric acid, methanesulphonic acid, p-toluenesulphonic acid, carbonic acid, formic acid, acetic acid, oxalic acid, succinic acid, tartaric acid, mandelic acid, fumaric acid, maleic acid, lactic acid, citric acid, glutamic acid, saccharic acid, monomethylsebacic acid, 5-oxoproline, hexane-1-sulphonic acid, nicotinic acid, 2, 3 or 4-aminobenzoic acid, 2,4,6-trimethylbenzoic acid, α-lipoic acid, acetyl glycine, hippuric acid, phosphoric acid, aspartic acid. Citric acid and hydrochloric acid are particularly preferred.

The term "salts of physiologically acceptable bases" refers in the sense of this invention to salts of the respective compound according to the invention—as an anion, e.g. upon deprotonation of a suitable functional group—with at least one cation or base—preferably with at least one inorganic cation—which are physiologically acceptable—in particular when used in human beings and/or other mammals. Particularly preferred are the salts of the alkali and alkaline earth metals, in particular (mono-) or (di)sodium, (mono-) or (di)potassium, magnesium or calcium salts, but also ammonium salts [NH$_x$R$_{4-x}$]$^+$, in which x=0, 1, 2, 3 or 4 and R represents a branched or unbranched C$_{1-4}$ aliphatic residue.

Preferred embodiments of the compound according to general formula (I) have general formulae (I-I), and/or (I-II):

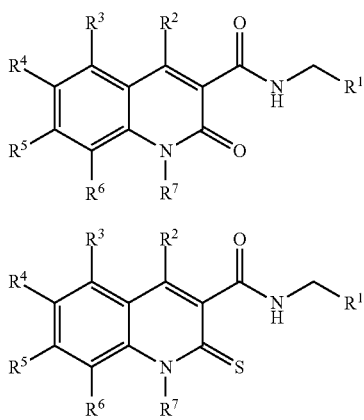

(I-I)

(I-II)

Particularly preferred is a compound according to general formula (I-I), i.e. a compound according to general formula (I), wherein X denotes O.

Further preferred embodiments of the compound according to general formula (I) have general formulae (Ia), (Ib), (Ic) and/or (Id):

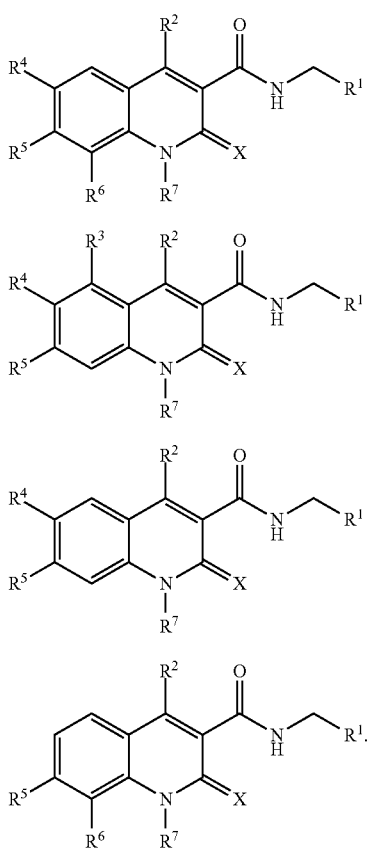

(Ia)

(Ib)

(Ic)

(Id)

Another preferred embodiment of present invention is a compound according to general formula (I), wherein
R[1] denotes a $C_{1-10}$-aliphatic residue, preferably a $C_{1-8}$-aliphatic residue, unsubstituted or mono- or polysubstituted with at least one substituent selected from the group consisting of F, Cl, Br, I, $NO_2$, $NH_2$, an $NH(C_{1-4}$ aliphatic residue), OH, an O—$C_{1-4}$-aliphatic residue, $OCF_3$, SH, $SCF_3$, a S—$C_{1-4}$-aliphatic residue, $CF_3$, CN, a $C_{1-4}$-aliphatic residue, and C(=O)—OH, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, C(=O)—OH, a $C_{3-6}$ cycloaliphatic residue, and a 3 to 6 membered heterocycloaliphatic residue, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH, and wherein the $C_{3-10}$-cycloaliphatic residue or the 3 to 10 membered heterocycloaliphatic residue may in each case optionally bridged via a $C_{1-8}$ aliphatic group, preferably a $C_{1-4}$ aliphatic group, which in turn may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH, or denotes an aryl or heteroaryl, in each case unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, C(=O)—OH, C(=O)—$CH_3$, C(=O)—$C_2H_5$, C(=O)—O—$CH_3$ and C(=O)—O—$C_2H_5$, a $C_{3-6}$ cycloaliphatic residue, a 3 to 6 membered heterocycloaliphatic residue,

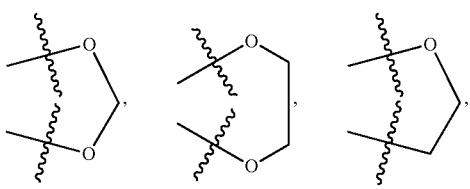

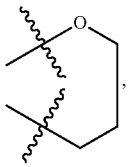

benzyl, phenyl, thienyl, pyridyl, furyl, thiazolyl and oxazolyl,
wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted $O-C_{1-4}$-aliphatic residue, and wherein benzyl, phenyl, thienyl, pyridyl, furyl, thiazolyl and oxazolyl may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, an $O-C_{1-4}$ aliphatic residue, $OCF_3$, $O-CH_2-OH$, $O-CH_2-O-CH_3$, SH, $SCF_3$, a $S-C_{1-4}$ aliphatic residue, $CF_3$, CN, a $C_{1-4}$-aliphatic residue, $C(=O)-OH$, $C(=O)-CH_3$, $C(=O)-C_2H_5$, $C(=O)-O-CH_3$ and $C(=O)-O-C_2H_5$, wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an $O-C_{1-4}$ aliphatic residue, $OCF_3$, SH, $SCF_3$, a $S-C_{1-4}$ aliphatic residue, $CF_3$, CN, a $C_{1-4}$-aliphatic residue and $C(=O)-OH$, and wherein the aryl or the heteroaryl residue may in each case be optionally bridged via a $C_{1-8}$ aliphatic group, preferably a $C_{1-4}$ aliphatic group, which in turn may be unsubstituted or mono- or polysubstituted with at least one substituent selected from the group consisting of F, Cl, Br, I, $NO_2$, $NH_2$, an $NH(C_{1-4}$ aliphatic residue), OH, an $O-C_{1-4}$ aliphatic residue, $OCF_3$, SH, $SCF_3$, a $S-C_{1-4}$ aliphatic residue, $CF_3$, CN and $C(=O)-OH$, X represents O or S;

$R^2$ represents F; Cl; Br; I; CN; $CF_3$; $NO_2$; $OCF_3$; $SCF_3$; a $C_{1-4}$-aliphatic residue, a $S-C_{1-4}$-aliphatic residue, a $O-C_{1-4}$-aliphatic residue, wherein the $C_{1-4}$ aliphatic residue may be in each case be unsubstituted or mono- or polysubstituted; a $C_{3-6}$-cycloaliphatic residue or a 3 to 6 membered heterocycloaliphatic residue, in each case unsubstituted or mono- or polysubstituted and in each case optionally bridged via a $C_{1-4}$ aliphatic group, which in turn may be unsubstituted or mono- or polysubstituted, preferably represents F; Cl; Br; I; CN; $CF_3$; $NO_2$; $OCF_3$; $SCF_3$; a $C_{1-4}$-aliphatic residue, a $S-C_{1-4}$-aliphatic residue, a $O-C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, and an unsubstituted $O-C_{1-4}$-aliphatic residue; a $C_{3-6}$-cycloaliphatic residue or a 3 to 6 membered heterocycloaliphatic residue, in each case unsubstituted or mono- or polysubstituted with at least one substituent selected from the group consisting of F, Cl, Br, I, =O, OH, a $C_{1-4}$-aliphatic residue and an $O-C_{1-4}$-aliphatic residue, wherein the $C_{1-4}$-aliphatic residue may in each case may be unsubstituted or mono- or polysubstituted with at least one substituent selected from the group consisting of F, Cl, Br, I, =O, OH, and an unsubstituted $O-C_{1-4}$-aliphatic residue, and wherein the $C_{3-6}$-cycloaliphatic residue or the 3 to 6 membered heterocycloaliphatic residue may in each case be optionally bridged via a $C_{1-4}$ aliphatic group, which in turn may be unsubstituted or mono- or polysubstituted with at least one substituent selected from the group consisting of F, Cl, Br, I, OH, an unsubstituted $C_{1-4}$-aliphatic residue and an unsubstituted $O-C_{1-4}$-aliphatic residue, $R^3$, $R^4$, $R^5$ and $R^6$ each independently of one another represent H; F; Cl; Br; I; CN; $CF_3$; $OCF_3$; $SCF_3$; $C(=O)H$; $C(=O)-OH$; $C(=O)-NH_2$; $S(=O)_2-OH$; $NO_2$; a $C_{1-4}$-aliphatic residue, a $C(=O)-C_{1-4}$ aliphatic residue, a $C(=O)-O-C_{1-4}$ aliphatic residue, a $C(=O)-NH-C_{1-4}$ aliphatic residue, a $C(=O)-N(C_{1-4}$ aliphatic residue)$_2$, a $O-C_{1-4}$-aliphatic residue, a $O-C(=O)-C_{1-4}$-aliphatic residue, a $S-C_{1-4}$-aliphatic residue, a $S(=O)_2-C_{1-4}$-aliphatic residue, a $NH(C_{1-4}$ aliphatic residue), a $N(C_{1-4}$ aliphatic residue)$_2$, a $NH-C(=O)-C_{1-4}$ aliphatic residue, and a $NH-S(=O)_2-C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, and a $O-C_{1-4}$-aliphatic residue; a $C_{3-6}$-cycloaliphatic residue or a 3 to 6 membered heterocycloaliphatic residue, in each case unsubstituted or mono- or polysubstituted with at least one substituent selected from the group consisting of F, Cl, Br, I, OH, a $C_{1-4}$-aliphatic residue and a $O-C_{1-4}$-aliphatic residue, and in each case optionally bridged via an unsubstituted $C_{1-4}$ aliphatic group, preferably on the condition that at least one of $R^3$, $R^4$, $R^5$ and $R^6$ is ≠H, $R^7$ denotes a $C_{1-10}$-aliphatic residue, preferably a $C_{1-8}$-aliphatic residue, unsubstituted or mono- or polysubstituted with at least one substituent selected from the group consisting of F, Cl, Br, I, $NO_2$, $NH_2$, an $NH(C_{1-4}$ aliphatic residue), OH, an $O-C_{1-4}$-aliphatic residue, $OCF_3$, SH, $SCF_3$, a $S-C_{1-4}$-aliphatic residue, $CF_3$, CN, a $C_{1-4}$-aliphatic residue, a $C(=O)-O-C_{1-4}$-aliphatic residue and $C(=O)-OH$, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted $O-C_{1-4}$-aliphatic residue, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an $O-C_{1-4}$ aliphatic residue, $OCF_3$, SH, $SCF_3$, a $S-C_{1-4}$ aliphatic residue, $CF_3$, CN, a $C_{1-4}$-aliphatic residue, $C(=O)-OH$, a $C_{3-6}$ cycloaliphatic residue, and a 3 to 6 membered heterocycloaliphatic residue, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted $O-C_{1-4}$-aliphatic residue, and wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue and C(=O)—OH, and wherein the C$_{3-10}$-cycloaliphatic residue or the 3 to 10 membered heterocycloaliphatic residue may in each case optionally bridged via a C$_{1-8}$ aliphatic group, preferably a C$_{1-4}$ aliphatic group, which in turn may be unsubstituted or mono- or polysubstituted with at least one substituent selected from the group consisting of F, Cl, Br, I, NO$_2$, NH$_2$, an NH(C$_{1-4}$ aliphatic residue), OH, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue and C(=O)—OH, on the condition that if R$^7$ denotes a 3 to 10 membered heterocycloaliphatic residue, the 3 to 10 membered heterocycloaliphatic residue is linked via a carbon atom.

In a preferred embodiment of the compound according to general formula (I), the residue R$^1$ denotes a C$_{1-10}$-aliphatic residue, preferably a C$_{1-8}$-aliphatic residue, unsubstituted or mono- or polysubstituted with at least one substituent selected from the group consisting of F, Cl, Br, I, NO$_2$, NH$_2$, an NH(C$_{1-4}$ aliphatic residue), OH, an O—C$_{1-4}$-aliphatic residue, OCF$_3$, SH, SCF$_3$, a S—C$_{1-4}$-aliphatic residue, CF$_3$, CN, a C$_{1-4}$-aliphatic residue and C(=O)—OH,
wherein the C$_{1-4}$-aliphatic residue in each case may be unsubstituted or mono- or polysubstituted with at least one substituent selected from the group consisting of F, Cl, Br, I, OH, OCF$_3$, CF$_3$ and an unsubstituted O—C$_{1-4}$-aliphatic residue, or denotes a C$_{3-10}$-cycloaliphatic residue or a 3 to 10 membered heterocycloaliphatic residue, in each case unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue, C(=O)—OH, a C$_{3-6}$ cycloaliphatic residue, and a 3 to 6 membered heterocycloaliphatic residue,
wherein the C$_{1-4}$-aliphatic residue in each case may be unsubstituted or mono- or polysubstituted with at least one substituent selected from the group consisting of F, Cl, Br, I, OH, OCF$_3$, CF$_3$ and an unsubstituted O—C$_{1-4}$-aliphatic residue, and
wherein the C$_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue and C(=O)—OH,
and wherein the C$_{3-10}$-cycloaliphatic residue or the 3 to 10 membered heterocycloaliphatic residue may in each case optionally bridged via a C$_{1-8}$ aliphatic group, preferably a C$_{1-4}$ aliphatic group, which in turn may be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue and C(=O)—OH, or denotes an aryl or heteroaryl, in each case unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue, C(=O)—OH, C(=O)—CH$_3$, C(=O)—C$_2$H$_5$, C(=O)—O—CH$_3$ and C(=O)—O—C$_2$H$_5$, a C$_{3-6}$ cycloaliphatic residue, a 3 to 6 membered heterocycloaliphatic residue,

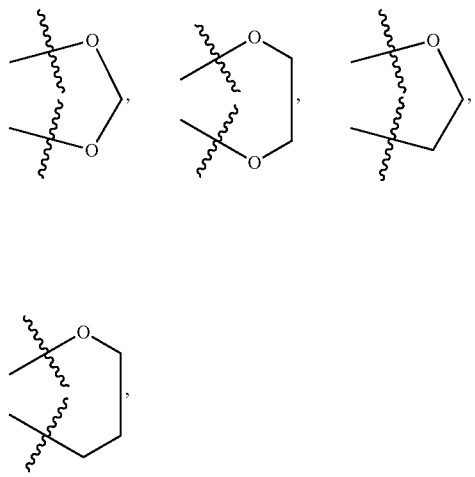

benzyl, phenyl, thienyl, pyridyl, furyl, thiazolyl and oxazolyl,
wherein the C$_{1-4}$-aliphatic residue in each case may be unsubstituted or mono- or polysubstituted with at least one substituent selected from the group consisting of F, Cl, Br, I, OH, OCF$_3$, CF$_3$ and an unsubstituted O—C$_{1-4}$-aliphatic residue, and wherein benzyl, phenyl, thienyl, pyridyl, furyl, thiazolyl and oxazolyl may in each case may be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, an O—C$_{1-4}$ aliphatic residue, OCF$_3$, O—CH$_2$—OH, O—CH$_2$—O—CH$_3$, SH, SCF$_3$, a S—C$_{1-4}$ aliphatic residue, CF$_3$, CN, a C$_{1-4}$-aliphatic residue, C(=O)—OH, C(=O)—CH$_3$, C(=O)—C$_2$H$_5$, C(=O)—O—CH$_3$ and C(=O)—O—C$_2$H$_5$, and wherein the C$_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue and C(=O)—OH, and wherein the aryl or the heteroaryl residue may in each case be optionally bridged via a C$_{1-8}$ aliphatic group, preferably a C$_{1-4}$ aliphatic group, which in turn may be unsubstituted or mono- or polysubstituted with at least one substituent selected from the group consisting of F, Cl, Br, I, NO$_2$, NH$_2$, an NH(C$_{1-4}$ aliphatic residue), OH, an O—C$_{1-4}$ aliphatic residue, OCF$_3$, SH, SCF$_3$, a S—C$_{1-4}$ aliphatic residue, CF$_3$, CN and C(=O)—OH.

In a further preferred embodiment of the compound according to general formula (I), the residue $R^1$ represents the partial structure (T1)

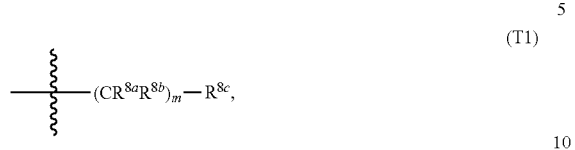

(T1)

wherein m denotes 0, 1, 2, 3 or 4, preferably denotes 0, 1, or 2, $R^{8a}$ and $R^{8b}$ each independently of one another represent H, F, Cl, Br, I, $NO_2$, $NH_2$, a $NH(C_{1-4}$ aliphatic residue), OH, an $O—C_{1-4}$ aliphatic residue, $OCF_3$, SH, $SCF_3$, a $S—C_{1-4}$ aliphatic residue, $CF_3$, CN, a $C_{1-4}$ aliphatic residue or C(=O)—OH, preferably each independently of one another represent H, F, Cl, Br, I, $NH_2$, a $NH(C_{1-4}$ aliphatic residue), OH, O—$C_{1-4}$ aliphatic residue or a $C_{1-4}$ aliphatic residue, more preferably each independently of one another represent H, F, Cl, Br, I, an O—$C_{1-4}$ aliphatic residue or a $C_{1-4}$ aliphatic residue, even more preferably each independently of one another represent H, F, an O—$C_{1-4}$ aliphatic residue or a $C_{1-4}$ aliphatic residue, and $R^{8c}$ denotes a $C_{1-4}$ aliphatic residue, unsubstituted or mono- or polysubstituted with at least one substituent selected from the group consisting of F, Cl, Br, I, $NO_2$, $NH_2$, an $NH(C_{1-4}$ aliphatic residue), OH, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH, or denotes a $C_{3-10}$-cycloaliphatic residue or a 3 to 10 membered heterocycloaliphatic residue, preferably when m is ≠0, in each case unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, C(=O)—OH, a $C_{3-6}$ cycloaliphatic residue and a 3 to 6 membered heterocycloaliphatic residue, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH, or denotes—preferably when m is =0—an aryl or heteroaryl, in each case unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, C(=O)—OH, C(=O)—$CH_3$, C(=O)—$C_2H_5$, C(=O)—O—$CH_3$ and C(=O)—O—$C_2H_5$, a $C_{3-6}$ cycloaliphatic residue, a 3 to 6 membered heterocycloaliphatic residue,

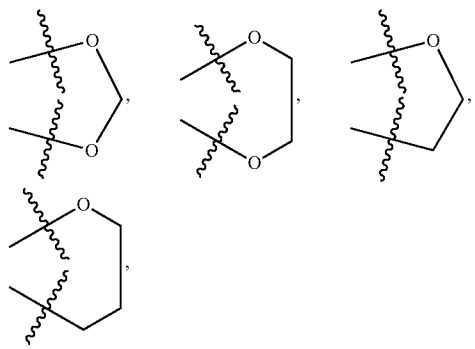

benzyl, phenyl, thienyl, pyridyl, furyl, thiazolyl and oxazolyl, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and wherein benzyl, phenyl, thienyl, pyridyl, furyl, thiazolyl and oxazolyl may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, C(=O)—OH, C(=O)—$CH_3$, C(=O)—$C_2H_5$, C(=O)—O—$CH_3$ and C(=O)—O—$C_2H_5$, and wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH.

Preferably, $R^1$ represents the partial structure (T1), wherein m denotes 0, 1, or 2, $R^{8a}$ and $R^{8b}$ each independently of one another represent H, F, Cl, Br, I, an O—$C_{1-4}$ aliphatic residue or a $C_{1-4}$ aliphatic residue, preferably each independently of one another represent H, F, a O—$C_{1-2}$ aliphatic residue or a $C_{1-2}$ aliphatic residue, and $R^{8c}$ denotes a $C_{1-4}$ aliphatic residue, unsubstituted or mono- or polysubstituted with at least one substituent selected from the group consisting of F, Cl, Br, I, OH, an O—$C_{1-4}$ aliphatic residue, $OCF_3$, $CF_3$, a $C_{1-4}$-aliphatic residue and C(=O)—OH, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, OH, =O, an O—$C_{1-4}$ aliphatic residue, OCF$_3$, CF$_3$, a C$_{1-4}$-aliphatic residue, C(=O)—OH, a C$_{3-6}$ cycloaliphatic residue, and a 3 to 6 membered heterocycloaliphatic residue,
  wherein the C$_{1-4}$-aliphatic residue in each case may be unsubstituted or mono- or polysubstituted with at least one substituent selected from the group consisting of F, Cl, Br, I, OH, OCF$_3$, CF$_3$ and an unsubstituted O—C$_{1-4}$-aliphatic residue, and
  wherein the C$_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, OH, =O, an O—C$_{1-4}$ aliphatic residue, OCF$_3$, CF$_3$, a C$_{1-4}$-aliphatic residue and C(=O)—OH,
or denotes—preferably when m is =0—an aryl or heteroaryl, in each case unsubstituted or mono- or polysubstituted with at least one substituent selected from the group consisting of F, Cl, Br, I, OH, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue, C(=O)—OH, C(=O)—CH$_3$, C(=O)—C$_2$H$_5$, C(=O)—O—CH$_3$ and C(=O)—O—C$_2$H$_5$, a C$_{3-6}$ cycloaliphatic residue, a 3 to 6 membered heterocycloaliphatic residue, benzyl, phenyl, thienyl, pyridyl, furyl, thiazolyl or oxazolyl,
  wherein the C$_{1-4}$-aliphatic residue in each case may be unsubstituted or mono- or polysubstituted with at least one substituent selected from the group consisting of F, Cl, Br, I, OH, OCF$_3$, CF$_3$ and an unsubstituted O—C$_{1-4}$-aliphatic residue, and
  wherein benzyl, phenyl, thienyl, pyridyl, furyl, thiazolyl and oxazolyl may in each case may be unsubstituted or mono- or polysubstituted, preferably unsubstituted or mono- or disubstituted with at least one substituent selected from the group consisting of F, Cl, Br, I, OH, an O—C$_{1-4}$ aliphatic residue, OCF$_3$, CF$_3$, CN, a C$_{1-4}$-aliphatic residue, C(=O)—OH, C(=O)—CH$_3$, C(=O)—C$_2$H$_5$, C(=O)—O—CH$_3$ and C(=O)—O—C$_2$H$_5$, preferably with at least one substituent selected from the group consisting of F, Cl, CH$_3$, O—CH$_3$, CF$_3$ and OCF$_3$,
  wherein the C$_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, OH, =O, an O—C$_{1-4}$ aliphatic residue, OCF$_3$, CF$_3$ a C$_{1-4}$-aliphatic residue and C(=O)—OH.

More preferably,
R$^1$ represents the partial structure (T1),
wherein
m denotes 0, 1, or 2,
R$^{8a}$ and R$^{8b}$ each independently of one another represent H, F, Cl, Br, I, an O—C$_{1-4}$ aliphatic residue or a C$_{1-4}$ aliphatic residue,
  preferably each independently of one another represent H, F, a O—C$_{1-2}$ aliphatic residue or a C$_{1-2}$ aliphatic residue, and
R$^{8c}$ denotes a C$_{1-4}$ aliphatic residue, unsubstituted or mono- or polysubstituted with at least one substituent selected from the group consisting of F, Cl, Br, I, an O—C$_{1-4}$ aliphatic residue, CF$_3$, and a C$_{1-4}$-aliphatic residue,
  wherein the C$_{1-4}$-aliphatic residue in each case may be unsubstituted or mono- or polysubstituted with at least one substituent selected from the group consisting of F, Cl, CF$_3$ and an unsubstituted O—C$_{1-4}$-aliphatic residue,
  or denotes a C$_{3-10}$-cycloaliphatic residue or a 3 to 10 membered heterocycloaliphatic residue, in each case unsubstituted or mono- or polysubstituted with at least one substituent selected from the group consisting of F, Cl, Br, I, an O—C$_{1-4}$ aliphatic residue, CF$_3$, and a C$_{1-4}$-aliphatic residue,
  wherein the C$_{1-4}$-aliphatic residue in each case may be unsubstituted or mono- or polysubstituted with at least one substituent selected from the group consisting of F, Cl, CF$_3$ and an unsubstituted O—C$_{1-4}$-aliphatic residue,
  or denotes—preferably when m is =0—an aryl or heteroaryl, in each case unsubstituted or mono- or polysubstituted with at least one substituent selected from the group consisting of F, Cl, Br, I, OH, an O—C$_{1-4}$ aliphatic residue, OCF$_3$, CF$_3$, CN, a C$_{1-4}$-aliphatic residue, C(=O)—CH$_3$, C(=O)—C$_2$H$_5$, C(=O)—O—CH$_3$ and C(=O)—O—C$_2$H$_5$, a C$_{3-6}$ cycloaliphatic residue, a 3 to 6 membered heterocycloaliphatic residue, benzyl, phenyl, thienyl or pyridyl,
  wherein benzyl, phenyl, thienyl and pyridyl, may in each case may be unsubstituted or mono- or polysubstituted, preferably unsubstituted or mono- or disubstituted with at least one substituent selected from the group consisting of F, Cl, Br, I, OH, an O—C$_{1-4}$ aliphatic residue, OCF$_3$, CF$_3$, CN, a C$_{1-4}$-aliphatic residue, C(=O)—CH$_3$, C(=O)—C$_2$H$_5$, C(=O)—O—CH$_3$ and C(=O)—O—C$_2$H$_5$, preferably with at least one substituent selected from the group consisting of F, Cl, CH$_3$, O—CH$_3$, CF$_3$ and OCF$_3$, and
  wherein the C$_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, OH, =O, an O—C$_{1-4}$ aliphatic residue, OCF$_3$, CF$_3$ a C$_{1-4}$-aliphatic residue and C(=O)—OH.

In a further preferred embodiment of the compound according to general formula (I), the residue
R$^1$ represents the partial structure (T1), wherein
m is 0, 1 or 2 and
R$^{8a}$ and R$^{8b}$ each independently of one another represent H, F, a O—C$_{1-4}$ aliphatic residue or a C$_{1-4}$ aliphatic residue; preferably H, F, CH$_3$ or OCH$_3$;
R$^{8c}$ denotes a C$_{1-4}$ aliphatic residue, unsubstituted or mono- or polysubstituted with at least one substituent selected from the group consisting of F, Cl, Br, I, an unsubstituted O—C$_{1-4}$ aliphatic residue, CF$_3$, and an unsubstituted C$_{1-4}$-aliphatic residue,
  or denotes a C$_{3-10}$-cycloaliphatic residue or a 3 to 10 membered heterocycloaliphatic residue, in each case unsubstituted or mono- or polysubstituted with at least one substituent selected from the group consisting of F, Cl, Br, I, an unsubstituted O—C$_{1-4}$ aliphatic residue, CF$_3$, and an unsubstituted C$_{1-4}$-aliphatic residue,
or
wherein
m is 0,
R$^{8a}$ and R$^{8b}$ each independently of one another represent H, F, a O—C$_{1-4}$ aliphatic residue or a C$_{1-4}$ aliphatic residue; preferably H, F, CH$_3$ or OCH$_3$; and
R$^{8c}$ denotes an aryl or heteroaryl, in each case unsubstituted or mono- or polysubstituted with at least one substituent selected from the group consisting of F, Cl, Br, I, OH, an O—$C_{1-4}$ aliphatic residue, $OCF_3$, $CF_3$, CN, a $C_{1-4}$-aliphatic residue, C(=O)—$CH_3$, C(=O)—$C_2H_5$, C(=O)—O—$CH_3$, C(=O)—O—$C_2H_5$ and phenyl, wherein phenyl may be unsubstituted or mono- or polysubstituted, preferably unsubstituted or mono- or disubstituted with at least one substituent selected from the group consisting of F, Cl, Br, I, OH, an O—$C_{1-4}$ aliphatic residue, $OCF_3$, $CF_3$, CN, a $C_{1-4}$-aliphatic residue, C(=O)—$CH_3$, C(=O)—$C_2H_5$, C(=O)—O—$CH_3$ and C(=O)—O—$C_2H_5$, preferably with at least one substituent selected from the group consisting of F, Cl, $CH_3$, O—$CH_3$, $CF_3$ and $OCF_3$.

Particularly preferred is a compound according to general formula (I) which has the following general formula (Ie):

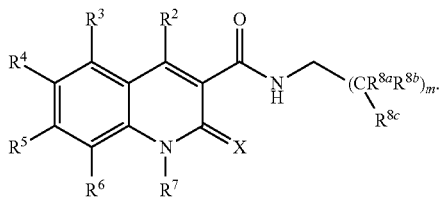

In particular, $R^1$ represents aryl, preferably phenyl, or heteroaryl, preferably pyridyl or thienyl, in each case unsubstituted or mono- or disubstituted with at least one substituent selected from the group consisting of F, Cl, Br, I, OH, $OCH_3$, $OCF_3$, $CF_3$, CN, and $CH_3$, preferably represents phenyl, unsubstituted or mono- or disubstituted with at least one substituent selected from the group consisting of F, Cl, Br, I, OH, $OCH_3$, $OCF_3$, $CF_3$, CN, and $CH_3$, or represents an unsubstituted $C_{1-6}$-aliphatic residue.

In a further preferred embodiment of the compound according to general formula (I), the residue X denotes O.

In another preferred embodiment of the compound according to general formula (I), the residue X denotes S.

In a preferred embodiment of the compound according to general formula (I), the residue $R^2$ represents F; Cl; Br; I; CN; $CF_3$; $NO_2$; $OCF_3$; $SCF_3$; a $C_{1-4}$-aliphatic residue, a S—$C_{1-4}$-aliphatic residue, a O—$C_{1-4}$-aliphatic residue, wherein the $C_{1-4}$ aliphatic residue may be in each case be unsubstituted or mono- or polysubstituted; a $C_{3-6}$-cycloaliphatic residue or a 3 to 6 membered heterocycloaliphatic residue, in each case unsubstituted or mono- or polysubstituted and in each case optionally bridged via a $C_{1-4}$ aliphatic group, which in turn may be unsubstituted or mono- or polysubstituted.

Preferably, $R^2$ represents F; Cl; Br; I; CN; $CF_3$; $NO_2$; $OCF_3$; $SCF_3$; a $C_{1-4}$-aliphatic residue, a S—$C_{1-4}$-aliphatic residue, a O—$C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, and an unsubstituted O—$C_{1-4}$-aliphatic residue, a $C_{3-6}$-cycloaliphatic residue or a 3 to 6 membered heterocycloaliphatic residue, in each case unsubstituted or mono- or polysubstituted with at least one substituent selected from the group consisting of F, Cl, Br, I, =O, OH, a $C_{1-4}$-aliphatic residue and a O—$C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, and an unsubstituted O—$C_{1-4}$-aliphatic residue, and wherein the $C_{3-6}$-cycloaliphatic residue or the 3 to 6 membered heterocycloaliphatic residue may in each case be optionally bridged via a $C_{1-4}$ aliphatic group, which in turn may be unsubstituted or mono- or polysubstituted with at least one substituent selected from the group consisting of F, Cl, Br, I, =O, OH, an unsubstituted $C_{1-4}$-aliphatic residue and an unsubstituted O—$C_{1-4}$-aliphatic residue.

More preferably, $R^2$ represents F; Cl; Br; I; CN; $CF_3$; $NO_2$; $OCF_3$; $SCF_3$; a $C_{1-4}$-aliphatic residue, a S—$C_{1-4}$-aliphatic residue, or a O—$C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, and an unsubstituted O—$C_{1-4}$-aliphatic residue, cyclopropyl, cyclobutyl, cyclopentyl, cyclohexyl, pyrrolidinyl, piperazinyl, 4-methylpiperazinyl, morpholinyl, or piperidinyl, preferably cyclopropyl, cyclobutyl, cyclopentyl or cyclohexyl, in each case unsubstituted or mono- or polysubstituted with at least one substituent selected from the group consisting of F, Cl, Br, I, =O, OH, an unsubstituted $C_{1-4}$-aliphatic residue and an unsubstituted O—$C_{1-4}$-aliphatic residue, and wherein cyclopropyl, cyclobutyl, cyclopentyl, cyclohexyl, pyrrolidinyl, piperazinyl, 4-methylpiperazinyl, morpholinyl or piperidinyl may in each case be optionally bridged via an $C_{1-4}$ aliphatic group, which in turn may be unsubstituted or mono- or polysubstituted with at least one substituent selected from the group consisting of F, Cl, OH, an unsubstituted $C_{1-4}$-aliphatic residue and an unsubstituted O—$C_{1-4}$-aliphatic residue.

Even more preferably, $R^2$ represents F; Cl; Br; I; CN; $CF_3$; $NO_2$; $OCF_3$; $SCF_3$; methyl; ethyl; n-propyl; iso-propyl; n-butyl; sec.-butyl; tert.-butyl; O-methyl; O-ethyl; O—$(CH_2)_2$—O—$CH_3$; O—$(CH_2)_2$—OH; S-Methyl; S-Ethyl; cyclopropyl, cyclobutyl, cyclopentyl, and cyclohexyl.

Still more preferably, $R^2$ is selected from the group consisting of F; Cl; Br; $CF_3$; CN; $SCF_3$; $OCF_3$; $CH_3$; $C_2H_5$; n-propyl; iso-propyl; t-butyl; cyclopropyl; O—$CH_3$ and O—$C_2H_5$.

In particular, $R^2$ is selected from the group consisting of F; Cl; Br; $CF_3$; $CH_3$; $C_2H_5$, iso-propyl; cyclopropyl; and O—$CH_3$.

In a preferred embodiment of the compound according to general formula (I), the residues $R^3$, $R^4$, $R^5$ and $R^6$ each independently of one another represent H; F; Cl; Br; I; CN; $CF_3$; $OCF_3$; $SCF_3$; C(=O)H; C(=O)—OH; C(=O)—$NH_2$; S(=O)$_2$—OH; $NO_2$; a $C_{1-4}$-aliphatic residue, a C(=O)—$C_{1-4}$ aliphatic residue, a C(=O)—O—$C_{1-4}$ aliphatic residue, a C(=O)—NH—$C_{1-4}$ aliphatic residue, a C(=O)—N($C_{1-4}$ aliphatic residue)$_2$, a O—$C_{1-4}$-aliphatic residue, a O—C(=O)—$C_{1-4}$-aliphatic residue, a S—$C_{1-4}$-aliphatic residue, a S(=O)$_2$—$C_{1-4}$-aliphatic residue, a NH($C_{1-4}$ aliphatic residue), a N($C_{1-4}$ aliphatic residue)$_2$, a NH—C(=O)—$C_{1-4}$ aliphatic residue, and a NH—S(=O)$_2$—$C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, and a O—$C_{1-4}$-aliphatic residue; a $C_{3-6}$-cycloaliphatic residue or a 3 to 6 membered heterocycloaliphatic residue, in each case unsubstituted or mono- or polysubstituted with at least one substituent selected from the group consisting of F, Cl, Br, I, =O, OH, a $C_{1-4}$-aliphatic residue and a O—$C_{1-4}$-aliphatic residue, and in each case optionally bridged via an unsubstituted $C_{1-4}$ aliphatic group, preferably on the condition that at least one of $R^3$, $R^4$, $R^5$ and $R^6$ is ≠H.

Preferably, $R^3$, $R^4$, $R^5$ and $R^6$ each independently of one another represent H; F; Cl; Br; I; CN; $CF_3$; $OCF_3$; $SCF_3$; C(=O)H; C(=O)—OH; C(=O)—$NH_2$; $S(=O)_2$—OH; $NO_2$; a $C_{1-4}$-aliphatic residue, a C(=O)—$C_{1-4}$ aliphatic residue, a C(=O)—O—$C_{1-4}$ aliphatic residue, a O—$C_{1-4}$-aliphatic residue, a O—C(=O)—$C_{1-4}$-aliphatic residue, a S—$C_{1-4}$-aliphatic residue, a $S(=O)_2$—$C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, and a O—$C_{1-4}$-aliphatic residue; a $C_{3-6}$-cycloaliphatic residue or a 3 to 6 membered heterocycloaliphatic residue, in each case unsubstituted or mono- or polysubstituted with at least one substituent selected from the group consisting of F, Cl, Br, I, =O, OH, a $C_{1-4}$-aliphatic residue and a O—$C_{1-4}$-aliphatic residue, and in each case optionally bridged via an unsubstituted $C_{1-4}$ aliphatic group, preferably on the condition that at least one of $R^3$, $R^4$, $R^5$ and $R^6$ is ≠H.

More preferably, $R^3$, $R^4$, $R^5$ and $R^6$ each independently of one another represent H; F; Cl; Br; I; CN; $CF_3$; $OCF_3$; $SCF_3$; C(=O)H; $NO_2$; a $C_{1-4}$-aliphatic residue, a C(=O)—$C_{1-4}$ aliphatic residue, a C(=O)—O—$C_{1-4}$ aliphatic residue, a O—$C_{1-4}$-aliphatic residue, a S—$C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, and a O—$C_{1-4}$-aliphatic residue; a $C_{3-6}$-cycloaliphatic residue, unsubstituted or mono- or polysubstituted with at least one substituent selected from the group consisting of F, Cl, Br, I, =O, OH, a $C_{1-4}$-aliphatic residue and a O—$C_{1-4}$-aliphatic residue, and in each case optionally bridged via an unsubstituted $C_{1-4}$ aliphatic group, preferably on the condition that at least one of $R^3$, $R^4$, $R^5$ and $R^6$ is ≠H.

In a further preferred embodiment of the present invention $R^3$, $R^4$, $R^5$ and $R^6$ each independently of one another are selected from the group consisting of H; F; Cl; Br; I; $NO_2$; $CF_3$; CN; $OCF_3$; $SCF_3$; a (C=O)—$C_{1-4}$ aliphatic residue, a $C_{1-4}$ aliphatic residue, O—$C_{1-4}$ aliphatic residue, a S-$C_{1-4}$ aliphatic residue, wherein the $C_{1-4}$-aliphatic residue in each case may be unsubstituted or mono- or polysubstituted with at least one substituent selected from the group consisting of F, Cl, OH, and O—$CH_3$;

preferably on the condition that at least one of $R^3$, $R^4$, $R^5$ and $R^6$ is ≠H.

Preferably, $R^3$, $R^4$, $R^5$ and $R^6$ each independently of one another are selected from the group consisting of H; F; Cl; Br; I; $NO_2$; $CF_3$; CN; $OCF_3$; $SCF_3$; methyl; ethyl; n-propyl; iso-propyl; n-butyl; sec.-butyl; tert.-butyl; cyclopropyl; C(=O)-methyl; (C=O)-ethyl; (C=O)-isopropyl; (C=O)-t-butyl; O-methyl; O-ethyl; O-isopropyl; O-t-butyl; O—$(CH_2)_2$—O—$CH_3$; S-Methyl; S-Ethyl;

preferably on the condition that at least one of $R^3$, $R^4$, $R^5$ and $R^6$ is ≠H.

In particular, $R^3$, $R^4$, $R^5$ and $R^6$ are each independently of one another are selected from the group consisting of H; F; Cl; Br; I; $NO_2$; $CF_3$; CN; (C=O)-methyl; (C=O)-ethyl; (C=O)-isopropyl; (C=O)-t-butyl; methyl; ethyl; isopropyl; t-butyl; O-methyl; O-Ethyl; O-isopropyl; O-t-butyl; $OCF_3$; S-methyl; S-ethyl; and $SCF_3$;

preferably on the condition that at least one of $R^3$, $R^4$, $R^5$ and $R^6$ is ≠H.

More particularly, $R^3$, $R^4$, $R^5$ and $R^6$ are each independently of one another selected from the group consisting of H; F; Cl; Br; $CF_3$; CN; $OCF_3$ and $NO_2$;

preferably on the condition that at least one of $R^3$, $R^4$, $R^5$ and $R^6$ is ≠H.

Most preferred, $R^3$, $R^4$ and $R^6$ each independently of one another represent H or F, preferably each denotes H; and $R^5$ denotes H; F; Cl; Br; $CF_3$; $OCF_3$; CN; or $NO_2$; preferably denotes F; Cl; Br; $CF_3$; $OCF_3$; or CN.

In a particular preferred embodiment of the compound according to general formula (I)

at least one of the residues $R^3$, $R^4$, $R^5$ and $R^6$ is ≠H.

In another particular preferred embodiment of the compound according to general formula (I)

at least two of the residues $R^3$, $R^4$, $R^5$ and $R^6$ denote H, preferably at least two of $R^3$, $R^4$ and $R^6$ denote H.

In a preferred embodiment of the compound according to general formula (I), the residue $R^7$ denotes a $C_{1-10}$-aliphatic residue, preferably a $C_{1-8}$-aliphatic residue, unsubstituted or mono- or polysubstituted with at least one substituent selected from the group consisting of F, Cl, Br, I, $NO_2$, $NH_2$, an NH($C_{1-4}$ aliphatic residue), OH, an O—$C_{1-4}$-aliphatic residue, $OCF_3$, SH, $SCF_3$, a S—$C_{1-4}$-aliphatic residue, $CF_3$, CN, a $C_{1-4}$-aliphatic residue, a C(=O)—O—$C_{1-4}$-aliphatic residue, and C(=O)—OH, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, $NO_2$, $NH_2$, an NH($C_{1-4}$ aliphatic residue), an N($C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, C(=O)—OH, a C(=O)—O—$C_{1-4}$-aliphatic residue a $C_{3-6}$ cycloaliphatic residue, and a 3 to 6 membered heterocycloaliphatic residue, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, $NH_2$, an NH($C_{1-4}$ aliphatic residue), an N($C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH, and wherein the $C_{3-10}$-cycloaliphatic residue or the 3 to 10 membered heterocycloaliphatic residue may in each case optionally bridged via a $C_{1-8}$ aliphatic group, preferably a $C_{1-4}$ aliphatic group, which in turn may be unsubstituted or mono- or polysubstituted with at least one substituent selected from the group consisting of F, Cl, Br, I, $NO_2$, $NH_2$, an NH($C_{1-4}$ aliphatic residue), an N($C_{1-4}$ aliphatic residue)$_2$, OH, =O, an O—$C_{1-4}$ aliphatic residue, a C(=O)—O—$C_{1-4}$-aliphatic residue, $OCF_3$, SH, $SCF_3$, a S—$C_{1-4}$ aliphatic residue, $CF_3$, CN, a $C_{1-4}$-aliphatic residue and C(=O)—OH, on the condition that if $R^7$ denotes a 3 to 10 membered heterocycloaliphatic residue, the 3 to 10 membered heterocycloaliphatic residue is linked via a carbon atom.

In a further preferred embodiment of the compound according to general formula (I), the residue $R^7$ denotes a $C_{1-10}$-aliphatic residue, preferably a $C_{1-8}$-aliphatic residue, unsubstituted or mono- or polysubstituted with at least one substituent selected from the group consisting of F, Cl, Br, I, $NO_2$, OH, an O—$C_{1-4}$-aliphatic residue, $OCF_3$, SH, $SCF_3$, a S—$C_{1-4}$-aliphatic residue, a C(=O)—O—$C_{1-4}$-aliphatic residue, COOH, $CF_3$, CN, and a $C_{1-4}$-aliphatic residue wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, $NO_2$, OH, =O, an O—$C_{1-4}$ aliphatic residue, $OCF_3$, SH, $SCF_3$, a S—$C_{1-4}$ aliphatic residue, a C(=O)—O—$C_{1-4}$-aliphatic residue, $CF_3$, CN, a $C_{1-4}$-aliphatic residue, a $C_{3-6}$ cycloaliphatic residue, and a 3 to 6 membered heterocycloaliphatic residue, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, OH, =O, an O—$C_{1-4}$ aliphatic residue, $OCF_3$, SH, $SCF_3$, a S—$C_{1-4}$ aliphatic residue, $CF_3$, CN, and a $C_{1-4}$-aliphatic residue, and wherein the $C_{3-10}$-cycloaliphatic residue or the 3 to 10 membered heterocycloaliphatic residue may in each case be optionally bridged, preferably is bridged, via a $C_{1-8}$ aliphatic group, preferably a $C_{1-4}$ aliphatic group, which in turn may be unsubstituted or mono- or polysubstituted with at least one substituent selected from the group consisting of F, Cl, Br, I, $NO_2$, OH, =O, an O—$C_{1-4}$ aliphatic residue, a C(=O)—O—$C_{1-4}$-aliphatic residue, $OCF_3$, SH, $SCF_3$, a S—$C_{1-4}$ aliphatic residue, $CF_3$, CN, and a $C_{1-4}$-aliphatic residue, on the condition that if $R^7$ denotes a 3 to 10 membered heterocycloaliphatic residue, the 3 to 10 membered heterocycloaliphatic residue is linked via a carbon atom.

Preferably, $R^7$ denotes a $C_{1-8}$-aliphatic residue, unsubstituted or mono- or polysubstituted with at least one substituent selected from the group consisting of F, Cl, Br, I, OH, an O—$C_{1-4}$-aliphatic residue, $OCF_3$, SH, $SCF_3$, a S—$C_{1-4}$-aliphatic residue, a C(=O)—O—$C_{1-4}$-aliphatic residue, COOH, $CF_3$, and a $C_{1-4}$-aliphatic residue wherein the $C_{1-4}$-aliphatic residue in each case may be unsubstituted or mono- or polysubstituted with at least one substituent selected from the group consisting of F, Cl, Br, I, OH, $CF_3$ and an unsubstituted O—$C_{1-4}$-aliphatic residue, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, OH, =O, an O—$C_{1-4}$ aliphatic residue, $OCF_3$, $SCF_3$, a C(=O)—O—$C_{1-4}$-aliphatic residue, a S—$C_{1-4}$ aliphatic residue, $CF_3$, and a $C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and and wherein the $C_{3-10}$-cycloaliphatic residue or the 3 to 10 membered heterocycloaliphatic residue may in each case optionally bridged via a $C_{1-8}$ aliphatic group, preferably a $C_{1-4}$ aliphatic group, which in turn may be unsubstituted or mono- or polysubstituted with at least one substituent selected from the group consisting of F, Cl, Br, I, OH, =O, an O—$C_{1-4}$ aliphatic residue, $OCF_3$, SH, $SCF_3$, a S—$C_{1-4}$ aliphatic residue, a C(=O)—O—$C_{1-4}$-aliphatic residue, $CF_3$, CN, and a $C_{1-4}$-aliphatic residue, on the condition that if $R^7$ denotes a 3 to 10 membered heterocycloaliphatic residue, the 3 to 10 membered heterocycloaliphatic residue is linked via a carbon atom.

More preferably, $R^7$ denotes a $C_{1-8}$-aliphatic residue, preferably a $C_{1-6}$-aliphatic residue, unsubstituted or mono- or polysubstituted with at least one substituent selected from the group consisting of F, Cl, Br, I, OH, an O—$C_{1-4}$-aliphatic residue, $OCF_3$, SH, $SCF_3$, a S—$C_{1-4}$-aliphatic residue, COOH, $CF_3$, a C(=O)—O—$C_{1-4}$-aliphatic residue, and a $C_{1-4}$-aliphatic residue wherein the $C_{1-4}$-aliphatic residue in each case may be unsubstituted or mono- or polysubstituted with at least one substituent selected from the group consisting of F, Cl, Br, I, OH, $CF_3$ and an unsubstituted O—$C_{1-4}$-aliphatic residue, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, OH, =O, an O—$C_{1-4}$ aliphatic residue, $OCF_3$, $SCF_3$, a S—$C_{1-4}$ aliphatic residue, a C(=O)—O—$C_{1-4}$-aliphatic residue, $CF_3$, and a $C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and wherein the $C_{3-10}$-cycloaliphatic residue or the 3 to 10 membered heterocycloaliphatic residue in each case may be bridged, preferably is bridged, via a $C_{1-8}$ aliphatic group, preferably a $C_{1-4}$ aliphatic group, which in turn may be unsubstituted or mono- or polysubstituted with at least one substituent selected from the group consisting of F, Cl, Br, I, OH, =O, an O—$C_{1-4}$ aliphatic residue, $OCF_3$, SH, $SCF_3$, a S—$C_{1-4}$ aliphatic residue, a C(=O)—O—$C_{1-4}$-aliphatic residue, $CF_3$, CN, and a $C_{1-4}$-aliphatic residue, on the condition that if $R^7$ denotes a 3 to 10 membered heterocycloaliphatic residue, the 3 to 10 membered heterocycloaliphatic residue is linked via a carbon atom.

Even more preferably, $R^7$ denotes a $C_{1-8}$-aliphatic residue, preferably a $C_{1-6}$-aliphatic residue, unsubstituted or mono- or polysubstituted with at least one substituent selected from the group consisting of F, Cl, Br, I, OH, an O—$C_{1-4}$-aliphatic residue, $OCF_3$, SH, $SCF_3$, a S—$C_{1-4}$-aliphatic residue, COOH, a C(=O)—O—$C_{1-4}$-aliphatic residue, $CF_3$, and a $C_{1-4}$-aliphatic residue wherein the $C_{1-4}$-aliphatic residue in each case may be unsubstituted or mono- or polysubstituted with at least one substituent selected from the group consisting of F, Cl, Br, I, OH, $CF_3$ and an unsubstituted O—$C_{1-4}$-aliphatic residue, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, OH, =O, an O—$C_{1-4}$ aliphatic residue, $OCF_3$, $SCF_3$, a S—$C_{1-4}$ aliphatic residue, a C(=O)—O—$C_{1-4}$-aliphatic residue, $CF_3$, and a $C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and wherein the $C_{3-10}$-cycloaliphatic residue or the 3 to 10 membered heterocycloaliphatic residue may in each case be bridged, preferably is bridged, via a unsubstituted $C_{1-8}$ aliphatic group, preferably an unsubstituted $C_{1-4}$ aliphatic group, on the condition that if $R^7$ denotes a 3 to 10 membered heterocycloaliphatic residue, the 3 to 10 membered heterocycloaliphatic residue is linked via a carbon atom.

Still more preferably, $R^7$ denotes a $C_{1-6}$-aliphatic residue, unsubstituted or mono- or polysubstituted with at least one substituent selected from the group consisting of F, Cl, Br, I, OH, an O—$C_{1-4}$-aliphatic residue, COOH, a C(=O)—O—$C_{1-4}$-aliphatic residue, $OCF_3$, SH, $SCF_3$, a S—$C_{1-4}$-aliphatic residue, $CF_3$, and a $C_{1-4}$-aliphatic residue wherein the $C_{1-4}$-aliphatic residue in each case may be unsubstituted or mono- or polysubstituted with at least one substituent selected from the group consisting of F, OH, $CF_3$ and an unsubstituted O—$C_{1-4}$-aliphatic residue, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, OH, =O, an O—$C_{1-4}$ aliphatic residue, $OCF_3$, $SCF_3$, a S—$C_{1-4}$ aliphatic residue, a C(=O)—O—$C_{1-4}$-aliphatic residue, $CF_3$, and a $C_{1-4}$-aliphatic residue, wherein the $C_{1-4}$-aliphatic residue in each case may be unsubstituted or mono- or polysubstituted with OH or an unsubstituted O—$C_{1-4}$-aliphatic residue.

and wherein the $C_{3-10}$-cycloaliphatic residue or the 3 to 10 membered heterocycloaliphatic residue in each case may be bridged, preferably is bridged, via a unsubstituted $C_{1-4}$ aliphatic group, on the condition that if $R^7$ denotes a 3 to 10 membered heterocycloaliphatic residue, the 3 to 10 membered heterocycloaliphatic residue is linked via a carbon atom.

In particular, $R^7$ denotes a $C_{1-6}$-aliphatic residue, unsubstituted or mono- or polysubstituted with at least one substituent selected from the group consisting of F, Cl, Br, I, OH, an O—$C_{1-4}$-aliphatic residue, COOH, a C(=O)—O—$C_{1-4}$-aliphatic residue, $OCF_3$, SH, $SCF_3$, a S—$C_{1-4}$-aliphatic residue, $CF_3$, and a $C_{1-4}$-aliphatic residue, preferably unsubstituted or mono- or polysubstituted with at least one substituent selected from the group consisting of F, Cl, OH, an O—$C_{1-4}$-aliphatic residue, $OCF_3$, $CF_3$, and a $C_{1-4}$-aliphatic residue, wherein the $C_{1-4}$-aliphatic residue in each case may be unsubstituted or mono- or polysubstituted with at least one substituent selected from the group consisting of OH, and an unsubstituted O—$C_{1-4}$-aliphatic residue, or denotes a $C_{3-6}$-cycloaliphatic residue or a 3 to 6 membered heterocycloaliphatic residue, in each case unsubstituted or mono- or polysubstituted with at least one substituent selected from the group consisting of F, Cl, Br, I, OH, =O, an O—$C_{1-4}$ aliphatic residue, $OCF_3$, $SCF_3$, a S—$C_{1-4}$ aliphatic residue, a C(=O)—O—$C_{1-4}$-aliphatic residue, $CF_3$, and a $C_{1-4}$-aliphatic residue, on the condition that if $R^7$ denotes a 3 to 6 membered heterocycloaliphatic residue, the 3 to 6 membered heterocycloaliphatic residue is linked via a carbon atom.

Most preferred, $R^7$ denotes a $C_{1-6}$-aliphatic residue, unsubstituted or mono- or polysubstituted with at least one substituent selected from the group consisting of F, Cl, OH, a C(=O)—O—$C_{1-4}$-aliphatic residue, COOH and an O—$C_{1-4}$-aliphatic residue, preferably at least one substituent selected from the group consisting of OH, a C(=O)—O—$C_{1-4}$-aliphatic residue, COOH and an O—$C_{1-4}$-aliphatic residue, wherein the $C_{1-4}$-aliphatic residue in each case may be unsubstituted or mono- or polysubstituted with at least one substituent selected from the group consisting of OH, and an unsubstituted O—$C_{1-4}$-aliphatic residue, or denotes a $C_{3-6}$-cycloaliphatic residue or a 3 to 6 membered heterocycloaliphatic residue, in each case unsubstituted or mono- or polysubstituted with at least one substituent selected from the group consisting of F, Cl, Br, I, OH, =O, an O—$C_{1-4}$ aliphatic residue, a C(=O)—O—$C_{1-4}$-aliphatic residue, $CF_3$, and a $C_{1-4}$-aliphatic residue, on the condition that if $R^7$ denotes a 3 to 6 membered heterocycloaliphatic residue, the 3 to 6 membered heterocycloaliphatic residue is linked via a carbon atom.

In particular most preferred $R^7$ is selected from the group consisting of $CH_3$, $C_2H_5$, $C_3H_7$, $C_4H_9$, $C_5H_{11}$, $CH(CH_3)_2$, $C_2H_4$—$CH(CH_3)_2$, $C_3H_6$—$CH(CH_3)_2$, $CH_2OH$, $C_2H_4OH$, $CH_2$—$OCH_3$, $C_2H_4$—$OCH_3$, $C_3H_6$—$OCH_3$, $CH_2$—O—$C_2H_5$, $C_2H_4$—O—$C_2H_5$, $CH_2$—$CH(CH_3)(OCH_3)$, $CH_2$—$CH(C_2H_3)(OCH_3)$, $CH(CH_3)(CH_2$—$OCH_3)$, $CH(C_2H_4$—$OCH_3)_2$, $CH(C_2H_5)(CH_2$—$OCH_3)$, $C_2H_4$—O—$C_2H_4$—O—$CH_3$, $CH_2$—O—$C_2H_4$—O—$CH_3$, $C_2H_4$—O—$C_2H_4$—OH, $CH_2$—O—$C_2H_4$—OH, $CH_2$—C(=O)O—$CH_3$, $C_2H_4$—C(=O)$OCH_3$, $C_2H_4$—C(=O)OH, $CH_2$—C(=O)OH, or denotes an unsubstituted $C_{3-6}$-cycloaliphatic residue or an unsubstituted 3 to 6 membered heterocycloaliphatic residue, preferably tetrahydropyranyl or piperidinyl.

Particularly preferred is also a compound according to general formula (I), wherein
$R^1$ represents the partial structure (T1),

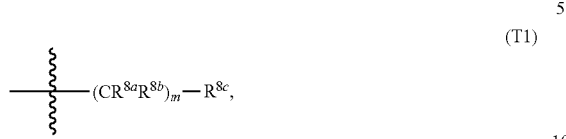

(T1)

wherein
m is 0, 1 or 2 and
$R^{8a}$ and $R^{8b}$ each independently of one another represent H, F, a O—$C_{1-4}$ aliphatic residue or a $C_{1-4}$ aliphatic residue; preferably H, F, $CH_3$ or $OCH_3$;
$R^{8c}$ denotes a $C_{1-4}$ aliphatic residue, unsubstituted or mono- or polysubstituted with at least one substituent selected from the group consisting of F, Cl, Br, I, an unsubstituted O—$C_{1-4}$ aliphatic residue, $CF_3$, and an unsubstituted $C_{1-4}$-aliphatic residue,
or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, an unsubstituted O—$C_{1-4}$ aliphatic residue, $CF_3$, and an unsubstituted $C_{1-4}$-aliphatic residue,
or
wherein
m is 0,
$R^{8a}$ and $R^{8b}$ each independently of one another represent H, F, a O—$C_{1-4}$ aliphatic residue or a $C_{1-4}$ aliphatic residue; preferably H, F, $CH_3$ or $OCH_3$; and
$R^{8c}$ denotes an aryl or heteroaryl, in each case unsubstituted or mono- or polysubstituted with at least one substituent selected from the group consisting of F, Cl, Br, I, OH, an O—$C_{1-4}$ aliphatic residue, $OCF_3$, $CF_3$, CN, a $C_{1-4}$-aliphatic residue, C(=O)—$CH_3$, C(=O)—$C_2H_5$, C(=O)—O—$CH_3$, C(=O)—O—$C_2H_5$ and phenyl,
wherein phenyl may be unsubstituted or mono- or polysubstituted, preferably unsubstituted or mono- or disubstituted with at least one substituent selected from the group consisting of F, Cl, Br, I, OH, an O—$C_{1-4}$ aliphatic residue, $OCF_3$, $CF_3$, CN, a $C_{1-4}$-aliphatic residue, C(=O)—$CH_3$, C(=O)—$C_2H_5$, C(=O)—O—$CH_3$ and C(=O)—O—$C_2H_5$, preferably with at least one substituent selected from the group consisting of F, Cl, $CH_3$, O—$CH_3$, $CF_3$ and $OCF_3$,
X represents O or S, preferably O;
$R^2$ is selected from the group consisting of F; Cl; Br; $CF_3$; $CH_3$; $C_2H_5$, iso-propyl; cyclopropyl; and O—$CH_3$;
$R^3$, $R^4$, $R^5$ and $R^6$ are each independently of one another selected from the group consisting of H; F; Cl; Br; $CF_3$; CN; $OCF_3$ and $NO_2$;
preferably on the condition that at least one of $R^3$, $R^4$, $R^5$ and $R^6$ is ≠H,
$R^7$ denotes a $C_{1-6}$-aliphatic residue, unsubstituted or mono- or polysubstituted with at least one substituent selected from the group consisting of F, Cl, Br, I, OH, an O—$C_{1-4}$-aliphatic residue, COOH, a C(=O)—O—$C_{1-4}$-aliphatic residue, $OCF_3$, SH, $SCF_3$, a S—$C_{1-4}$-aliphatic residue, $CF_3$, and a $C_{1-4}$-aliphatic residue, preferably unsubstituted or mono- or polysubstituted with at least one substituent selected from the group consisting of F, Cl, OH, an O—$C_{1-4}$-aliphatic residue, $OCF_3$, $CF_3$, and a $C_{1-4}$-aliphatic residue, wherein the $C_{1-4}$-aliphatic residue in each case may be unsubstituted or mono- or polysubstituted with at least one substituent selected from the group consisting of OH, and an unsubstituted O—$C_{1-4}$-aliphatic residue,
or denotes an unsubstituted $C_{3-6}$-cycloaliphatic residue or an unsubstituted 3 to 6 membered heterocycloaliphatic residue,
on the condition that if $R^7$ denotes a 3 to 6 membered heterocycloaliphatic residue, the 3 to 6 membered heterocycloaliphatic residue is linked via a carbon atom.

Particularly preferred is also a compound according to general formula (I), wherein
$R^1$ represents aryl, preferably phenyl, or heteroaryl, preferably pyridyl or thienyl, in each case unsubstituted or mono- or disubstituted with at least one substituent selected from the group consisting of F, Cl, Br, I, OH, $OCH_3$, $OCF_3$, $CF_3$, CN, and $CH_3$,
preferably represents phenyl, unsubstituted or mono- or disubstituted with at least one substituent selected from the group consisting of F, Cl, Br, I, OH, $OCH_3$, $OCF_3$, $CF_3$, CN, and $CH_3$;
X is O;
$R^2$ is selected from the group consisting of F, Cl, $CF_3$, $CH_3$, $C_2H_5$, iso-propyl, cyclopropyl, and O—$CH_3$; preferably is selected from the group consisting of $CH_3$, $C_2H_5$, $OCH_3$ and $CF_3$;
$R^3$, $R^4$, $R^5$ and $R^6$ are each independently of one another selected from the group consisting of H, F, Cl, Br, $CF_3$, CN, $OCF_3$ and $NO_2$;
preferably on the condition that at least one of $R^3$, $R^4$, $R^5$ and $R^6$ is ≠H, more preferably on the condition that $R^5$ is ≠H;
$R^7$ denotes a saturated $C_{1-6}$-aliphatic residue, unsubstituted or mono- or disubstituted with at least one substituent selected from the group consisting of F, Cl, Br, I, OH, O—$CH_3$, O—$C_2H_5$, $OCF_3$, $OC_2H_4$—O—$CH_3$, COOH, C(=O)$OCH_3$, $SCF_3$, and $CF_3$,
preferably denotes a saturated $C_{1-6}$-aliphatic residue, unsubstituted or mono- or disubstituted with at least one substituent selected from the group consisting of OH, O—$CH_3$, O—$C_2H_5$, $OCF_3$, $OC_2H_4$—O—$CH_3$, COOH, and C(=O)$OCH_3$.

Especially particularly preferred are compounds according to general formula (I) selected from the group comprising:
1  N-[(3-Fluorophenyl)-methyl]-1,4-dimethyl-2-oxo-7-(trifluoromethyl)-1H-quinoline-3-carboxylic acid amide;
2  1-Butyl-N-[(3-fluorophenyl)-methyl]-4-methyl-2-oxo-7-(trifluoromethyl)-1H-quinoline-3-carboxylic acid amide;
3  N-[(3-Fluorophenyl)-methyl]-1,4-dimethyl-2-thioxo-7-(trifluoromethyl)-1H-quinoline-3-carboxylic acid amide;
4  N-[(3-Fluorophenyl)-methyl]-1-(2-methoxy-ethyl)-4-methyl-2-oxo-7-(trifluoromethyl)-1H-quinoline-3-carboxylic acid amide;
5  1-Ethyl-N-[(3-fluorophenyl)-methyl]-4-methyl-2-oxo-7-(trifluoromethyl)-1H-quinoline-3-carboxylic acid amide;
6  N-[(4-Fluorophenyl)-methyl]-1,4-dimethyl-2-oxo-7-(trifluoromethyl)-1H-quinoline-3-carboxylic acid amide;
7  N-[(4-Fluorophenyl)-methyl]-1-(2-methoxy-ethyl)-4-methyl-2-oxo-7-(trifluoromethyl)-1H-quinoline-3-carboxylic acid amide;
8  1-Ethyl-N-[(4-fluorophenyl)-methyl]-4-methyl-2-oxo-7-(trifluoromethyl)-1H-quinoline-3-carboxylic acid amide;
9  N-[(3-Fluorophenyl)-methyl]-1,4-dimethyl-2-oxo-1H-quinoline-3-carboxylic acid amide;
10  N-[(3-Fluorophenyl)-methyl]-1-(2-methoxy-ethyl)-4-methyl-2-oxo-1H-quinoline-3-carboxylic acid amide;

11 N-[(3-Fluorophenyl)-methyl]-4-methyl-2-oxo-1-propyl-7-(trifluoromethyl)-1H-quinoline-3-carboxylic acid amide;
12 N-[(3-Fluorophenyl)-methyl]-4-methyl-1-(3-methyl-butyl)-2-oxo-7-(trifluoromethyl)-1H-quinoline-3-carboxylic acid amide;
13 N-[(3-Fluorophenyl)-methyl]-4-methyl-1-(4-methyl-pentyl)-2-oxo-7-(trifluoromethyl)-1H-quinoline-3-carboxylic acid amide;
14 N-[(3-Fluorophenyl)-methyl]-1-(3-methoxy-propyl)-4-methyl-2-oxo-7-(trifluoromethyl)-1H-quinoline-3-carboxylic acid amide;
15 N-[(3-Fluorophenyl)-methyl]-1-[2-(2-methoxy-ethoxy)-ethyl]-4-methyl-2-oxo-7-(trifluoromethyl)-1H-quinoline-3-carboxylic acid amide;
16 7-Bromo-N-[(3-fluorophenyl)-methyl]-1,4-dimethyl-2-oxo-1H-quinoline-3-carboxylic acid amide;
17 7-Bromo-N-[(4-fluorophenyl)-methyl]-1,4-dimethyl-2-oxo-1H-quinoline-3-carboxylic acid amide;
18 7-Bromo-N-[(3-fluorophenyl)-methyl]-1-(2-methoxy-ethyl)-4-methyl-2-oxo-1H-quinoline-3-carboxylic acid amide;
19 7-Bromo-N-[(4-fluorophenyl)-methyl]-1-(2-methoxy-ethyl)-4-methyl-2-oxo-1H-quinoline-3-carboxylic acid amide;
20 7-Cyano-N-[(3-fluorophenyl)-methyl]-1,4-dimethyl-2-oxo-1H-quinoline-3-carboxylic acid amide;
21 7-Cyano-N-[(4-fluorophenyl)-methyl]-1,4-dimethyl-2-oxo-1H-quinoline-3-carboxylic acid amide;
22 7-Cyano-N-[(3-fluorophenyl)-methyl]-1-(2-methoxy-ethyl)-4-methyl-2-oxo-1H-quinoline-3-carboxylic acid amide;
23 7-Cyano-N-[(4-fluorophenyl)-methyl]-1-(2-methoxy-ethyl)-4-methyl-2-oxo-1H-quinoline-3-carboxylic acid amide;
24 N-(4,4-Dimethyl-pentyl)-1-(2-methoxy-ethyl)-4-methyl-2-oxo-7-(trifluoromethyl)-1H-quinoline-3-carboxylic acid amide;
25 N-(4,4-Dimethyl-pentyl)-1,4-dimethyl-2-oxo-7-(trifluoromethyl)-1H-quinoline-3-carboxylic acid amide;
26 2-[3-[(3-Fluorophenyl)-methyl-carbamoyl]-4-methyl-2-oxo-7-(trifluoromethyl)-1H-quinolin-1-yl]-acetic acid methyl ester;
27 3-[3-[(3-Fluorophenyl)-methyl-carbamoyl]-4-methyl-2-oxo-7-(trifluoromethyl)-1H-quinolin-1-yl]-propionic acid methyl ester;
28 2-[3-[(3-Fluorophenyl)-methyl-carbamoyl]-4-methyl-2-oxo-7-(trifluoromethyl)-1H-quinolin-1-yl]-acetic acid;
29 3-[3-[(3-Fluorophenyl)-methyl-carbamoyl]-4-methyl-2-oxo-7-(trifluoromethyl)-1H-quinolin-1-yl]-propionic acid;
30 N-[(3-Fluorophenyl)-methyl]-1-[1-(methoxymethyl)-propyl]-4-methyl-2-oxo-7-(trifluoromethyl)-1H-quinoline-3-carboxylic acid amide;
31 N-[(3-Fluorophenyl)-methyl]-1-[2-methoxy-1-(methoxymethyl)-ethyl]-4-methyl-2-oxo-7-(trifluoromethyl)-1H-quinoline-3-carboxylic acid amide;
32 N-[(3-Fluorophenyl)-methyl]-1-(2-methoxy-butyl)-4-methyl-2-oxo-7-(trifluoromethyl)-1H-quinoline-3-carboxylic acid amide;
33 N-[(3-Fluorophenyl)-methyl]-1,4-dimethyl-2-oxo-7-(trifluoromethyloxy)-1H-quinoline-3-carboxylic acid amide;
34 7-Fluoro-N-[(3-fluorophenyl)-methyl]-1,4-dimethyl-2-oxo-1H-quinoline-3-carboxylic acid amide;
35 N-[(3-Fluorophenyl)-methyl]-1-(2-methoxy-1-methyl-ethyl)-4-methyl-2-oxo-7-(trifluoromethyl)-1H-quinoline-3-carboxylic acid amide;
36 N-[(4-Fluorophenyl)-methyl]-1,4-dimethyl-2-thioxo-7-(trifluoromethyl)-1H-quinoline-3-carboxylic acid amide;
37 7-Chloro-N-[(3-fluorophenyl)-methyl]-1,4-dimethyl-2-oxo-1H-quinoline-3-carboxylic acid amide;
38 N-[(3-Fluorophenyl)-methyl]-1-(2-hydroxy-ethyl)-4-methyl-2-oxo-7-(trifluoromethyl)-1H-quinoline-3-carboxylic acid amide;
39 1-(2-Ethoxy-ethyl)-N-[(3-fluorophenyl)-methyl]-4-methyl-2-oxo-7-(trifluoromethyl)-1H-quinoline-3-carboxylic acid amide;
40 N-[(3-Fluorophenyl)-methyl]-1-isopropyl-4-methyl-2-oxo-7-(trifluoromethyl)-1H-quinoline-3-carboxylic acid amide;
41 N-[(3-Fluorophenyl)-methyl]-4-methyl-2-oxo-1-pentyl-7-(trifluoromethyl)-1H-quinoline-3-carboxylic acid amide;
42 N-[(3-Fluorophenyl)-methyl]-1-methyl-2-oxo-4-(trifluoromethyl)-1H-quinoline-3-carboxylic acid amide;
43 N-[(3-Fluorophenyl)-methyl]-1-(2-methoxy-propyl)-4-methyl-2-oxo-7-(trifluoromethyl)-1H-quinoline-3-carboxylic acid amide;
44 N-[(3-Fluorophenyl)-methyl]-4-methyl-2-oxo-1-tetrahydro-pyran-4-yl-7-(trifluoromethyl)-1H-quinoline-3-carboxylic acid amide; and
45 N-[(3-Fluorophenyl)-methyl]-4-methoxy-1-methyl-2-oxo-7-(trifluoromethyl)-1H-quinoline-3-carboxylic acid amide;

respectively in the form of the free compounds; the racemate; the enantiomers, diastereomers, mixtures of the enantiomers or diastereomers in any mixing ratio or of an individual enantiomer or diastereomer; or in the form of the salts of physiologically acceptable acids or bases; or in the form of solvates, in particular hydrates.

The substituted compounds according to the invention of the aforementioned general formula (I), and corresponding stereoisomers and also the respective corresponding salts and solvates are toxicologically safe and are therefore suitable as pharmaceutical active ingredients in pharmaceutical compositions.

The present invention therefore further relates to a pharmaceutical composition containing at least one compound according to general formula (I), in each case if appropriate in the form of one of its pure stereoisomers, in particular enantiomers or diastereomers, its racemates or in the form of a mixture of stereoisomers, in particular the enantiomers and/or diastereomers, in any desired mixing ratio, or respectively in the form of a physiologically acceptable salt, or respectively in the form of a corresponding solvate, and also optionally at least one pharmaceutically acceptable auxiliary and/or optionally at least one further active ingredient.

Further, 1-ethyl-N-(4-methoxybenzyl)-4-methyl-2-oxo-1,2-dihydroquinoline-3-carboxamide, also its respective corresponding salts and solvates are toxicologically safe and are therefore suitable as pharmaceutical active ingredients in pharmaceutical compositions.

The present invention therefore further relates to a pharmaceutical composition containing 1-ethyl-N-(4-methoxybenzyl)-4-methyl-2-oxo-1,2-dihydroquinoline-3-carboxamide, if appropriate in the form of a physiologically acceptable salt, or respectively in the form of a corresponding solvate thereof, and also optionally at least one pharmaceutically acceptable auxiliary and/or optionally at least one further active ingredient.

These pharmaceutical compositions according to the invention are suitable in particular for the modulation of KCNQ2/3 K$^+$ channels, preferably for KCNQ2/3 K$^+$ channel inhibition and/or KCNQ2/3 K⁺ channel stimulation, i.e. they exert an agonistic or antagonistic effect.

Likewise, the pharmaceutical compositions according to the invention are preferably suitable for the prophylaxis and/or treatment of disorders and/or diseases which are mediated, at least in part, by KCNQ2/3 K⁺ channels.

The pharmaceutical composition according to the invention is suitable for administration to adults and children, including toddlers and babies.

The pharmaceutical composition according to the invention may be prepared as a liquid, semisolid or solid pharmaceutical form, for example in the form of injection solutions, drops, juices, syrups, sprays, suspensions, tablets, patches, capsules, plasters, suppositories, ointments, creams, lotions, gels, emulsions, aerosols or in multiparticulate form, for example in the form of pellets or granules, if appropriate pressed into tablets, decanted in capsules or suspended in a liquid, and also be administered as much.

In addition to at least one substituted compound of general formula (I), if appropriate in the form of one of its pure stereoisomers, in particular enantiomers or diastereomers, its racemate or in the form of mixtures of the stereoisomers, in particular the enantiomers or diastereomers, in any desired mixing ratio, or if appropriate in the form of a corresponding salt or respectively in the form of a corresponding solvate, the pharmaceutical composition according to the invention conventionally may contain further physiologically acceptable pharmaceutical auxiliaries which, for example, can be selected from the group consisting of excipients, fillers, solvents, diluents, surface-active substances, dyes, preservatives, blasting agents, slip additives, lubricants, aromas and binders.

The selection of the physiologically acceptable auxiliaries and also the amounts thereof to be used depend on whether the pharmaceutical composition is to be applied orally, subcutaneously, parenterally, intravenously, intraperitoneally, intradermally, intramuscularly, intranasally, buccally, rectally or locally, for example to infections of the skin, the mucous membranes and of the eyes. Preparations in the form of tablets, dragées, capsules, granules, pellets, drops, juices and syrups are preferably suitable for oral application; solutions, suspensions, easily reconstitutable dry preparations and also sprays are preferably suitable for parenteral, topical and inhalative application. The substituted compounds according to the invention used in the pharmaceutical composition according to the invention in a repository, in a dissolved form or in a plaster, and further agents promoting skin penetration being added if appropriate, are suitable percutaneous application preparations. Orally or percutaneously applicable preparation forms can release the respective substituted compound according to the invention also in a delayed manner.

The pharmaceutical compositions according to the invention can be prepared with the aid of conventional means, devices, methods and process known in the art, such as are described for example in "Remington's Pharmaceutical Sciences", A. R. Gennaro (Editor), 17$^{th}$ edition, Mack Publishing Company, Easton, Pa., 1985, in particular in Part 8, Chapters 76 to 93. The corresponding description is introduced herewith by way of reference and forms part of the disclosure. The amount to be administered to the patient of the respective substituted compounds according to the invention of the above-indicated general formula (I) may vary and is for example dependent on the patient's weight or age and also on the type of application, the indication and the severity of the disorder. Conventionally, 0.001 to 100 mg/kg, preferably 0.05 to 75 mg/kg, particularly preferably 0.05 to 50 mg of at least one compound according to the invention are applied per kg of the patient's body weight.

The pharmaceutical composition according to the invention is preferably suitable for the treatment and/or prophylaxis of one or more diseases and/or disorders selected from the group consisting of pain, in particular pain selected from the group consisting of acute pain, chronic pain, neuropathic pain, muscular pain, visceral pain and inflammatory pain, epilepsy, urinary incontinence, anxiety, dependency, mania, bipolar disorders, migraine, cognitive diseases and dystonia-associated dyskinesias.

The pharmaceutical composition according to the invention is suitable particularly preferably for the treatment of pain, more particularly preferably of acute pain, chronic pain, neuropathic pain, visceral pain, inflammatory pain and muscular pain, and most particularly for the treatment of neuropathic pain.

The pharmaceutical composition according to the invention is also preferably suitable for the treatment and/or prophylaxis of epilepsy.

The present invention therefore further relates to at least one compound according to general formula (I), and also if appropriate of one or more pharmaceutically acceptable auxiliaries for use in the modulation of KCNQ2/3 K⁺ channels, preferably for use in KCNQ2/3 K⁺ channel inhibition and/or stimulation.

The present invention therefore further relates to at least one compound according to general formula (I), and also if appropriate of one or more pharmaceutically acceptable auxiliaries for use in the prophylaxis and/or treatment of disorders and/or diseases which are mediated, at least in part, by KCNQ2/3 K⁺ channels.

The present invention further relates to 1-ethyl-N-(4-methoxybenzyl)-4-methyl-2-oxo-1,2-dihydroquinoline-3-carboxamide, and also if appropriate of one or more pharmaceutically acceptable auxiliaries for use in the modulation of KCNQ2/3 K⁺ channels, preferably for use in KCNQ2/3 K⁺ channel inhibition and/or stimulation.

The present invention therefore further relates to 1-ethyl-N-(4-methoxybenzyl)-4-methyl-2-oxo-1,2-dihydroquinoline-3-carboxamide, and also if appropriate of one or more pharmaceutically acceptable auxiliaries for use in the prophylaxis and/or treatment of disorders and/or diseases which are mediated, at least in part, by KCNQ2/3 K⁺ channels.

Preference is given to at least one compound according to general formula (I), and optionally one or more pharmaceutically acceptable auxiliaries for use in the prophylaxis and/or treatment of disorders and/or diseases selected from the group consisting of pain, in particular pain selected from the group consisting of acute pain, chronic pain, neuropathic pain, muscular pain, visceral pain and inflammatory pain, epilepsy, urinary incontinence, anxiety, dependency, mania, bipolar disorders, migraine, cognitive diseases and dystonia-associated dyskinesias.

Preference is also given to 1-ethyl-N-(4-methoxybenzyl)-4-methyl-2-oxo-1,2-dihydroquinoline-3-carboxamide and optionally one or more pharmaceutically acceptable auxiliaries for use in the prophylaxis and/or treatment of disorders and/or diseases selected from the group consisting of pain, in particular pain selected from the group consisting of acute pain, chronic pain, neuropathic pain, muscular pain, visceral pain and inflammatory pain, epilepsy, urinary incontinence, anxiety, dependency, mania, bipolar disorders, migraine, cognitive diseases and dystonia-associated dyskinesias.

Particular preference is given to at least one compound according to general formula (I) and optionally one or more pharmaceutically acceptable auxiliaries for use in the prophylaxis and/or treatment of disorders and/or diseases selected from the group consisting of pain, in particular pain selected from the group consisting of acute pain, chronic pain, neuropathic pain, muscular pain, visceral pain and inflammatory pain, most particularly neuropathic pain.

Particular preference is also given to at least one compound according to general formula (I) and optionally one or more pharmaceutically acceptable auxiliaries for use in the prophylaxis and/or treatment of epilepsy.

The present invention therefore further relates to at least one compound according to general formula (I) and also if appropriate of one or more pharmaceutically acceptable auxiliaries for the modulation of KCNQ2/3 K$^+$ channels, preferably for KCNQ2/3 K$^+$ channel inhibition and/or stimulation.

The present invention therefore further relates to at least one compound according to general formula (I) and also if appropriate of one or more pharmaceutically acceptable auxiliaries for the prophylaxis and/or treatment of disorders and/or diseases which are mediated, at least in part, by KCNQ2/3 K$^+$ channels.

Preference is given to at least one compound according to general formula (I) and optionally one or more pharmaceutically acceptable auxiliaries for the prophylaxis and/or treatment of disorders and/or diseases selected from the group consisting of pain, especially pain selected from the group consisting of acute pain, chronic pain, neuropathic pain, muscular pain, visceral pain and inflammatory pain, epilepsy, urinary incontinence, anxiety, dependency, mania, bipolar disorders, migraine, cognitive diseases and dystonia-associated dyskinesias.

Particular preference is given to at least one compound according to general formula (I) and optionally one or more pharmaceutically acceptable auxiliaries for the prophylaxis and/or treatment of disorders and/or diseases selected from the group consisting of pain, in particular pain selected from the group consisting of acute pain, chronic pain, neuropathic pain, muscular pain, visceral pain and inflammatory pain, most particularly neuropathic pain.

Particular preference is also given to at least one compound according to general formula (I) and optionally one or more pharmaceutically acceptable auxiliaries for the prophylaxis and/or treatment of epilepsy.

Another aspect of the present invention is a method of treatment and/or prophylaxis of disorders and/or diseases, which are mediated, at least in part, by KCNQ2/3 K$^+$ channels, in a mammal, preferably of disorders and/or diseases selected from the group consisting of pain, preferably pain selected from the group consisting of acute pain, chronic pain, neuropathic pain, muscular pain, visceral pain and inflammatory pain, epilepsy, urinary incontinence, anxiety, dependency, mania, bipolar disorders, migraine, cognitive diseases and dystonia-associated dyskinesias, which comprises administering an effective amount of at least one compound of general formula (I) to the mammal.

The effectiveness against pain can be shown, for example, in the Bennett or Chung model (Bennett, G. J. and Xie, Y. K., A peripheral mononeuropathy in rat that produces disorders of pain sensation like those seen in man, Pain 1988, 33(1), 87-107; Kim, S. H. and Chung, J. M., An experimental model for peripheral neuropathy produced by segmental spinal nerve ligation in the rat, Pain 1992, 50(3), 355-363), by tail flick experiments (e.g. according to D'Amour and Smith (J. Pharm. Exp. Ther. 72, 74 79 (1941)) or by the formalin test (e.g. according to D. Dubuisson et al., Pain 1977, 4, 161-174). The effectiveness against epilepsy can be demonstrated, for example, in the DBA/2 mouse model (De Sarro et al., Naunyn-Schmiedeberg's Arch. Pharmacol. 2001, 363, 330-336).

The compounds according to the invention preferably have a EC$_{50}$ value of not more than 10000 nM or not more than 8000 nM, more preferably not more than 7000 nM or not more than 6000 nM, yet more preferably not more than 5000 nM or not more than 3000 nM, even more preferably not more than 2000 nM or not more than 1000 nM, yet even more preferably not more than 800 nM or not more than 700 nM, still more preferably not more than 600 nM or not more than 500 nM, yet still more preferably not more than 400 nM or not more than 300 nM, most preferably not more than 200 nM or not more than 150 nM and especially not more than 120 nM or not more than 100 nM. Methods for determining the EC$_{50}$ value are known to the person skilled in the art. The EC$_{50}$ value is preferably determined by fluorimetry, particularly preferably as described below under "pharmacological experiments".

The invention further provides processes for the preparation of the substituted compounds according to the invention.

The chemicals and reaction components used in the reactions and schemes described below are available commercially or in each case can be prepared by conventional methods known to the person skilled in the art.

The reactions described can each be carried out under the conventional conditions with which the person skilled in the art is familiar, for example with regard to pressure or the order in which the components are added. If appropriate, the person skilled in the art can determine the optimum procedure under the respective conditions by carrying out simple preliminary tests. The intermediate and end products obtained using the reactions described hereinbefore can each be purified and/or isolated, if desired and/or required, using conventional methods known to the person skilled in the art. Suitable purifying processes are for example extraction processes and chromatographic processes such as column chromatography or preparative chromatography. All of the process steps described below, as well as the respective purification and/or isolation of intermediate or end products, can be carried out partly or completely under an inert gas atmosphere, preferably under a nitrogen atmosphere.

If the substituted compounds according to the invention of the aforementioned general formula (I) are obtained, after preparation thereof, in the form of a mixture of their stereoisomers, preferably in the form of their racemates or other mixtures of their various enantiomers and/or diastereomers, they can be separated and if appropriate isolated using conventional processes known to the person skilled in the art. Examples include chromatographic separating processes, in particular liquid chromatography processes under normal pressure or under elevated pressure, preferably MPLC and HPLC processes, and also fractional crystallisation processes. These processes allow individual enantiomers, for example diastereomeric salts formed by means of chiral stationary phase HPLC or by means of crystallisation with chiral acids, for example (+)-tartaric acid, (−)-tartaric acid or (+)-10-camphorsulphonic acid, to be separated from one another.

General reaction scheme I (synthesis of precursors P1 and tautomeric form P2):

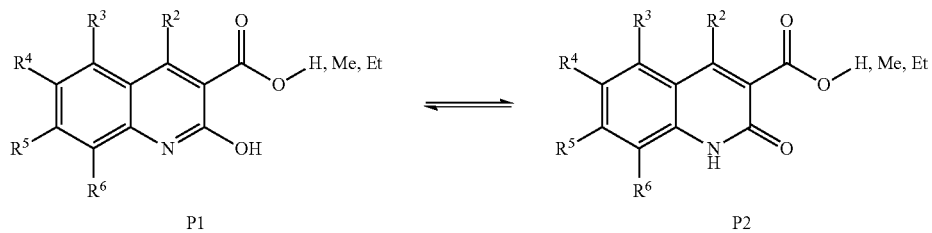

A plurality of syntheses of and synthesis paths to compounds of the general formula P1 or its tautomeric form P2 respectively with a very broad substitution pattern for residues $R^2$, $R^3$, $R^4$, $R^5$, and $R^6$ are known in the current specialist literature. Previously unknown intermediates of the general formula P1 or its tautomeric form P2 respectively with similar substitution patterns for residues $R^2$, $R^3$, $R^4$, $R^5$ and $R^6$ and, as outlined below and whose syntheses are not described in greater detail, can be produced by the person skilled in the art according to these known methods or by combination of the known methods.

General reaction scheme II:

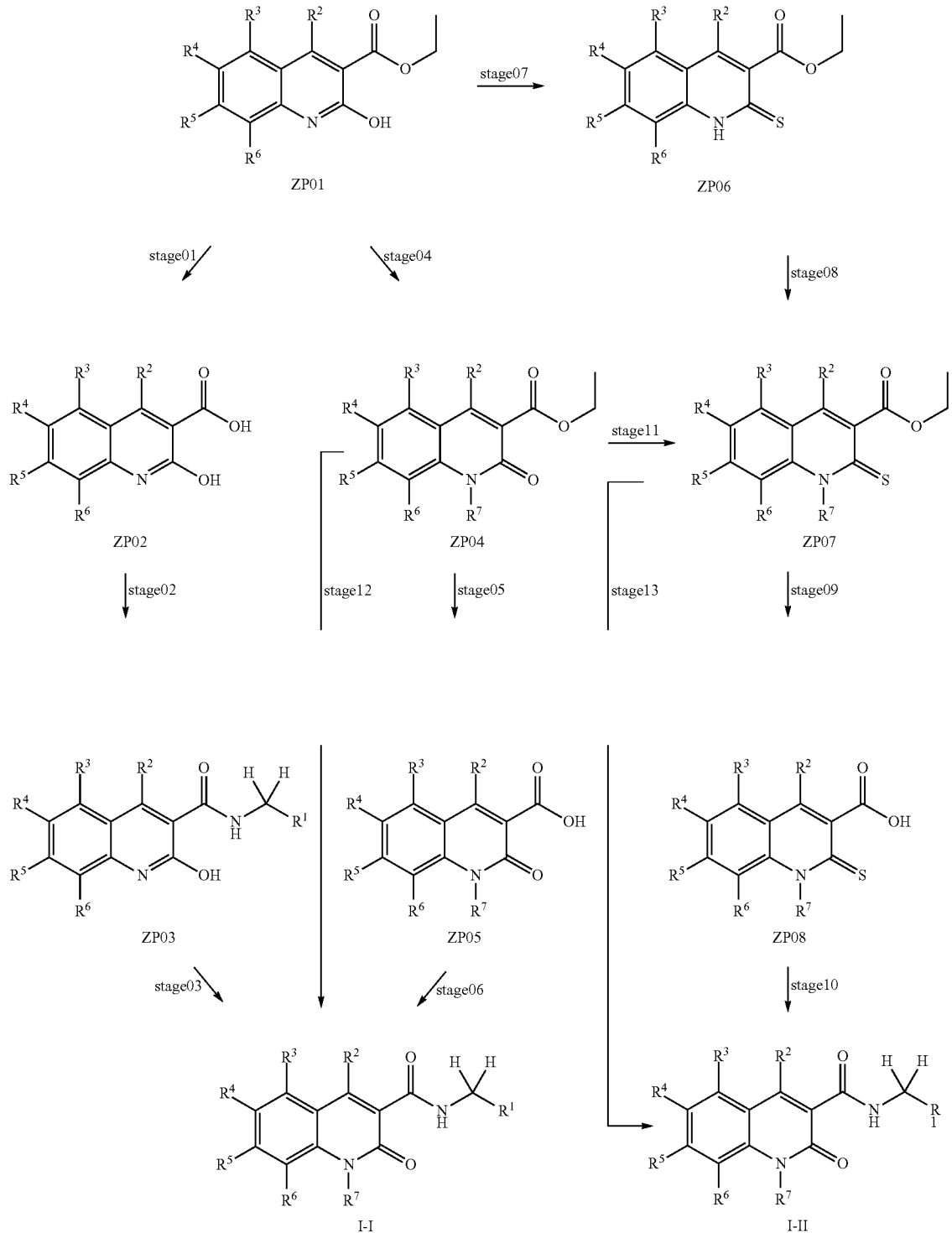

In stage01, stage05 and stage09, esters of the general formulae ZP01, ZP04 and ZP07, respectively, can be transformed into acids of the general formulae ZP02, ZP05 and ZP08, respectively, according to methods known to the person skilled in the art, for example, by employing a base, for example, lithium hydroxide.

In stage03, stage04 and stage08, quinonolones of the general formulae ZP03 and ZP01, and thioquinolones of the general formula ZP06, respectively, can be transformed into quinolones of the general formulae (I-I) and ZP04, and thioquinolones of the general formula ZP07, respectively, with compounds of the general formula $R^7$—$X^1$, wherein $X^1$ denotes a leaving group, for example, chlorine, bromine, iodine, methane sulphonate or p-toluene sulphonate, according to methods known to the person skilled in the art, for example, with the addition of a base, for example, potassium carbonate or sodium hydride.

In stage02, stage06 and stage10, acids of the general formulae ZP02, ZP05 and ZP08 respectively, can be transformed into amides of the general formulae ZP03, (I-I) and (I-II), respectively, with amines of the general formula $R^1$—$CH_2$—$NH_2$ according to methods known to the person skilled in the art, for example, using a suitable coupling reagent, for example, HATU.

In stage07 and stage11, quinolones of the general formulae ZP01 and ZP04, respectively, can be transformed into thioquinolones of the general formulae ZP06 and ZP07, respectively, according to methods known to the person skilled in the art, for example, by employing a thiation agent, for example, Lawesson's reagent or phosphorus pentasulfide.

In stage12 and stage 13, esters of the general formulae ZP04 or ZP07, respectively, can be converted to yield amides of the general formulae (I-I) or (I-II), respectively, with amines of the general formula $R^1$—$CH_2$—$NH_2$ according to methods known to the person skilled in the art, for example, with the addition of trimethylaluminium.

Thus obtained compounds of the general formulae (I-I) and (I-II) can be further transformed to introduce and/or exchange one or more of the substituents $R^1$, $R^2$, $R^3$, $R^4R^6$ and $R^7$ by simple derivatization reactions known to the person skilled in the art, for example, esterification, ester formation, amide formation, etherification, ether cleavage, substitution or cross-coupling reactions.

The invention will be described hereinafter with the aid of a number of examples. This description is intended merely by way of example and does not limit the general idea of the invention.

EXAMPLES

The indication "equivalents" ("eq.") means molar equivalents, "RT" means room temperature (23±7° C.), "M" is an indication of concentration in mol/l, "aq." means aqueous, "sat." means saturated, "sol." means solution, "conc." means concentrated.

Further abbreviations:
AcOH acetic acid
d days
brine saturated aqueous sodium chloride solution (NaCl sol.)
CC column chromatography on silica gel
dba dibenzylidene acetone
DCM dichloromethane
DIPEA N,N-diisopropylethylamine
DMF N,N-dimethylformamide
DMSO dimethyl sulfoxide
EtOAc ethyl acetate
EtOH ethanol
h hour(s)
HATU O-(7-aza-benzotriazol-1-yl)-N,N,N',N'-tetramethyluroniumhexafluorophosphate
m/z mass-to-charge ratio
MeOH methanol
MeCN acetonitrile
min minutes
MS mass spectrometry
MW microwave
$NEt_3$ triethylamine
RTG retigabine
RS reaction solution
THF tetrahydrofuran
TMEDA N,N,N',N'-tetramethylethylendiamine
v/v volume to volume
w/v weight per volume
Xantphos 4,5-bis(diphenylphosphino)-9,9-dimethylxanthene The yields of the compounds prepared were not optimised.
All temperatures are uncorrected.
All starting materials which are not explicitly described were either commercially available (the details of suppliers such as for example Acros, Avocado, Aldrich, Bachem, Fluka, Lancaster, Maybridge, Merck, Sigma, TCI, Oakwood, etc. can be found in the Symyx® Available Chemicals Database of MDL, San Ramon, US, or the SciFinder® Database of the ACS, Washington D.C., US, respectively, for example) or the synthesis thereof has already been described precisely in the specialist literature (experimental guidelines can be found in the Reaxys® Database of Elsevier, Amsterdam, NL, or the SciFinder® Database of the ACS, Washington D.C., US, respectively, for example) or can be prepared using the conventional methods known to the person skilled in the art.

The stationary phase used for the column chromatography was silica gel 60 (0.0-0-0.063 mm) from E. Merck, Darmstadt.

The mixing ratios of solvents or eluents for chromatography are specified in v/v.

All the intermediate products and exemplary compounds were analytically characterised by means of $^1$H-NMR spectroscopy. In addition, mass spectrometry tests (MS, m/z for [M+H]$^+$) were carried out for all the exemplary compounds and selected intermediate products.

Synthesis of Exemplary Compounds

Synthesis of Example 1

N-[(3-fluorophenyl)-methyl]-1,4-dimethyl-2-oxo-7-(trifluoromethyl)-1H-quinoline-3-carboxylic acid amide a) Synthesis of ethyl 4-methyl-2-oxo-7-(trifluoromethyl)-1H-quinoline-3-carboxylate A solution of 40.6 g (0.2 mol) 1-(2-amino-4-(trifluoromethyl)phenyl)ethanone and 41.6 (0.3 mol) $NEt_3$ in DCM (130 ml) was cooled by an ice/water-bath. A solution of 38.0 ml (0.3 mmol) ethyl 3-chloro-3-oxopropanoate in DCM (65 ml) was then added dropwise over 30 minutes while the temperature did not exceed 15° C., followed by stirring at RT for 2 h. The RS was subsequently quenched by addition of a 1M aq. $NaHCO_3$ solution (400 ml) and the organic layer was separated, dried over $MgSO_4$ and concentrated in vacuo. The residue obtained was dissolved in EtOH (350 ml) and 82 ml (0.2 mol, 21% w/v in EtOH) sodium ethylate were added, followed by stirring at RT for 72 h. The RS was then acidified with 5M aq. HOAc and concentrated in vacuo. The residue obtained was suspended in water (250 ml) and EtOAc (250 ml) and the resulting precipitate was filtered off. After drying at 40° C. in vacuo 42.8 g (0.14 mol, 72%) ethyl 4-methyl-2-oxo-7-(trifluoromethyl)-1H-quinoline-3-carboxylate was obtained, which was used in the next step without further purification.

b) Synthesis of 4-methyl-2-oxo-7-(trifluoromethyl)-1H-quinoline-3-carboxylic acid A 2M aq. LiOH sol. (125 ml) was added to a solution of 15.0 g (50.1 mmol) ethyl 4-methyl-2-oxo-7-(trifluoromethyl)-1H-quinoline-3-carboxylate in a MeOH/THF mixture (175 ml each) and the RS was subsequently heated at 60° C. for 16 h. The mixture was then concentrated in vacuo. The residue was taken up with water and adjusted to pH 2 with a 2M hydrochloric acid, followed by extraction with EtOAc. The organic layer was separated, washed with brine, dried over $MgSO_4$ and concentrated in vacuo. As residue 12.0 g (44.2 mmol, 88%) 4-methyl-2-oxo-7-(trifluoromethyl)-1H-quinoline-3-carboxylic acid was obtained, which was used in the next step without further purification.

c) Synthesis of N-[(3-Fluorophenyl)-methyl]-4-methyl-2-oxo-7-(trifluoromethyl)-1H-quinoline-3-carboxylic acid amide 926 mg (7.4 mmol) 3-Fluorobenzylamine, 2.55 g (6.7 mol) HATU and 2.7 ml (19.5 mmol) $NEt_3$ were added to a solution of 1.82 g (6.7 mmol) 4-methyl-2-oxo-7-(trifluoromethyl)-1H-quinoline-3-carboxylic acid in THF (50 ml). The RS was stirred at 50° C. for 16 h and was then diluted with EtOAc (50 ml) at RT. The resulting precipitate was filtered off and dried in vacuo to give 2.10 g (5.6 mmol, 83%) N-[(3-Fluorophenyl)-methyl]-4-methyl-2-oxo-7-(trifluoromethyl)-1H-quinoline-3-carboxylic acid amide, which was used in the next step without further purification.

d) Synthesis of N-[(3-Fluorophenyl)-methyl]-1,4-dimethyl-2-oxo-7-(trifluoromethyl)-1H-quinoline-3-carboxylic acid amide A solution of 500 mg (1.3 mmol) N-[(3-Fluorophenyl)-methyl]-4-methyl-2-oxo-7-(trifluoro-methyl)-1H-quinoline-3-carboxylic acid amide in DMSO (16 ml) was treated with 200 mg (1.5 mmol) $K_2CO_3$ and was subsequently stirred at RT for 1 h. Then 90 µl (1.5 mmol) iodomethane was added and the RS was heated at 50° C. for 16 h. After cooling to RT, the RS was diluted with water (10 ml) and EtOAc (30 ml). The organic layer was separated, washed with brine, dried over $MgSO_4$ and concentrated in vacuo. After crystallization from EtOAc of the residue, 327 mg (0.8 mmol, 63%) N-[(3-Fluorophenyl)-methyl]-1,4-dimethyl-2-oxo-7-(trifluoromethyl)-1H-quinoline-3-carboxylic acid amide (example 1) was obtained. MS: m/z 393.1 $[M+H]^+$.

Synthesis of Example 2

1-butyl-N-[(3-fluorophenyl)-methyl]-4-methyl-2-oxo-7-(trifluoromethyl)-1H-quinoline-3-carboxylic acid amide a) Synthesis of ethyl 1-butyl-4-methyl-2-oxo-7-(trifluoromethyl)-1H-quinoline-3-carboxylate A solution of 1.0 g (3.3 mmol) 4-methyl-2-oxo-7-(trifluoromethyl)-1H-quinoline-3-carboxylate (for synthesis see example 1, section a)) in DMSO (9 ml) was treated with 461 mg (3.3 mmol) $K_2CO_3$ and 360 µl (3.3 mmol) 1-bromobutane at RT and was subsequently heated at 50° C. for 90 mins. After cooling to RT the RS was diluted with water (30 ml) and extracted with EtOAc (3×50 ml). The combined organic layers were washed with water and brine, dried over $Na_2SO_4$ and concentrated in vacuo. After CC (EtOAc/hexane 1:8) of the residue, 480 mg (1.4 mmol, 40%) ethyl 1-butyl-4-methyl-2-oxo-7-(trifluoromethyl)-1H-quinoline-3-carboxylate was obtained.

b) Synthesis of 1-butyl-4-methyl-2-oxo-7-(trifluoromethyl)-1H-quinoline-3-carboxylic acid A solution of 160 mg (4.0 mmol) NaOH in water (10 ml) was added to a solution of 355 mg (1.0 mmol) ethyl 1-butyl-4-methyl-2-oxo-7-(trifluoromethyl)-1H-quinoline-3-carboxylate in EtOH (10 ml) at RT. The mixture was then heated at 80° C. for 16 h and subsequently EtOH was mostly removed in vacuo. The residue was diluted with water (20 ml) followed by acidification with 1M hydrochloric acid. This mixture was then extracted with EtOAC (3×30 ml). The combined organic layers were washed with water and brine, dried over $Na_2SO_4$ and concentrated in vacuo. As resulting residue 250 mg (0.8 mmol, 76%) 1-butyl-4-methyl-2-oxo-7-(trifluoromethyl)-1H-quinoline-3-carboxylic acid was obtained, which was used in the next step without further purification.

c) Synthesis of 1-butyl-N-[(3-fluorophenyl)-methyl]-4-methyl-2-oxo-7-(trifluoromethyl)-1H-quinoline-3-carboxylic acid amide 349 mg (0.9 mmol) HATU, 550 µl (3.1 mmol) DIPEA and 90 µl (0.8 mmol) 3-fluoro-benzylamine were added to a solution of 250 mg (0.8 mmol) 1-butyl-4-methyl-2-oxo-7-(trifluoromethyl)-1H-quinoline-3-carboxylic acid in DMF (3 ml) at RT and stirring was continued for 3 h. The RS was then diluted with water (20 ml) and extracted with EtOAc (3×30 ml). The combined organic layers were washed with water and brine, dried over $Na_2SO_4$ and concentrated in vacuo. After CC (EtOAc/hexane 1:4) of the residue, 180 mg (0.4 mmol, 54%) 1-butyl-N-[(3-fluorophenyl)-methyl]-4-methyl-2-oxo-7-(trifluoromethyl)-1H-quinoline-3-carboxylic acid amide (example 2) was obtained. MS: m/z 435.2 $[M+H]^+$.

Synthesis of Example 3

N-[(3-fluorophenyl)-methyl]-1,4-dimethyl-2-thioxo-7-(trifluoromethyl)-1H-quinoline-3-carboxylic acid amide a) Synthesis of ethyl 1,4-dimethyl-2-oxo-7-(trifluoromethyl)-1H-quinoline-3-carboxylate The conversion of ethyl 4-methyl-2-oxo-7-(trifluoromethyl)-1H-quinoline-3-carboxylate (for synthesis see example 1 section a)) and iodomethane into ethyl 1,4-dimethyl-2-oxo-7-(trifluoromethyl)-1H-quinoline-3-carboxylate was carried out according to the method described under example 2 Section a).

b) Synthesis of ethyl 1,4-dimethyl-2-thioxo-7-(trifluoromethyl)-1H-quinoline-3-carboxylate A solution of 460 mg (1.5 mmol) ethyl 1,4-dimethyl-2-oxo-7-(trifluoromethyl)-1H-quinoline-3-carboxylate in toluene (10 ml) was treated with 2.4 g (5.9 mmol) Lawesson's reagent at RT, followed by heating to 120° C. for 16 h. After cooling to RT the RS was quenched with a sat. aq. Na$_2$CO$_3$ solution (30 ml). The mixture was then extracted with EtOAc (3×30 ml). The combined organic layers were washed with brine, dried over Na$_2$SO$_4$ and concentrated in vacuo. CC (EtOAc/hexane 1:4) of the residue provided 400 mg (1.2 mmol, 82%) ethyl 1,4-dimethyl-2-thioxo-7-(trifluoromethyl)-1H-quinoline-3-carboxylate.

c) Synthesis of 1,4-dimethyl-2-thioxo-7-(trifluoromethyl)-1H-quinoline-3-carboxylic acid A solution of 270 mg (0.8 mmol) ethyl 1,4-dimethyl-2-thioxo-7-(trifluoromethyl)-1H-quinoline-3-carboxylate in AcOH (10 ml) was treated with a 40% w/v aq. hydrobromic acid (15 ml) at RT, followed by heating at 80° C. for 4 h. Further 40% w/v aq. hydrobromic acid (15 ml) was added and heating was continued at 80° C. for 16 h. Subsequently most of the HOAc was removed in vacuo and the residue was diluted with water (20 ml). This mixture was extracted with EtOAc (3×40 ml). The combined organic layers were washed with brine, dried over Na$_2$SO$_4$ and concentrated in vacuo. As resulting residue 210 mg (0.7 mmol, 85%) 1,4-dimethyl-2-thioxo-7-(trifluoromethyl)-1H-quinoline-3-carboxylic acid was obtained, which was used in the next step without further purification.

d) Synthesis of N-[(3-fluorophenyl)-methyl]-1,4-dimethyl-2-thioxo-7-(trifluoromethyl)-1H-quinoline-3-carboxylic acid amide Reaction of 220 mg (0.73 mmol) 1,4-dimethyl-2-thioxo-7-(trifluoromethyl)-1H-quinoline-3-carboxylic acid with 3-fluoro-benzylamine according to the method described under example 2 Section a) yielded 125 mg (0.3 mmol, 42%) N-[(3-fluorophenyl)-methyl]-1,4-dimethyl-2-thioxo-7-(trifluoromethyl)-1H-quinoline-3-carboxylic acid amide (example 3). MS: m/z 409.1 [M+H]$^+$.

Synthesis of Example 20

7-cyano-N-[(3-fluorophenyl)-methyl]-1,4-dimethyl-2-oxo-1H-quinoline-3-carboxylic acid amide To a solution of 247 mg (0.61 mmol) 7-bromo-N-[(3-fluorophenyl)-methyl]-1,4-dimethyl-2-oxo-1H-quinoline-3-carboxylic acid amide (example 16) in DMF (3 mL) were added 20 µL (0.22 mmol) TMEDA, 43 mg (0.37 mmol) Zinccyanide, 1 mg (0.003 mmol) Pd$_2$dba$_3$ and 7 mg (0.019 mmol) Xantphos. The reaction solution was degasses and flushed with nitrogen three times and then heated in MW to 160° C. for 4 min. After cooling to RT the mixture was filtered through celite and was washed with dichloromethane. The combined filtrates were concentrated in vacuo. After CC (EtOAc/hexane 1:2) of the residue, 91 mg (0.26 mmol, 43%) 7-cyano-N-[(3-fluorophenyl)-methyl]-1,4-dimethyl-2-oxo-1H-quinoline-3-carboxylic acid amide (example 20) were obtained. MS: m/z 350.1 [M+H]$^+$.

Synthesis of Example 28

2-[3-[(3-fluorophenyl)-methyl-carbamoyl]-4-methyl-2-oxo-7-(trifluoromethyl)-1H-quinolin-1-yl]-acetic acid To a solution of 350 mg (0.78 mmol) 2-[3-[(3-fluorophenyl)-methyl-carbamoyl]-4-methyl-2-oxo-7-(trifluoromethyl)-1H-quinolin-1-yl]-acetic acid methyl ester (example 26) in THF (6 ml) were added methanol (3 ml) and 1 ml (7.78 mmol) 7.78 M aq. LiOH sol. at RT. The reaction mixture was stirred at RT for 1.5 h. Then the solvent was evaporated, the residue was diluted with water (20 ml) and washed with DCM (10 ml). The aqueous part was acidified by 2 N HCl and then extracted with DCM (3×30 ml). The combined organic layers were dried over sodium sulfate and evaporated. After crystallization of the residue from an acetone-pentane solvent mixture 155 mg (0.35 mmol, 46%) 2-[3-[(3-fluorophenyl)-methyl-carbamoyl]-4-methyl-2-oxo-7-(trifluoromethyl)-1H-quinolin-1-yl]-acetic acid (example 28) were obtained. MS: m/z 437.1 [M+H]$^+$.

Synthesis of Example 38

N-[(3-fluorophenyl)-methyl]-1-(2-hydroxy-ethyl)-4-methyl-2-oxo-7-(trifluoromethyl)-1H-quinoline-3-carboxylic acid amide To a solution of 800 mg (1.83 mmol) N-[(3-fluorophenyl)-methyl]-1-(2-methoxy-ethyl)-4-methyl-2-oxo-7-(trifluoromethyl)-1H-quinoline-3-carboxylic acid amide (example 4) in DCM (30 ml) was added 0.26 ml (2.7 mmol) tribromoborane at −78° C. The reaction mixture was stirred at 0° C. for 2 h. Then the reaction mixture was cooled to −78° C. and quenched with a sat. NaHCO$_3$ sol. The reaction mixture was diluted with DCM (20 ml) and washed with a sat. NaHCO$_3$ sol. (20 ml), brine (20 ml), and water (20 ml), dried over Na$_2$SO$_4$ and concentrated in vacuum. After CC (EtOAc/hexane 1:4) of the residue, 750 mg (1.77 mmol, 97%) N-[(3-Fluorophenyl)-methyl]-1-(2-hydroxy-ethyl)-4-methyl-2-oxo-7-(trifluoromethyl)-1H-quinoline-3-carboxylic acid amide (example 38) were obtained. MS: m/z 423.1 [M+H]$^+$.

Synthesis of Example 44

N-[(3-fluorophenyl)-methyl]-4-methyl-2-oxo-1-tetrahydro-pyran-4-yl-7-(trifluoromethyl)-1H-quinoline-3-carboxylic acid amide a) Synthesis of 1-(2-(tetrahydro-2H-pyran-4-ylamino)-4-(trifluoromethyl)phenyl)ethanone To a solution of 500 mg (2.46 mmol) 1-(2-amino-4-(trifluoromethyl)phenyl)ethanone in methanol (18 ml) was added 250 µl (2.70 mmol) dihydro-2H-pyran-4(3H)-one at RT followed by the addition of 90 mg (0.73 mmol) decaborane. The reaction mixture was stirred at RT for 16 h. The mixture was evaporated under vacuum and residue diluted with ethyl acetate (20 ml). The organic layer was washed with water (20 ml), brine (20 ml), dried over anhydrous Na$_2$SO$_4$ and concentrated in vacuum. After CC (EtOAc/hexane 1:24) of the residue, 240 mg (0.83 mmol, 34%) 1-(2-(tetrahydro-2H-pyran-4-ylamino)-4-(trifluoromethyl)phenyl)ethanone were obtained.

b) Synthesis of ethyl 3-((2-acetyl-5-(trifluoromethyl)phenyl)(tetrahydro-2H-pyran-4-yl)amino)-3-oxopropanoate To a stirred solution of 400 mg (1.39 mmol) 1-(2-(tetrahydro-2H-pyran-4-ylamino)-4-(trifluoromethyl)phenyl)ethanone in benzene (5 ml) was added 360 µl (2.78 mmol) ethyl 3-chloro-3-oxopropanoate at 0° C. The reaction mixture was stirred at 80° C. for 4 h. Then the mixture was diluted with ethyl acetate (20 ml) and washed with water (20 ml), brine (20 ml), a sat. aq. Na₂CO₃ sol. (2×30 ml), dried over anhydrous Na₂SO₄ and concentrated in vacuo to yield 550 mg (1.37 mmol, 98%) ethyl 3-((2-acetyl-5-(trifluoromethyl)phenyl)(tetrahydro-2H-pyran-4-yl)amino)-3-oxopropanoate, which was used in the next step without further purification.

c) Synthesis of ethyl 4-methyl-2-oxo-1-(tetrahydro-2H-pyran-4-yl)-7-(trifluoromethyl)-1,2-dihydroquinoline-3-carboxylate To a stirred solution of 550 mg (1.37 mmol) ethyl 3-((2-acetyl-5-(trifluoromethyl)phenyl)-(tetrahydro-2H-pyran-4-yl)amino)-3-oxopropanoate in ethanol (5 ml) was added 60 mg (1.51 mmol, 60% suspension in mineral oil) NaH at 0° C. The reaction mixture was stirred at RT for 30 min. Then the mixture was evaporated to dryness, the residue was diluted with water (10 ml) and acidified with 2N HCl to pH ~3. The aq. part was extracted with ethyl acetate (3×10 ml). The combined organic layers were washed with water (10 ml), brine (10 ml), dried over anhydrous Na₂SO₄ and evaporated to get the crude which was again washed with sat. Na₂CO₃ to yield 330 mg (0.86 mmol, 62%) ethyl 4-methyl-2-oxo-1-(tetrahydro-2H-pyran-4-yl)-7-(trifluoromethyl)-1,2-dihydroquinoline-3-carboxylate which was used in the next step without further purification.

d) Synthesis of 4-methyl-2-oxo-1-(tetrahydro-2H-pyran-4-yl)-7-(trifluoromethyl)-1,2-dihydroquinoline-3-carboxylic acid To a solution of 330 mg (0.86 mmol) ethyl 4-methyl-2-oxo-1-(tetrahydro-2H-pyran-4-yl)-7-(trifluoromethyl)-1,2-dihydroquinoline-3-carboxylate in ethanol (6 ml) and water (0.6 ml) was added 140 mg (3.45 mmol) NaOH at RT. The reaction mixture was stirred at 80° C. for 16 h. Then the mixture was evaporated to dryness and the residue was diluted with water (5 ml) and acidified with 2N HCl to pH ~3. The aq. part was extracted with ethyl acetate (3×10 ml). The combined organic layers were washed with water (10 ml), brine (10 ml), dried over anhydrous Na₂SO₄ and concentrated in vacuum to give 280 mg (0.79 mmol, 91%) 4-methyl-2-oxo-1-(tetrahydro-2H-pyran-4-yl)-7-(trifluoromethyl)-1,2-dihydroquinoline-3-carboxylic acid which is used in the next step without further purification.

e) Synthesis of N-[(3-fluorophenyl)-methyl]-4-methyl-2-oxo-1-tetrahydro-pyran-4-yl-7-(trifluoromethyl)-1H-quinoline-3-carboxylic acid amide To a stirred solution of 280 mg (0.79 mmol) 4-methyl-2-oxo-1-(tetrahydro-2H-pyran-4-yl)-7-(trifluoromethyl)-1,2-dihydroquinoline-3-carboxylic acid in DCM (5 ml) were added 360 mg (0.95 mmol) HATU and 54 µl (3.15 mmol) DIPEA at 0° C. The reaction mixture was stirred for 5 min at 0° C. followed by the addition of 90 µl (0.79 mmol) 3-fluorobenzylamine. The reaction mixture was stirred at RT for 4 h. Then the mixture was diluted with water (5 ml) and extracted with DCM (3×10 ml). The combined organic layers were washed with water (10 ml), brine (10 ml), dried over anhydrous Na₂SO₄ and concentrated in vacuum. After CC (acetone/hexane 1:3) of the residue, 210 mg (0.45 mmol, 57%) N-[(3-fluorophenyl)-methyl]-4-methyl-2-oxo-1-tetrahydro-pyran-4-yl-7-(trifluoromethyl)-1H-quinoline-3-carboxylic acid amide (example 44) were obtained. MS: m/z 463.2 [M+H]⁺.

Synthesis of Further Examples

The synthesis of further examples was carried out according to the methods already described. Table 1 shows which compound was produced according to which method. It is evident to the person skilled in the art which educts and reagents were used in each case.

TABLE 1

| Example | Chemical name | Preparation analogous to example | MS m/z [M + H]⁺ |
|---|---|---|---|
| 4 | N-[(3-fluorophenyl)-methyl]-1-(2-methoxy-ethyl)-4-methyl-2-oxo-7-(trifluoromethyl)-1H-quinoline-3-carboxylic acid amide | 1 | 437.1 |
| 5 | 1-ethyl-N-[(3-fluorophenyl)-methyl]-4-methyl-2-oxo-7-(trifluoromethyl)-1H-quinoline-3-carboxylic acid amide | 1 | 407.1 |
| 6 | N-[(4-fluorophenyl)-methyl]-1,4-dimethyl-2-oxo-7-(trifluoromethyl)-1H-quinoline-3-carboxylic acid amide | 1 | 393.1 |
| 7 | N-[(4-fluorophenyl)-methyl]-1-(2-methoxy-ethyl)-4-methyl-2-oxo-7-(trifluoromethyl)-1H-quinoline-3-carboxylic acid amide | 1 | 437.1 |
| 8 | 1-ethyl-N-[(4-fluorophenyl)-methyl]-4-methyl-2-oxo-7-(trifluoromethyl)-1H-quinoline-3-carboxylic acid amide | 1 | 407.1 |
| 9 | N-[(3-fluorophenyl)-methyl]-1,4-dimethyl-2-oxo-1H-quinoline-3-carboxylic acid amide | 1 | 325.1 |
| 10 | N-[(3-fluorophenyl)-methyl]-1-(2-methoxy-ethyl)-4-methyl-2-oxo-1H-quinoline-3-carboxylic acid amide | 1 | 369.2 |
| 11 | N-[(3-fluorophenyl)-methyl]-4-methyl-2-oxo-1-propyl-7-(trifluoromethyl)-1H-quinoline-3-carboxylic acid amide | 1 | 421.1 |
| 12 | N-[(3-fluorophenyl)-methyl]-4-methyl-1-(3-methyl-butyl)-2-oxo-7-(trifluoromethyl)-1H-quinoline-3-carboxylic acid amide | 1 | 449.2 |
| 13 | N-[(3-fluorophenyl)-methyl]-4-methyl-1-(4-methyl-pentyl)-2-oxo-7-(trifluoromethyl)-1H-quinoline-3-carboxylic acid amide | 1 | 463.2 |
| 14 | N-[(3-fluorophenyl)-methyl]-1-(3-methoxy-propyl)-4-methyl-2-oxo-7-(trifluoromethyl)-1H-quinoline-3-carboxylic acid amide | 2 | 451.2 |
| 15 | N-[(3-fluorophenyl)-methyl]-1-[2-(2-methoxy-ethoxy)-ethyl]-4-methyl-2-oxo-7-(trifluoromethyl)-1H-quinoline-3-carboxylic acid amide | 2 | 481.2 |
| 16 | 7-bromo-N-[(3-fluorophenyl)-methyl]-1,4-dimethyl-2-oxo-1H-quinoline-3-carboxylic acid amide | 2 | 403.0 |
| 17 | 7-bromo-N-[(4-fluorophenyl)-methyl]-1,4-dimethyl-2-oxo-1H-quinoline-3-carboxylic acid amide | 2 | 403.0 |
| 18 | 7-bromo-N-[(3-fluorophenyl)-methyl]-1-(2-methoxy-ethyl)-4-methyl-2-oxo-1H-quinoline-3-carboxylic acid amide | 2 | 447.1 |
| 19 | 7-bromo-N-[(4-fluorophenyl)-methyl]-1-(2-methoxy-ethyl)-4-methyl-2-oxo-1H-quinoline-3-carboxylic acid amide | 2 | 447.1 |
| 21 | 7-cyano-N-[(4-fluorophenyl)-methyl]-1,4-dimethyl-2-oxo-1H-quinoline-3-carboxylic acid amide | 20 | 350.1 |
| 22 | 7-cyano-N-[(3-fluorophenyl)-methyl]-1-(2-methoxy-ethyl)-4-methyl-2-oxo-1H-quinoline-3-carboxylic acid amide | 20 | 394.1 |
| 23 | 7-cyano-N-[(4-fluorophenyl)-methyl]-1-(2-methoxy-ethyl)-4-methyl-2-oxo-1H-quinoline-3-carboxylic acid amide | 20 | 394.1 |
| 24 | N-(4,4-dimethyl-pentyl)-1-(2-methoxy-ethyl)-4-methyl-2-oxo-7-(trifluoromethyl)-1H-quinoline-3-carboxylic acid amide | 2 | 427.2 |
| 25 | N-(4,4-dimethyl-pentyl)-1,4-dimethyl-2-oxo-7-(trifluoromethyl)-1H-quinoline-3-carboxylic acid amide | 1 | 383.2 |

TABLE 1-continued

| Example | Chemical name | Preparation analogous to example | MS m/z $[M + H]^+$ |
|---|---|---|---|
| 26 | 2-[3-[(3-fluorophenyl)-methyl-carbamoyl]-4-methyl-2-oxo-7-(trifluoromethyl)-1H-quinolin-1-yl]-acetic acid methyl ester | 1 | 451.1 |
| 27 | 3-[3-[(3-fluorophenyl)-methyl-carbamoyl]-4-methyl-2-oxo-7-(trifluoromethyl)-1H-quinolin-1-yl]-propionic acid methyl ester | 1 | 465.1 |
| 29 | 3-[3-[(3-fluorophenyl)-methyl-carbamoyl]-4-methyl-2-oxo-7-(trifluoromethyl)-1H-quinolin-1-yl]-propionic acid | 28 | 451.1 |
| 30 | N-[(3-fluorophenyl)-methyl]-1-[1-(methoxymethyl)-propyl]-4-methyl-2-oxo-7-(trifluoromethyl)-1H-quinoline-3-carboxylic acid amide | 2 | 465.2 |
| 31 | N-[(3-fluorophenyl)-methyl]-1-[2-methoxy-1-(methoxymethyl)-ethyl]-4-methyl-2-oxo-7-(trifluoroethyl)-1H-quinoline-3-carboxylic acid amide | 2 | 481.2 |
| 32 | N-[(3-fluorophenyl)-methyl]-1-(2-methoxy-butyl)-4-methyl-2-oxo-7-(trifluoromethyl)-1H-quinoline-3-carboxylic acid amide | 2 | 465.2 |
| 33 | N-[(3-fluorophenyl)-methyl]-1,4-dimethyl-2-oxo-7-(trifluoromethyloxy)-1H-quinoline-3-carboxylic acid amide | 2 | 409.1 |
| 34 | 7-fluoro-N-[(3-fluorophenyl)-methyl]-1,4-dimethyl-2-oxo-1H-quinoline-3-carboxylic acid amide | 2 | 343.1 |
| 35 | N-[(3-fluorophenyl)-methyl]-1-(2-methoxy-1-methyl-ethyl)-4-methyl-2-oxo-7-(trifluoromethyl)-1H-quinoline-3-carboxylic acid amide | 2 | 451.2 |
| 36 | N-[(4-fluorophenyl)-methyl]-1,4-dimethyl-2-thioxo-7-(trifluoromethyl)-1H-quinoline-3-carboxylic acid amide | 3 | 409.1 |
| 37 | 7-chloro-N-[(3-fluorophenyl)-methyl]-1,4-dimethyl-2-oxo-1H-quinoline-3-carboxylic acid amide | 2 | 359.1 |
| 39 | 1-(2-ethoxy-ethyl)-N-[(3-fluorophenyl)-methyl]-4-methyl-2-oxo-7-(trifluoromethyl)-1H-quinoline-3-carboxylic acid amide | 2 | 451.2 |
| 40 | N-[(3-fluorophenyl)-methyl]-1-isopropyl-4-methyl-2-oxo-7-(trifluoromethyl)-1H-quinoline-3-carboxylic acid amide | 2 | 421.1 |
| 41 | N-[(3-fluorophenyl)-methyl]-4-methyl-2-oxo-1-pentyl-7-(trifluoromethyl)-1H-quinoline-3-carboxylic acid amide | 2 | 449.2 |
| 42 | N-[(3-fluorophenyl)-methyl]-1-methyl-2-oxo-4-(trifluoromethyl)-1H-quinoline-3-carboxylic acid amide | 2 | 379.1 |
| 43 | N-[(3-fluorophenyl)-methyl]-1-(2-methoxy-propyl)-4-methyl-2-oxo-7-(trifluoromethyl)-1H-quinoline-3-carboxylic acid amide | 2 | 451.2 |
| 45 | N-[(3-fluorophenyl)-methyl]-4-methoxy-1-methyl-2-oxo-7-(trifluoromethyl)-1H-quinoline-3-carboxylic acid amide | 2 | 409.1 |

Pharmacological Experiments
Method I. Fluorescence Assay Using a Voltage Sensitive Dye (Fluorimetry)

Human CHO-K1 cells expressing KCNQ2/3 channels are cultivated adherently at 37° C., 5% $CO_2$ and 95% humidity in cell culture bottles (e.g. 80 $cm^2$ TC flasks, Nunc) with DMEM-high glucose (Sigma Aldrich, D7777) including 10% FCS (PAN Biotech, e.g. 3302-P270521) or alternatively MEM Alpha Medium (1×, liquid, Invitrogen, #22571), 10% fetal calf serum (FCS) (Invitrogen, #10270-106, heat-inactivated) and the necessary selection antibiotics.

Before being sown out for the measurements, the cells are washed with 1×DPBS buffer $Ca^{2+}/Mg^{2+}$-free (e.g. Invitrogen, #14190-094) and detached from the bottom of the culture vessel by using Accutase (PAA Laboratories, #L11-007) (incubation with Accutase for 15 min at 37° C.). The cell number is determined using a CASY™ cell counter (TCC, Schärfe System). Depending on the optimal density for each individual cell line, 20,000-30,000 cells/well/100 μl are seeded onto 96-well Corning™ CellBIND™ assay plates (Flat Clear Bottom Black Polystyrene Microplates, #3340). Freshly seeded cells are then left to settle for one hour at room temperature, followed by incubation for 24 hours at 37° C., 5% $CO_2$ and 95% humidity.

The voltage-sensitive fluorescent dye from the Membrane Potential Assay Kit (Red™ Bulk format part R8123 for FLIPR, MDS Analytical Technologies™) is prepared by dissolving the contents of one vessel Membrane Potential Assay Kit Red Component A in 200 ml of extracellular buffer (ES buffer, 120 mM NaCl, 1 mM KCl, 10 mM HEPES, 2 mM $CaCl_2$, 2 mM $MgCl_2$, 10 mM glucose; pH 7.4). After removal of the nutrient medium, the cells are washed once with 200 μl of ES buffer, then loaded for 45 min at room temperature in 100 μl of dye solution in the dark.

Fluorescence measurements are carried out in a BMG Labtech FLUOstar™, BMG Labtech NOVOstar™ or BMG Labtech POLARstar™ instrument (525 nm excitation, 560 nm emission, Bottom Read mode). After incubation with the dye, 50 μl of the test substances in the desired concentrations, or 50 μl of ES buffer for control purposes, are applied to the wells of the assay plate and incubated for 30 min at room temperature while being shielded from light. The fluorescence intensity of the dye is then measured for 5 min and the fluorescence value $F_1$ of each well is thus determined at a given, constant time. 15 μl of a KCl solution are then added to each well (final concentration of potassium ions 92 mM). The change in fluorescence intensity is subsequently monitored until all the relevant values have been obtained (mainly 5-30 min). At a given time post KCl application, a fluorescence value $F_2$ is determined, in this case at the time of the fluorescence peak.

For calculation, the fluorescence intensity $F_2$ is corrected for the fluorescence intensity $F_1$, and the activity ($\Delta F/F$) of the target compound on the potassium channel is determined as follows:

$$\left(\frac{F_2 - F_1}{F_1}\right) \times 100 = \frac{\Delta F}{F}(\%)$$

In order to determine whether a substance has agonistic activity, $$\frac{\Delta F}{F}$$

can be related to $$\left(\frac{\Delta F}{F}\right)_K$$

of control wells.

$$\left(\frac{\Delta F}{F}\right)_K$$

is determined by adding to the well only the buffer solution instead of the test substance, determining the value $F_{1K}$ of the fluorescence intensity, adding the potassium ions as described above, and measuring a value $F_{2K}$ of the fluorescence intensity. $F_{2K}$ and $F_{1K}$ are then calculated as follows:

$$\left(\frac{F_{2K}-F_{1K}}{F_{1K}}\right) \times 100 = \left(\frac{\Delta F}{F}\right)_K (\%)$$

A substance has an agonistic activity on the potassium channel if $$\frac{\Delta F}{F}$$

is greater than $$\left(\frac{\Delta F}{F}\right)_{K:}$$

$$\frac{\Delta F}{F} \rangle \left(\frac{\Delta F}{F}\right)_K$$

Independently of the comparison of $$\frac{\Delta F}{F}$$

with $$\left(\frac{\Delta F}{F}\right)_K$$

it is possible to conclude that a target compound has agonistic activity if $$\frac{\Delta F}{F}$$

increases dose dependently.

Calculations of $EC_{50}$ and $IC_{50}$ values are carried out with the aid of 'Prism v4.0' software (GraphPad Software™).

Method II. Low-Intensity Tail Flick Test (Rat)

In the low-intensity tail flick test, the determination of the antinociceptive effect of the compounds according to the invention towards an acute noxious thermal stimulus is carried out by measuring the withdrawal reflex of the rat tail (tail flick) in response to a radiant heat beam (analgesia meter; model 2011 of the company Rhema Labortechnik, Hofheim, Germany) according to the method described by D'Amour and Smith (J. Pharm. Exp. Ther. 72, 74 79 (1941). To this end, the rats were placed in a plexiglas restrainer, and a low-intensity radiant heat beam (48° C.) was focused onto the dorsal surface of the tail root. The stimulus intensity was adjusted to result in a mean pre-drug control withdrawal latency of about 7 s, thus also allowing a supraspinal modulation of the spinally mediated acute nociceptive reflex. A cutoff time of 30 s was applied to avoid tissue damage. Male Sprague-Dawley rats (Janvier, Le Genest St. Isle, Frankreich) with weights of 200-250 g were used. 10 rats were used per group. Before administration of a compound according to the invention, the animals were pre-tested twice in the course of five minutes and the mean of these measurements was calculated as the pre-test mean. The antinociceptive effect was determined at 20, 40 and 60 min after peroral compound administration. The antinociceptive effect was calculated based on the increase in the tail withdrawal latency according to the following formula and is expressed as percentage of the maximum possible effect (MPE [%]):

$$MPE=[(T_1-T_0)/(T_2-T_0)]*100$$

In this, $T_0$ is the control latency time before and $T_1$ the latency time after administration of the compound, $T_2$ is the cutoff time and MPE is the maximum possible effect. Employing variant analysis (repeated measures ANOVA) allowed testing of statistically significant differences between the compounds according to the invention and the vehicle group. The significance level was set to $p \leq 0.05$. To determine the dose dependency, the particular compound according to the invention was administered in 3-5 logarithmically increasing doses, including a threshold dose and a maximum effective dose, and the $ED_{50}$ values were determined with the aid of regression analysis. The $ED_{50}$ calculation was performed at the time of maximum efficacy (usually 20 min after administration of the compounds).

Pharmacological Data

The pharmacological effects of the compounds according to the invention were determined as described hereinbefore (pharmacological experiments, methods I and II respectively).

The corresponding pharmacological data are summarized in Table 2.

TABLE 2

| Example | Fluorimetry % efficacy (RTG = 100%) | Fluorimetry $EC_{50}$ [nM] | Low intensity tail flick, rat, peroral, $ED_{50}$ or MPE (dose) [mg/kg] |
|---|---|---|---|
| 1 | 177 | 245 | 2.3 |
| 2 | 90 | 235 | |
| 3 | 101 | 124 | 24 (10.00) |
| 4 | 195 | 850 | 2.8 |
| 5 | 173 | 381 | |
| 6 | 169 | 189 | 0.6 |
| 7 | 146 | 598 | 47 (3.16) |
| 8 | 175 | 401 | |
| 9 | 63 | 5687 | |
| 10 | 22 | | |
| 11 | 167 | 406 | |
| 12 | 33 | | |
| 13 | 3 | | |
| 14 | 61 | 992 | |
| 15 | 78 | 2017 | |
| 20 | 143 | 1273 | |
| 21 | 136 | 837 | |
| 22 | 102 | 3137 | |
| 23 | 105 | 3891 | |
| 24 | 231 | 167 | |
| 25 | 258 | 68 | |
| 26 | 108 | 1006 | |
| 27 | 22 | | |
| 28 | 16 | | |
| 29 | 6 | | |

TABLE 2-continued

| Example | Fluorimetry % efficacy (RTG = 100%) | Fluorimetry EC$_{50}$ [nM] | Low intensity tail flick, rat, peroral, ED$_{50}$ or MPE (dose) [mg/kg] |
|---|---|---|---|
| 30 | 133 | 193 | |
| 31 | 46 | 80 | |
| 32 | 26 | | |
| 33 | 138 | 386 | |
| 34 | 105 | 3144 | |
| 35 | 118 | 114 | |
| 36 | 99 | 126 | |
| 37 | 139 | 729 | |
| 38 | 160 | 1827 | |
| 39 | 43 | | |
| 40 | 145 | 75 | |
| 41 | 18 | | |
| 42 | 103 | 4992 | |
| 43 | 100 | 1682 | |
| 44 | 36 | | |
| 45 | 190 | 215 | |

The invention claimed is:

1. A substituted compound of general formula (I)

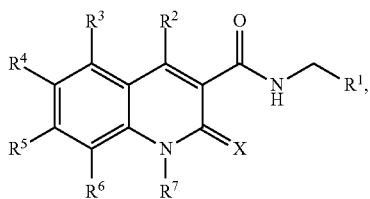

wherein

X denotes O or S,

R$^1$ represents a C$_{1-10}$-aliphatic residue, unsubstituted or mono- or polysubstituted;

a C$_{3-10}$-cycloaliphatic residue or a 3 to 10 membered heterocycloaliphatic residue, in each case unsubstituted or mono- or polysubstituted and in each case optionally bridged via a C$_{1-8}$ aliphatic group, which in turn may be unsubstituted or mono- or polysubstituted; aryl or heteroaryl, in each case unsubstituted or mono- or polysubstituted and in each case optionally bridged via a C$_{1-8}$ aliphatic group, which in turn may be unsubstituted or mono- or polysubstituted;

R$^2$ represents F; Cl; Br; I; CN; CF$_3$; C(=O)H; NO$_2$; OCF$_3$; SCF$_3$; a C$_{1-4}$-aliphatic residue, a C(=O)—C$_{1-4}$ aliphatic residue, a C(=O)—O—C$_{1-4}$ aliphatic residue, a C(=O)—NH—C$_{1-4}$ aliphatic residue, a C(=O)—N(C$_{1-4}$ aliphatic residue)$_2$, wherein the C$_{1-4}$ aliphatic residue may be in each case be unsubstituted or mono- or polysubstituted; a O—C$_{1-4}$-aliphatic residue, a O—C(=O)—C$_{1-4}$-aliphatic residue, a S—C$_{1-4}$-aliphatic residue, a S(=O)$_2$—C$_{1-4}$-aliphatic residue, a S(=O)$_2$—O—C$_{1-4}$-aliphatic residue, wherein the C$_{1-4}$ aliphatic residue may be in each case be unsubstituted or mono- or polysubstituted; a C$_{3-6}$-cycloaliphatic residue or a 3 to 6 membered heterocycloaliphatic residue, in each case unsubstituted or mono- or polysubstituted and in each case optionally bridged via a C$_{1-4}$ aliphatic group, which in turn may be unsubstituted or mono- or polysubstituted;

R$^3$, R$^4$, R$^5$ and R$^6$ each independently of one another represent H; F; Cl; Br; I; CN; CF$_3$; C(=O)H; C(=O)—OH; C(=O)—NH$_2$; SCF$_3$; S(=O)$_2$—OH; NO$_2$; OCF$_3$; a C$_{1-4}$-aliphatic residue, a C(=O)—C$_{1-4}$ aliphatic residue, a C(=O)—O—C$_{1-4}$ aliphatic residue, a C(=O)—NH—C$_{1-4}$ aliphatic residue, a C(=O)—N(C$_{1-4}$ aliphatic residue)$_2$, wherein the C$_{1-4}$ aliphatic residue may be in each case be unsubstituted or mono- or polysubstituted; a O—C$_{1-4}$-aliphatic residue, a O—C(=O)—C$_{1-4}$-aliphatic residue, a S—C$_{1-4}$-aliphatic residue, a S(=O)$_2$—C$_{1-4}$-aliphatic residue, a S(=O)$_2$—O—C$_{1-4}$-aliphatic residue, wherein the C$_{1-4}$ aliphatic residue may be in each case be unsubstituted or mono- or polysubstituted; a NH(C$_{1-4}$ aliphatic residue), a N(C$_{1-4}$ aliphatic residue)$_2$, a NH—C(=O)—C$_{1-4}$ aliphatic residue, a NH—S(=O)$_2$—C$_{1-4}$-aliphatic residue, a N(C$_{1-4}$ aliphatic residue)-C(=O)—C$_{1-4}$ aliphatic residue, or a N(C$_{1-4}$ aliphatic residue)-S(=O)$_2$—C$_{1-4}$ aliphatic residue, wherein the C$_{1-4}$ aliphatic residue may in each case be unsubstituted or mono- or polysubstituted; a C$_{3-6}$-cycloaliphatic residue or a 3 to 6 membered heterocycloaliphatic residue, in each case unsubstituted or mono- or polysubstituted and in each case optionally bridged via a C$_{1-4}$ aliphatic group, which in turn may be unsubstituted or mono- or polysubstituted;

R$^7$ represents a C$_{1-10}$-aliphatic residue, unsubstituted or mono- or polysubstituted; a C$_{3-10}$-cycloaliphatic residue or a 3 to 10 membered heterocycloaliphatic residue, in each case unsubstituted or mono- or polysubstituted and in each case optionally bridged via a C$_{1-8}$ aliphatic group, which in turn may be unsubstituted or mono- or polysubstituted;

on the condition that if R$^7$ denotes a 3 to 10 membered heterocycloaliphatic residue, the 3 to 10 membered heterocycloaliphatic residue is linked via a carbon atom, in which an "aliphatic group" and "aliphatic residue" can in each case be branched or unbranched, saturated or unsaturated, in which a "cycloaliphatic residue" and a "heterocycloaliphatic residue" can in each case be saturated or unsaturated, in which "mono- or polysubstituted" with respect to an "aliphatic group" and an "aliphatic residue" relates, with respect to the corresponding residues or groups, to the substitution of one or more hydrogen atoms each independently of one another by at least one substituent selected from the group consisting of F, Cl, Br, I, NO$_2$, NH$_2$, an NH(C$_{1-4}$ aliphatic residue), a NH—C(=O)—C$_{1-4}$ aliphatic residue, a NH—S(=O)$_2$—C$_{1-4}$ aliphatic residue, OH, OCF$_3$, a O—C$_{1-4}$-aliphatic residue, a O—C(=O)—C$_{1-4}$-aliphatic residue, SH, SCF$_3$, a S—C$_{1-4}$-aliphatic residue, S(=O)$_2$OH, a S(=O)$_2$—C$_{1-4}$-aliphatic residue, a S(=O)$_2$—O—C$_{1-4}$-aliphatic residue, a S(=O)$_2$—NH—C$_{1-4}$-aliphatic residue, CN, CF$_3$, CHO, COOH, a C$_{1-4}$-aliphatic residue, a C(=O)—C$_{1-4}$-aliphatic residue, a C(=O)—O—C$_{1-4}$-aliphatic residue, a C$_{3-6}$-cycloaliphatic residue, a 3 to 6 membered heterocycloaliphatic residue, C(=O)—NH$_2$, a C(=O)—NH(C$_{1-4}$ aliphatic residue), and a C(=O)—N(C$_{1-4}$ aliphatic residue)$_2$;

in which "mono- or polysubstituted" with respect to a "cycloaliphatic residue" and a "heterocycloaliphatic residue" relates, with respect to the corresponding residues, to the substitution of one or more hydrogen atoms each independently of one another by at least one substituent selected from the group consisting of F, Cl, Br, I, NO$_2$, NH$_2$, an NH(C$_{1-4}$ aliphatic residue), an N(C$_{1-4}$ aliphatic residue)$_2$, a NH—C(=O)—C$_{1-4}$ aliphatic residue, a NH—S(=O)$_2$—C$_{1-4}$ aliphatic residue, =O, OH, OCF$_3$, a O—C$_{1-4}$-aliphatic residue, a O—C(=O)—

$C_{1-4}$-aliphatic residue, SH, SCF$_3$, a S—$C_{1-4}$-aliphatic residue, S(=O)$_2$OH, a S(=O)$_2$—$C_{1-4}$-aliphatic residue, a S(=O)$_2$—O—$C_{1-4}$-aliphatic residue, a S(=O)$_2$—NH—$C_{1-4}$-aliphatic residue, CN, CF$_3$, CHO, COOH, a $C_{1-4}$-aliphatic residue, a C(=O)—$C_{1-4}$-aliphatic residue, a C(=O)—O—$C_{1-4}$-aliphatic residue, a $C_{3-6}$-cycloaliphatic residue, a 3 to 6 membered heterocycloaliphatic residue, C(=O)—NH$_2$, a C(=O)—NH($C_{1-4}$ aliphatic residue), and a C(=O)—N($C_{1-4}$ aliphatic residue)$_2$;

in which "mono- or polysubstituted" with respect to "aryl" and a "heteroaryl" relates, with respect to the corresponding residues, to the substitution of one or more hydrogen atoms each independently of one another by at least one substituent selected from the group consisting of F, Cl, Br, I, NO$_2$, NH$_2$

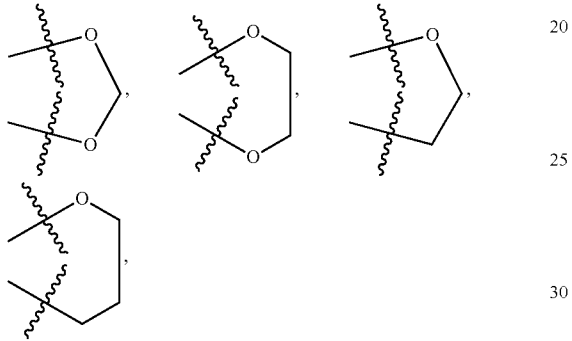

an NH($C_{1-4}$ aliphatic residue), an N($C_{1-4}$ aliphatic residue)$_2$, an NH—C(=O)—$C_{1-4}$ aliphatic residue, an NH—S(=O)$_2$—$C_{1-4}$ aliphatic residue, OH, OCF$_3$, a O—$C_{1-4}$-aliphatic residue, a O—C(=O)—$C_{1-4}$-aliphatic residue, SH, SCF$_3$, a S—$C_{1-4}$-aliphatic residue, S(=O)$_2$OH, a S(=O)$_2$—$C_{1-4}$-aliphatic residue, a S(=O)$_2$—O—$C_{1-4}$-aliphatic residue, a S(=O)$_2$—NH—$C_{1-4}$-aliphatic residue, CN, CF$_3$, C(=O)H, C(=O)OH, a $C_{1-4}$-aliphatic residue, a C(=O)—$C_{1-4}$-aliphatic residue, a C(=O)—O—$C_{1-4}$-aliphatic residue, a $C_{3-6}$-cycloaliphatic residue, a 3 to 6 membered heterocycloaliphatic residue, benzyl, aryl, heteroaryl, C(=O)—NH$_2$, a C(=O)—NH($C_{1-4}$ aliphatic residue), and a C(=O)—N($C_{1-4}$ aliphatic residue)$_2$;

with the exception of the following compound:
1-ethyl-N-(4-methoxybenzyl)-4-methyl-2-oxo-1,2-dihydroquinoline-3-carboxamide, in the form of the free compounds, the racemate, the enantiomers, diastereomers, mixtures of the enantiomers or diastereomers in any mixing ratio, or of an individual enantiomer or diastereomer, or in the form of the salts of physiologically acceptable acids or bases.

2. The compound according to claim 1, wherein
$R^1$ denotes a $C_{1-10}$-aliphatic residue, unsubstituted or mono- or polysubstituted with at least one substituent selected from the group consisting of F, Cl, Br, I, NO$_2$, NH$_2$, an NH($C_{1-4}$ aliphatic residue), OH, an O—$C_{1-4}$-aliphatic residue, OCF$_3$, SH, SCF$_3$, a S—$C_{1-4}$-aliphatic residue, CF$_3$, CN, a $C_{1-4}$-aliphatic residue and C(=O)—OH,
wherein the $C_{1-4}$-aliphatic residue in each case may be unsubstituted or mono- or polysubstituted with at least one substituent selected from the group consisting of F, Cl, Br, I, OH, OCF$_3$, CF$_3$ and an unsubstituted O—$C_{1-4}$-aliphatic residue, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, NO$_2$, NH$_2$, an NH($C_{1-4}$ aliphatic residue), an N($C_{1-4}$ aliphatic residue)$_2$, OH, =O, an O—$C_{1-4}$ aliphatic residue, OCF$_3$, SH, SCF$_3$, a S—$C_{1-4}$ aliphatic residue, CF$_3$, CN, a $C_{1-4}$ aliphatic residue, C(=O)—OH, a $C_{3-6}$ cycloaliphatic residue, and a 3 to 6 membered heterocycloaliphatic residue,
wherein the $C_{1-4}$-aliphatic residue in each case may be unsubstituted or mono- or polysubstituted with at least one substituent selected from the group consisting of F, Cl, Br, I, OH, OCF$_3$, CF$_3$ and an unsubstituted O—$C_{1-4}$-aliphatic residue, and
wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, NO$_2$, NH$_2$, an NH($C_{1-4}$ aliphatic residue), an N($C_{1-4}$ aliphatic residue)$_2$, OH, =O, an O—$C_{1-4}$ aliphatic residue, OCF$_3$, SH, SCF$_3$, a S—$C_{1-4}$ aliphatic residue, CF$_3$, CN, a $C_{1-4}$-aliphatic residue and C(=O)—OH,
and wherein the $C_{3-10}$-cycloaliphatic residue or the 3 to 10 membered heterocycloaliphatic residue may in each case optionally bridged via a $C_{1-8}$ aliphatic group, which in turn may be unsubstituted or mono- or polysubstituted with at least one substituent selected from the group consisting of F, Cl, Br, I, NO$_2$, NH$_2$, an NH($C_{1-4}$ aliphatic residue), an N($C_{1-4}$ aliphatic residue)$_2$, OH, =O, an O—$C_{1-4}$ aliphatic residue, OCF$_3$, SH, SCF$_3$, a S—$C_{1-4}$ aliphatic residue, CF$_3$, CN, a $C_{1-4}$-aliphatic residue and C(=O)—OH,
or denotes an aryl or heteroaryl, in each case unsubstituted or mono- or polysubstituted with at least one substituent selected from the group consisting of F, Cl, Br, I, NO$_2$, NH$_2$, an NH($C_{1-4}$ aliphatic residue), an N($C_{1-4}$ aliphatic residue)$_2$, OH, an O—$C_{1-4}$ aliphatic residue, OCF$_3$, SH, SCF$_3$, a S—$C_{1-4}$ aliphatic residue, CF$_3$, CN, a $C_{1-4}$-aliphatic residue, C(=O)—OH, C(=O)—CH$_3$, C(=O)—C$_2$H$_5$, C(=O)—O—CH$_3$ and C(=O)—O—C$_2$H$_5$, a $C_{3-6}$ cycloaliphatic residue, a 3 to 6 membered heterocycloaliphatic residue

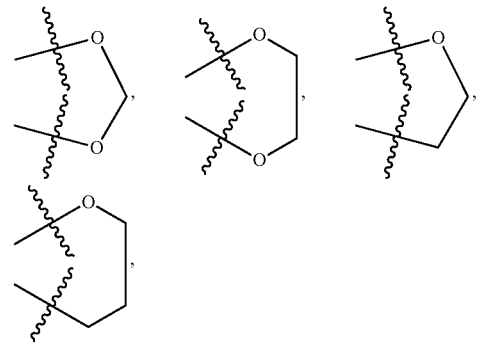

benzyl, phenyl, thienyl, pyridyl, furyl, thiazolyl and oxazolyl,
wherein the $C_{1-4}$-aliphatic residue in each case may be unsubstituted or mono- or polysubstituted with at least one substituent selected from the group consisting of F, Cl, Br, I, OH, OCF$_3$, CF$_3$ and an unsubstituted O—$C_{1-4}$-aliphatic residue, and wherein benzyl, phenyl, thienyl, pyridyl, furyl, thiazolyl and oxazolyl may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, an O—$C_{1-4}$ aliphatic residue, $OCF_3$, O—$CH_2$—OH, O—$CH_2$—O—$CH_3$, SH, $SCF_3$, a S—$C_{1-4}$ aliphatic residue, $CF_3$, CN, a $C_{1-4}$-aliphatic residue, C(=O)—OH, C(=O)—$CH_3$, C(=O)—$C_2H_5$, C(=O)—O—$CH_3$ and C(=O)—O—$C_2H_5$, and wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH, and wherein the aryl or the heteroaryl residue may in each case be optionally bridged via a $C_{1-8}$ aliphatic group, which in turn may be unsubstituted or mono- or polysubstituted with at least one substituent selected from the group consisting of F, Cl, Br, I, $NO_2$, $NH_2$, an $NH(C_{1-4}$ aliphatic residue), OH, an O—$C_{1-4}$ aliphatic residue, $OCF_3$, SH, $SCF_3$, a S—$C_{1-4}$ aliphatic residue, $CF_3$, CN and C(=O)—OH, X represents O or S;

$R^2$ represents F; Cl; Br; I; CN; $CF_3$; $NO_2$; $OCF_3$; $SCF_3$; a $C_{1-4}$-aliphatic residue, a S—$C_{1-4}$-aliphatic residue, a O—$C_{1-4}$-aliphatic residue, wherein the $C_{1-4}$ aliphatic residue may be in each case be unsubstituted or mono- or polysubstituted; a $C_{3-6}$-cycloaliphatic residue or a 3 to 6 membered heterocycloaliphatic residue, in each case unsubstituted or mono- or polysubstituted and in each case optionally bridged via a $C_{1-4}$ aliphatic group, which in turn may be unsubstituted or mono- or polysubstituted, $R^3$, $R^4$, $R^5$ and $R^6$ each independently of one another represent H; F; Cl; Br; I; CN; $CF_3$; $OCF_3$; $SCF_3$; C(=O)H; C(=O)—OH; C(=O)—$NH_2$; S(=O)$_2$—OH; $NO_2$; a $C_{1-4}$-aliphatic residue, a C(=O)—$C_{1-4}$ aliphatic residue, a C(=O)—O—$C_{1-4}$ aliphatic residue, a C(=O)—NH—$C_{1-4}$ aliphatic residue, a C(=O)—N($C_{1-4}$ aliphatic residue)$_2$, a O—$C_{1-4}$-aliphatic residue, a O—C(=O)—$C_{1-4}$-aliphatic residue, a S—$C_{1-4}$-aliphatic residue, a S(=O)$_2$—$C_{1-4}$-aliphatic residue, a NH($C_{1-4}$ aliphatic residue), a N($C_{1-4}$ aliphatic residue)$_2$, a NH—C(=O)—$C_{1-4}$ aliphatic residue, and a NH—S(=O)$_2$—$C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, and a O—$C_{1-4}$-aliphatic residue; a $C_{3-6}$-cycloaliphatic residue or a 3 to 6 membered heterocycloaliphatic residue, in each case unsubstituted or mono- or polysubstituted with at least one substituent selected from the group consisting of F, Cl, Br, I, OH, a $C_{1-4}$-aliphatic residue and a O—$C_{1-4}$-aliphatic residue, and in each case optionally bridged via an unsubstituted $C_{1-4}$ aliphatic group, $R^7$ denotes a $C_{1-10}$-aliphatic residue, unsubstituted or mono- or polysubstituted with at least one substituent selected from the group consisting of F, Cl, Br, I, $NO_2$, $NH_2$, an $NH(C_{1-4}$ aliphatic residue), OH, an O—$C_{1-4}$-aliphatic residue, $OCF_3$, SH, $SCF_3$, a S—$C_{1-4}$-aliphatic residue, $CF_3$, CN, a $C_{1-4}$-aliphatic residue, a C(=O)—O—$C_{1-4}$-aliphatic residue and C(=O)—OH, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, C(=O)—OH, a $C_{3-6}$ cycloaliphatic residue, and a 3 to 6 membered heterocycloaliphatic residue, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH, and wherein the $C_{3-10}$-cycloaliphatic residue or the 3 to 10 membered heterocycloaliphatic residue may in each case optionally bridged via a $C_{1-8}$ aliphatic group, which in turn may be unsubstituted or mono- or polysubstituted with at least one substituent selected from the group consisting of F, Cl, Br, I, $NO_2$, $NH_2$, an $NH(C_{1-4}$ aliphatic residue), OH, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH, on the condition that if $R^7$ denotes a 3 to 10 membered heterocycloaliphatic residue, the 3 to 10 membered heterocycloaliphatic residue is linked via a carbon atom.

3. The compound according to claim 1, wherein $R^2$ represents F; Cl; Br; I; CN; $CF_3$; $NO_2$; $OCF_3$; $SCF_3$; a $C_{1-4}$-aliphatic residue, a S—$C_{1-4}$-aliphatic residue, a O—$C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, and an unsubstituted O—$C_{1-4}$-aliphatic residue, a $C_{3-6}$-cycloaliphatic residue or a 3 to 6 membered heterocycloaliphatic residue, in each case unsubstituted or mono- or polysubstituted with at least one substituent selected from the group consisting of F, Cl, Br, I, =O, OH, a $C_{1-4}$-aliphatic residue and a O—$C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, and an unsubstituted O—$C_{1-4}$-aliphatic residue, and wherein the $C_{3-6}$-cycloaliphatic residue or the 3 to 6 membered heterocycloaliphatic residue may in each case be optionally bridged via a $C_{1-4}$ aliphatic group, which in turn may be unsubstituted or mono- or polysubstituted with at least one substituent selected from the group consisting of F, Cl, Br, I, OH, an unsubstituted $C_{1-4}$-aliphatic residue and an unsubstituted O—$C_{1-4}$-aliphatic residue.

4. The compound according to claim 1, wherein
$R^3$, $R^4$, $R^5$ and $R^6$ each independently of one another represent H; F; Cl; Br; I; CN; $CF_3$; $OCF_3$; $SCF_3$; C(=O)H; C(=O)—OH; C(=O)—$NH_2$; S(=O)$_2$—OH; $NO_2$; a $C_{1-4}$-aliphatic residue, a C(=O)—$C_{1-4}$ aliphatic residue, a C(=O)—O—$C_{1-4}$ aliphatic residue, a O—$C_{1-4}$-aliphatic residue, a O—C(=O)—$C_{1-4}$-aliphatic residue, a S—$C_{1-4}$-aliphatic residue, a S(=O)$_2$—$C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, and a O—$C_{1-4}$-aliphatic residue; a $C_{3-6}$-cycloaliphatic residue or a 3 to 6 membered heterocycloaliphatic residue, in each case unsubstituted or mono- or polysubstituted with at least one substituent selected from the group consisting of F, Cl, Br, I, =O, OH, a $C_{1-4}$-aliphatic residue and a O—$C_{1-4}$-aliphatic residue, and in each case optionally bridged via an unsubstituted $C_{1-4}$ aliphatic group.

5. The compound according to claim 1, wherein
$R^3$, $R^4$, $R^5$ and $R^6$ each independently of one another are selected from the group consisting of H; F; Cl; Br; I; $NO_2$; $CF_3$; CN; $OCF_3$; $SCF_3$; a (C=O)—$C_{1-4}$ aliphatic residue, a $C_{1-4}$ aliphatic residue, O—$C_{1-4}$ aliphatic residue, a S—$C_{1-4}$ aliphatic residue, wherein the $C_{1-4}$-aliphatic residue in each case may be unsubstituted or mono- or polysubstituted with at least one substituent selected from the group consisting of F, Cl, and O—$CH_3$.

6. The compound according to claim 1, wherein at least one of $R^3$, $R^4$, $R^5$ and $R^6$ is ≠H.

7. The compound according to claim 1, wherein $R^1$ represents the partial structure (T1)

(T1)

wherein
m denotes 0, 1, 2, 3 or 4,
$R^{8a}$ and $R^{8b}$ each independently of one another represent H, F, Cl, Br, I, $NO_2$, $NH_2$, a NH($C_{1-4}$ aliphatic residue), OH, an O—$C_{1-4}$ aliphatic residue, $OCF_3$, SH, $SCF_3$, a S—$C_{1-4}$ aliphatic residue, $CF_3$, CN, a $C_{1-4}$ aliphatic residue or C(=O)—OH,
$R^{8c}$ denotes a $C_{1-4}$ aliphatic residue, unsubstituted or mono- or polysubstituted with at least one substituent selected from the group consisting of F, Cl, Br, I, $NO_2$, $NH_2$, an NH($C_{1-4}$ aliphatic residue), OH, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH,
or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, $NO_2$, $NH_2$, an NH($C_{1-4}$ aliphatic residue), an N($C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, C(=O)—OH, a $C_{3-6}$ cycloaliphatic residue and a 3 to 6 membered heterocycloaliphatic residue,
wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and
wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, $NH_2$, an NH($C_{1-4}$ aliphatic residue), an N($C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH,
or denotes an aryl or heteroaryl, in each case unsubstituted or mono- or polysubstituted with at least one substituent selected from the group consisting of F, Cl, Br, I, $NO_2$, $NH_2$, an NH($C_{1-4}$ aliphatic residue), an N($C_{1-4}$ aliphatic residue)$_2$, OH, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, C(=O)—OH, C(=O)—$CH_3$, C(=O)—$C_2H_5$, C(=O)—O—$CH_3$ and C(=O)—O—$C_2H_5$, a $C_{3-6}$ cycloaliphatic residue, a 3 to 6 membered heterocycloaliphatic residue

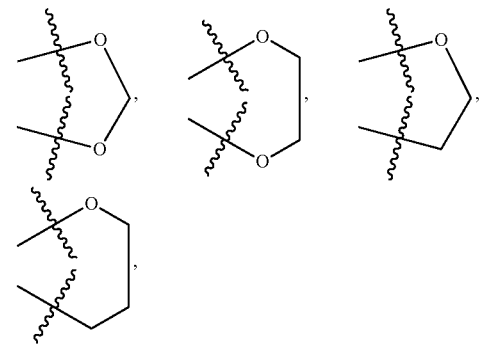

benzyl, phenyl, thienyl, pyridyl, furyl, thiazolyl and oxazolyl,
wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and
wherein benzyl, phenyl, thienyl, pyridyl, furyl, thiazolyl and oxazolyl may in each case may be unsubstituted or mono- or polysubstituted with at least one substituent selected from the group consisting of F, Cl, Br, I, $NO_2$, $NH_2$, an NH($C_{1-4}$ aliphatic residue), an N($C_{1-4}$ aliphatic residue)$_2$, OH, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, C(=O)—OH, C(=O)—$CH_3$, C(=O)—$C_2H_5$, C(=O)—O—$CH_3$ and C(=O)—O—$C_2H_5$, and
wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, $NH_2$, an NH($C_{1-4}$ aliphatic residue), an N($C_{1-4}$ aliphatic residue)$_2$, OH, =O, an O—$C_{1-4}$ aliphatic residue, OCF$_3$, SH, SCF$_3$, a S—$C_{1-4}$ aliphatic residue, CF$_3$, CN, a $C_{1-4}$-aliphatic residue and C(=O)—OH.

8. The compound according to claim 1, wherein $R^1$ represents the partial structure (T1),

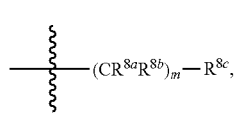

wherein
m denotes 0, 1, or 2,
$R^{8a}$ and $R^{8b}$ each independently of one another represent H, F, Cl, Br, I, an O—$C_{1-4}$ aliphatic residue or a $C_{1-4}$ aliphatic residue,
$R^{8c}$ denotes a $C_{1-4}$ aliphatic residue, unsubstituted or mono- or polysubstituted with at least one substituent selected from the group consisting of F, Cl, Br, I, an O—$C_{1-4}$ aliphatic residue, CF$_3$, and a $C_{1-4}$-aliphatic residue,
  wherein the $C_{1-4}$-aliphatic residue in each case may be unsubstituted or mono- or polysubstituted with at least one substituent selected from the group consisting of F, Cl, CF$_3$ and an unsubstituted O—$C_{1-4}$-aliphatic residue,
or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, an O—$C_{1-4}$ aliphatic residue, CF$_3$, and a $C_{1-4}$-aliphatic residue,
  wherein the $C_{1-4}$-aliphatic residue in each case may be unsubstituted or mono- or polysubstituted with at least one substituent selected from the group consisting of F, Cl, CF$_3$ and an unsubstituted O—$C_{1-4}$-aliphatic residue,
or denotes an aryl or heteroaryl, in each case unsubstituted or mono- or polysubstituted with at least one substituent selected from the group consisting of F, Cl, Br, I, OH, an O—$C_{1-4}$ aliphatic residue, OCF$_3$, CF$_3$, CN, a $C_{1-4}$-aliphatic residue, C(=O)—CH$_3$, C(=O)—C$_2$H$_5$, C(=O)—O—CH$_3$ and C(=O)—O—C$_2$H$_5$, a $C_{3-6}$ cycloaliphatic residue, a 3 to 6 membered heterocycloaliphatic residue, benzyl, phenyl, thienyl or pyridyl,
  wherein benzyl, phenyl, thienyl and pyridyl, may in each case may be unsubstituted or mono- or polysubstituted with at least one substituent selected from the group consisting of F, Cl, Br, I, OH, an O—$C_{1-4}$ aliphatic residue, OCF$_3$, CF$_3$, CN, a $C_{1-4}$-aliphatic residue, C(=O)—CH$_3$, C(=O)—C$_2$H$_5$, C(=O)—O—CH$_3$ and C(=O)—O—C$_2$H$_5$, and
  wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, OH, =O, an O—$C_{1-4}$ aliphatic residue, OCF$_3$, CF$_3$ a $C_{1-4}$-aliphatic residue and C(=O)—OH.

9. The compound according to claim 1, wherein $R^7$ denotes a $C_{1-10}$-aliphatic residue, unsubstituted or mono- or polysubstituted with at least one substituent selected from the group consisting of F, Cl, Br, I, NO$_2$, OH, an O—$C_{1-4}$-aliphatic residue, OCF$_3$, SH, SCF$_3$, a S—$C_{1-4}$-aliphatic residue, a C(=O)—O—$C_{1-4}$-aliphatic residue, COOH, CF$_3$, CN, and a $C_{1-4}$-aliphatic residue
  wherein the $C_{1-4}$-aliphatic residue in each case may be unsubstituted or mono- or polysubstituted with at least one substituent selected from the group consisting of F, Cl, Br, I, OH, OCF$_3$, CF$_3$ and an unsubstituted O—$C_{1-4}$-aliphatic residue,
or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, NO$_2$, OH, =O, an O—$C_{1-4}$ aliphatic residue, OCF$_3$, SH, SCF$_3$, a S—$C_{1-4}$ aliphatic residue, a C(=O)—O—$C_{1-4}$-aliphatic residue, CF$_3$, CN, a $C_{1-4}$-aliphatic residue, a $C_{3-6}$ cycloaliphatic residue, and a 3 to 6 membered heterocycloaliphatic residue,
  wherein the $C_{1-4}$-aliphatic residue in each case may be unsubstituted or mono- or polysubstituted with at least one substituent selected from the group consisting of F, Cl, Br, I, OH, OCF$_3$, CF$_3$ and an unsubstituted O—$C_{1-4}$-aliphatic residue, and
  wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, NO$_2$, OH, =O, an O—$C_{1-4}$ aliphatic residue, OCF$_3$, SH, SCF$_3$, a S—$C_{1-4}$ aliphatic residue, CF$_3$, CN, and a $C_{1-4}$-aliphatic residue,
and wherein the $C_{3-10}$-cycloaliphatic residue or the 3 to 10 membered heterocycloaliphatic residue may in each case optionally bridged via a $C_{1-8}$ aliphatic group, which in turn may be unsubstituted or mono- or polysubstituted with at least one substituent selected from the group consisting of F, Cl, Br, I, NO$_2$, OH, an O—$C_{1-4}$ aliphatic residue, a C(=O)—O—$C_{1-4}$-aliphatic residue, OCF$_3$, SH, SCF$_3$, a S—$C_{1-4}$ aliphatic residue, CF$_3$, CN, and a $C_{1-4}$-aliphatic residue,
on the condition that if $R^7$ denotes a 3 to 10 membered heterocycloaliphatic residue, the 3 to 10 membered heterocycloaliphatic residue is linked via a carbon atom.

10. The compound according to claim 1, wherein $R^7$ denotes a $C_{1-8}$-aliphatic residue, unsubstituted or mono- or polysubstituted with at least one substituent selected from the group consisting of F, Cl, Br, I, OH, an O—$C_{1-4}$-aliphatic residue, COOH, a C(=O)—O—$C_{1-4}$-aliphatic residue, OCF$_3$, SH, SCF$_3$, a S—$C_{1-4}$-aliphatic residue, CF$_3$, and a $C_{1-4}$-aliphatic residue
  wherein the $C_{1-4}$-aliphatic residue in each case may be unsubstituted or mono- or polysubstituted with at least one substituent selected from the group consisting of F, Cl, Br, I, OH, CF$_3$ and an unsubstituted O—$C_{1-4}$-aliphatic residue,
or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, OH, =O, an O—$C_{1-4}$ aliphatic residue, OCF$_3$, SCF$_3$, a S—$C_{1-4}$ aliphatic residue, a C(=O)—O—$C_{1-4}$-aliphatic residue, CF$_3$, and a $C_{1-4}$-aliphatic residue,
  wherein the $C_{1-4}$-aliphatic residue in each case may be unsubstituted or mono- or polysubstituted with at least one substituent selected from the group consisting of F, Cl, Br, I, OH, OCF$_3$, CF$_3$ and an unsubstituted O—C$_{1-4}$-aliphatic residue, and
wherein the C$_{3-10}$-cycloaliphatic residue or the 3 to 10 membered heterocycloaliphatic residue in each case may be bridged via an unsubstituted C$_{1-8}$ aliphatic group,
on the condition that if R$^7$ denotes a 3 to 10 membered heterocycloaliphatic residue, the 3 to 10 membered heterocycloaliphatic residue is linked via a carbon atom.

11. The compound according to claim 1, wherein R$^1$ represents the partial structure (T1),

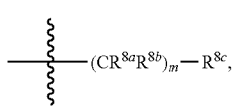

(T1)

wherein
m is 0, 1 or 2 and
R$^{8a}$ and R$^{8b}$ each independently of one another represent H, F, a O—C$_{1-4}$ aliphatic residue or a C$_{1-4}$ aliphatic residue;
R$^{8c}$ denotes a C$_{1-4}$ aliphatic residue, unsubstituted or mono- or polysubstituted with at least one substituent selected from the group consisting of F, Cl, Br, I, an unsubstituted O—C$_{1-4}$ aliphatic residue, CF$_3$, and an unsubstituted C$_{1-4}$-aliphatic residue,
or denotes a C$_{3-10}$-cycloaliphatic residue or a 3 to 10 membered heterocycloaliphatic residue, in each case unsubstituted or mono- or polysubstituted with at least one substituent selected from the group consisting of F, Cl, Br, I, an unsubstituted O—C$_{1-4}$ aliphatic residue, CF$_3$, and an unsubstituted C$_{1-4}$-aliphatic residue,
or
wherein
m is 0,
R$^{8a}$ and R$^{8b}$ each independently of one another represent H, F, a O—C$_{1-4}$ aliphatic residue or a C$_{1-4}$ aliphatic residue; and
R$^{8c}$ denotes an aryl or heteroaryl, in each case unsubstituted or mono- or polysubstituted with at least one substituent selected from the group consisting of F, Cl, Br, I, OH, an O—C$_{1-4}$ aliphatic residue, OCF$_3$, CF$_3$, CN, a C$_{1-4}$-aliphatic residue, C(=O)—CH$_3$, C(=O)—C$_2$H$_5$, C(=O)—O—CH$_3$, C(=O)—O—C$_2$H$_5$ and phenyl,
wherein phenyl may be unsubstituted or mono- or polysubstituted with at least one substituent selected from the group consisting of F, Cl, Br, I, OH, an O—C$_{1-4}$ aliphatic residue, OCF$_3$, CF$_3$, CN, a C$_{1-4}$-aliphatic residue, C(=O)—CH$_3$, C(=O)—C$_2$H$_5$, C(=O)—O—CH$_3$ and C(=O)—O—C$_2$H$_5$,
X represents O or S;
R$^2$ is selected from the group consisting of F; Cl; Br; CF$_3$; CH$_3$; C$_2$H$_5$, iso-propyl; cyclopropyl; and O—CH$_3$;
R$^3$, R$^4$, R$^5$ and R$^6$ are each independently of one another selected from the group consisting of H; F; Cl; Br; CF$_3$; CN; OCF$_3$ and NO$_2$;
R$^7$ denotes a C$_{1-6}$-aliphatic residue, unsubstituted or mono- or polysubstituted with at least one substituent selected from the group consisting of F, Cl, Br, I, OH, an O—C$_{1-4}$-aliphatic residue, COOH, a C(=O)—O—C$_{1-4}$-aliphatic residue, OCF$_3$, SH, SCF$_3$, a S—C$_{1-4}$-aliphatic residue, CF$_3$, and a C$_{1-4}$-aliphatic residue,
wherein the C$_{1-4}$-aliphatic residue in each case may be unsubstituted or mono- or polysubstituted with at least one substituent selected from the group consisting of OH, and an unsubstituted O—C$_{1-4}$-aliphatic residue,
or denotes an unsubstituted C$_{3-6}$-cycloaliphatic residue or an unsubstituted 3 to 6 membered heterocycloaliphatic residue,
on the condition that if R$^7$ denotes a 3 to 6 membered heterocycloaliphatic residue, the 3 to 6 membered heterocycloaliphatic residue is linked via a carbon atom.

12. The compound according to claim 1, wherein the compound is selected from the group consisting of:

1  N-[(3-Fluorophenyl)-methyl]-1,4-dimethyl-2-oxo-7-(trifluoromethyl)-1H-quinoline-3-carboxylic acid amide;
2  1-Butyl-N-[(3-fluorophenyl)-methyl]-4-methyl-2-oxo-7-(trifluoromethyl)-1H-quinoline-3-carboxylic acid amide;
3  N-[(3-Fluorophenyl)-methyl]-1,4-dimethyl-2-thioxo-7-(trifluoromethyl)-1H-quinoline-3-carboxylic acid amide;
4  N-[(3-Fluorophenyl)-methyl]-1-(2-methoxy-ethyl)-4-methyl-2-oxo-7-(trifluoromethyl)-1H-quinoline-3-carboxylic acid amide;
5  1-Ethyl-N-[(3-fluorophenyl)-methyl]-4-methyl-2-oxo-7-(trifluoromethyl)-1H-quinoline-3-carboxylic acid amide;
6  N-[(4-Fluorophenyl)-methyl]-1,4-dimethyl-2-oxo-7-(trifluoromethyl)-1H-quinoline-3-carboxylic acid amide;
7  N-[(4-Fluorophenyl)-methyl]-1-(2-methoxy-ethyl)-4-methyl-2-oxo-7-(trifluoromethyl)-1H-quinoline-3-carboxylic acid amide;
8  1-Ethyl-N-[(4-fluorophenyl)-methyl]-4-methyl-2-oxo-7-(trifluoromethyl)-1H-quinoline-3-carboxylic acid amide;
9  N-[(3-Fluorophenyl)-methyl]-1,4-dimethyl-2-oxo-1H-quinoline-3-carboxylic acid amide;
10  N-[(3-Fluorophenyl)-methyl]-1-(2-methoxy-ethyl)-4-methyl-2-oxo-1H-quinoline-3-carboxylic acid amide;
11  N-[(3-Fluorophenyl)-methyl]-4-methyl-2-oxo-1-propyl-7-(trifluoromethyl)-1H-quinoline-3-carboxylic acid amide;
12  N-[(3-Fluorophenyl)-methyl]-4-methyl-1-(3-methyl-butyl)-2-oxo-7-(trifluoromethyl)-1H-quinoline-3-carboxylic acid amide;
13  N-[(3-Fluorophenyl)-methyl]-4-methyl-1-(4-methyl-pentyl)-2-oxo-7-(trifluoromethyl)-1H-quinoline-3-carboxylic acid amide;
14  N-[(3-Fluorophenyl)-methyl]-1-(3-methoxy-propyl)-4-methyl-2-oxo-7-(trifluoromethyl)-1H-quinoline-3-carboxylic acid amide;
15  N-[(3-Fluorophenyl)-methyl]-1-[2-(2-methoxy-ethoxy)-ethyl]-4-methyl-2-oxo-7-(trifluoromethyl)-1H-quinoline-3-carboxylic acid amide;
16  7-Bromo-N-[(3-fluorophenyl)-methyl]-1,4-dimethyl-2-oxo-1H-quinoline-3-carboxylic acid amide;
17  7-Bromo-N-[(4-fluorophenyl)-methyl]-1,4-dimethyl-2-oxo-1H-quinoline-3-carboxylic acid amide;
18  7-Bromo-N-[(3-fluorophenyl)-methyl]-1-(2-methoxy-ethyl)-4-methyl-2-oxo-1H-quinoline-3-carboxylic acid amide;

19 7-Bromo-N-[(4-fluorophenyl)-methyl]-1-(2-methoxy-ethyl)-4-methyl-2-oxo-1H-quinoline-3-carboxylic acid amide;
20 7-Cyano-N-[(3-fluorophenyl)-methyl]-1,4-dimethyl-2-oxo-1H-quinoline-3-carboxylic acid amide;
21 7-Cyano-N-[(4-fluorophenyl)-methyl]-1,4-dimethyl-2-oxo-1H-quinoline-3-carboxylic acid amide;
22 7-Cyano-N-[(3-fluorophenyl)-methyl]-1-(2-methoxy-ethyl)-4-methyl-2-oxo-1H-quinoline-3-carboxylic acid amide;
23 7-Cyano-N-[(4-fluorophenyl)-methyl]-1-(2-methoxy-ethyl)-4-methyl-2-oxo-1H-quinoline-3-carboxylic acid amide;
24 N-(4,4-Dimethyl-pentyl)-1-(2-methoxy-ethyl)-4-methyl-2-oxo-7-(trifluoromethyl)-1H-quinoline-3-carboxylic acid amide;
25 N-(4,4-Dimethyl-pentyl)-1,4-dimethyl-2-oxo-7-(trifluoromethyl)-1H-quinoline-3-carboxylic acid amide;
26 2-[3-[(3-Fluorophenyl)-methyl-carbamoyl]-4-methyl-2-oxo-7-(trifluoromethyl)-1H-quinolin-1-yl]acetic acid methyl ester;
27 3-[3-[(3-Fluorophenyl)-methyl-carbamoyl]-4-methyl-2-oxo-7-(trifluoromethyl)-1H-quinolin-1-yl]propionic acid methyl ester;
28 2-[3-[(3-Fluorophenyl)-methyl-carbamoyl]-4-methyl-2-oxo-7-(trifluoromethyl)-1H-quinolin-1-yl]acetic acid;
29 3-[3-[(3-Fluorophenyl)-methyl-carbamoyl]-4-methyl-2-oxo-7-(trifluoromethyl)-1H-quinolin-1-yl]propionic acid;
30 N-[(3-Fluorophenyl)-methyl]-1-[1-(methoxymethyl)-propyl]-4-methyl-2-oxo-7-(trifluoromethyl)-1H-quinoline-3-carboxylic acid amide;
31 N-[(3-Fluorophenyl)-methyl]-1-[2-methoxy-1-(methoxymethyl)-ethyl]-4-methyl-2-oxo-7-(trifluoromethyl)-1H-quinoline-3-carboxylic acid amide;
32 N-[(3-Fluorophenyl)-methyl]-1-(2-methoxy-butyl)-4-methyl-2-oxo-7-(trifluoromethyl)-1H-quinoline-3-carboxylic acid amide;
33 N-[(3-Fluorophenyl)-methyl]-1,4-dimethyl-2-oxo-7-(trifluoromethyloxy)-1H-quinoline-3-carboxylic acid amide;
34 7-Fluoro-N-[(3-fluorophenyl)-methyl]-1,4-dimethyl-2-oxo-1H-quinoline-3-carboxylic acid amide;
35 N-[(3-Fluorophenyl)-methyl]-1-(2-methoxy-1-methyl-ethyl)-4-methyl-2-oxo-7-(trifluoromethyl)-1H-quinoline-3-carboxylic acid amide;
36 N-[(4-Fluorophenyl)-methyl]-1,4-dimethyl-2-thioxo-7-(trifluoromethyl)-1H-quinoline-3-carboxylic acid amide;
37 7-Chloro-N-[(3-fluorophenyl)-methyl]-1,4-dimethyl-2-oxo-1H-quinoline-3-carboxylic acid amide;
38 N-[(3-Fluorophenyl)-methyl]-1-(2-hydroxy-ethyl)-4-methyl-2-oxo-7-(trifluoromethyl)-1H-quinoline-3-carboxylic acid amide;
39 1-(2-Ethoxy-ethyl)-N-[(3-fluorophenyl)-methyl]-4-methyl-2-oxo-7-(trifluoromethyl)-1H-quinoline-3-carboxylic acid amide;
40 N-[(3-Fluorophenyl)-methyl]-1-isopropyl-4-methyl-2-oxo-7-(trifluoromethyl)-1H-quinoline-3-carboxylic acid amide;
41 N-[(3-Fluorophenyl)-methyl]-4-methyl-2-oxo-1-pentyl-7-(trifluoromethyl)-1H-quinoline-3-carboxylic acid amide;
42 N-[(3-Fluorophenyl)-methyl]-1-methyl-2-oxo-4-(trifluoromethyl)-1H-quinoline-3-carboxylic acid amide;
43 N-[(3-Fluorophenyl)-methyl]-1-(2-methoxy-propyl)-4-methyl-2-oxo-7-(trifluoromethyl)-1H-quinoline-3-carboxylic acid amide;
44 N-[(3-Fluorophenyl)-methyl]-4-methyl-2-oxo-1-tetrahydro-pyran-4-yl-7-(trifluoromethyl)-1H-quinoline-3-carboxylic acid amide; and
45 N-[(3-Fluorophenyl)-methyl]-4-methoxy-1-methyl-2-oxo-7-(trifluoromethyl)-1H-quinoline-3-carboxylic acid amide;

respectively in the form of the free compounds; the racemate; the enantiomers, diastereomers, mixtures of the enantiomers or diastereomers in any mixing ratio or of an individual enantiomer or diastereomer; or in the form of the salts of physiologically acceptable acids or bases.

13. A pharmaceutical composition comprising at least one compound according to claim 1
in the form of the free compounds; the racemate; the enantiomers, diastereomers, mixtures of the enantiomers or diastereomers in any mixing ratio or of an individual enantiomer or diastereomer; or in the form of the salts of physiologically acceptable acids or bases,
and optionally at least one pharmaceutically acceptable auxiliary and/or optionally at least one further active ingredient.

14. A method for the treatment of a disorder and/or disease in a mammal in need thereof, wherein said disorder and/or disease is mediated, at least in part, by KCNQ2/3 $K^+$ channels, and wherein said disorder and/or disease is selected from the group consisting of pain, epilepsy, urinary incontinence, anxiety, dependency, mania, bipolar disorders, migraine, and dystonia-associated dyskinesias, said method comprising administering an effective amount therefor of at least one compound according to claim 1 to the mammal.

* * * * *

UNITED STATES PATENT AND TRADEMARK OFFICE
CERTIFICATE OF CORRECTION

PATENT NO. : 8,653,102 B2  
APPLICATION NO. : 13/218579  
DATED : February 18, 2014  
INVENTOR(S) : Kühnert et al.

Page 1 of 1

It is certified that error appears in the above-identified patent and that said Letters Patent is hereby corrected as shown below:

Specification

Column 19, line 28, "$R^8$" -- should read -- $R^{8c}$ --.

Column 25, line 53, "5-$C_{1-4}$" -- should read -- S-$C_{1-4}$ --.

Column 30, line 59, "$(C_2H_3)(OCH_3)$" -- should read -- $(C_2H_5)(OCH_3)$ --.

Column 41, line 39, "$R^1, R^2, R^3, R^4R^6$ and $R^7$" -- should read -- $R^1, R^2, R^3, R^4R^5, R^6$ and $R^7$ --.

Signed and Sealed this  
Nineteenth Day of January, 2016

Michelle K. Lee  
*Director of the United States Patent and Trademark Office*